US 10,155,751 B2

(12) United States Patent
Hoffmann et al.

(10) Patent No.: US 10,155,751 B2
(45) Date of Patent: Dec. 18, 2018

(54) PYRAZOLYL-SUBSTITUTED HETEROARYLS AND THEIR USE AS MEDICAMENTS

(71) Applicant: Boehringer Ingelheim International GmbH, Ingelheim am Rhein (DE)

(72) Inventors: Matthias Hoffmann, Mittelbiberach (DE); Georg Dahmann, Biberach an der Riss (DE); Christian Gnamm, Biberach an der Riss (DE); Daniel Robert Fandrick, Danbury, CT (US); John Scott, Abingdon (GB); Clive McCarthy, Wantage (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/809,163

(22) Filed: Nov. 10, 2017

(65) Prior Publication Data
US 2018/0148433 A1   May 31, 2018

Related U.S. Application Data

(62) Division of application No. 15/255,283, filed on Sep. 2, 2016, now Pat. No. 9,845,314.
(Continued)

(51) Int. Cl.
*A61K 31/437* (2006.01)
*A61K 31/422* (2006.01)
(Continued)

(52) U.S. Cl.
CPC .......... *C07D 403/14* (2013.01); *A61K 31/416* (2013.01); *A61K 31/437* (2013.01);
(Continued)

(58) Field of Classification Search
CPC ... A61K 31/437; A61K 31/416; A61K 31/422
(Continued)

(56) References Cited

U.S. PATENT DOCUMENTS 9,504,684 B2 * 11/2016 Blomgren .......... A61K 31/4985
9,845,314 B2 * 12/2017 Hoffmann ............ A61K 31/416
(Continued)

FOREIGN PATENT DOCUMENTS

JP   2011529931 A   12/2011
WO   0183485 A1   11/2001
(Continued)

OTHER PUBLICATIONS

Pamuk et al., "The SYK Inhibitor Fostamatinib Limits Tissue Damage and Fibrosis in a Bleomycin-Induced Scleroderma MOUSE MODEL", 2014, ACR/ARHP Annual Meeting. Retrieved from the internet: http://acrabstracts.org/abstract/the-syk-inhibitor-fostamatinib-limitstissue-damage-and-?brosis in a-bleomycin-induced-scleroderma-mouse-model/.
(Continued)

*Primary Examiner* — Charanjit Aulakh
(74) *Attorney, Agent, or Firm* — Philip I. Datlow

(57) ABSTRACT

The invention relates to new substituted heteroaryls of formula 1 or of formula 1' wherein A is either N or CH,
wherein $R^2$ is selected from the group consisting of —$C_{1-3}$-alkyl, —$C_{1-3}$-haloalkyl, F, Br, Cl,
wherein Y is selected from —O— or —$CH_2$—,
and wherein $R^3$ is defined as in claim 1, and the pharmaceutically acceptable salts thereof,
and the use of these aforementioned compounds for the treatment of diseases such as asthma, COPD, allergic rhinitis, allergic dermatitis, lupus erythematodes, lupus nephritis and rheumatoid arthritis.

11 Claims, No Drawings

Related U.S. Application Data

(60) Provisional application No. 62/217,269, filed on Sep. 11, 2015.

(51) Int. Cl.

| | | |
|---|---|---|
| *A61K 31/416* | (2006.01) |
| *C07D 403/14* | (2006.01) |
| *A61K 45/06* | (2006.01) |
| *C07D 231/56* | (2006.01) |
| *C07D 405/14* | (2006.01) |
| *C07D 471/04* | (2006.01) |
| *C07D 493/04* | (2006.01) |
| *C07D 403/12* | (2006.01) |

(52) U.S. Cl.
CPC ............ *A61K 45/06* (2013.01); *C07D 231/56* (2013.01); *C07D 403/12* (2013.01); *C07D 405/14* (2013.01); *C07D 471/04* (2013.01); *C07D 493/04* (2013.01)

(58) Field of Classification Search
USPC .......................................... 514/303, 406, 376
See application file for complete search history.

(56) References Cited

U.S. PATENT DOCUMENTS

| | | |
|---|---|---|
| 2011/0201608 A1 | 8/2011 | Hoffmann et al. |
| 2011/0263549 A1 | 10/2011 | Fiegen et al. |
| 2012/0028939 A1 | 2/2012 | Hoffmann et al. |
| 2013/0029949 A1 | 1/2013 | Hoffmann et al. |
| 2015/0038488 A1 | 2/2015 | Currie et al. |
| 2015/0065489 A1 | 3/2015 | Hoffmann et al. |
| 2016/0244446 A1 | 8/2016 | Dahmann et al. |
| 2017/0008896 A1 | 1/2017 | Dahmann et al. |
| 2017/0073333 A1 | 3/2017 | Hoffmann et al. |

FOREIGN PATENT DOCUMENTS

| | | |
|---|---|---|
| WO | 2010015520 A1 | 2/2010 |
| WO | 2010027500 A1 | 3/2010 |
| WO | 2011092128 A1 | 8/2011 |
| WO | 2012123312 A1 | 9/2012 |
| WO | 2012/130780 A1 | 10/2012 |
| WO | 2013014060 A1 | 1/2013 |
| WO | 2013182546 A1 | 12/2013 |
| WO | 2014/100113 A2 | 6/2014 |
| WO | 2015017610 A1 | 2/2015 |
| WO | 2015140054 A1 | 9/2015 |
| WO | 2015140051 A8 | 12/2015 |
| WO | 2017042100 A1 | 3/2017 |

OTHER PUBLICATIONS

Can et al., "The Syk Inhibitor Fostamatinib Decreases the Severity of Colonic Mucosal Damage in a Rodent Model of Colitis", Journal of Crohn's and Colitis, 2015, pp. 907-917.

Rigel and Pfizer Sign Collaborative Research and License Agreement for the Treatment of Allergic Asthma and Other Respiratory Diseases, 2005. Retrieved from the internet: http://ir.rigel.com/phoenix.zhtml?c=120936&p=irol-newsArticle&ID=664627.

ClinicalTrials.gov, identifier NCT00952588, last updated on Feb. 13, 2014: https://clinicaltrials.gov/ct2/show/results/NCT00952588?term=AZD1152&rank=7&sect=X430156#othr <https://clinicaltrials.gov/ct2/show/results/NCT00952588?term=AZD1152&rank=7&sect=X430156%23othr>.

Gilliland et al., "The roles of FLT3 in hematopoiesis and leukemia", Blood, 2002, 100, pp. 1532-1542.

International Search Report and Written Opinion for corresponding application PCT/EP2016/070729, dated Oct. 31, 2016.

Thoma et al., "Orally bioavailable Syk inhibitors with activity in a rat PK/PD model", Bioorganic & Medicinal Chemistry Letters, 2016, vol. 25. No. 20., pp. 4642-4647.

Wander et al., "The evolving role of FLT3 inhibitors in acute myeloid leukemia: quizartinib and beyond", Ther Adv Hematol., 2014, 5:, pp. 65-77.

Yang et al., "AZD1152, a novel and selective aurora B kinase inhibitor, induces growth arrest, apoptosis, and sensitization for tubulin depolymerizing agent or topoisomerase II inhibitor in human acute leukemia cells in vitro and in vivo", Blood, 2007, vol. 110 No. 6, pp. 2034.

* cited by examiner

PYRAZOLYL-SUBSTITUTED HETEROARYLS AND THEIR USE AS MEDICAMENTS

The invention relates to new substituted heteroaryls of formula 1

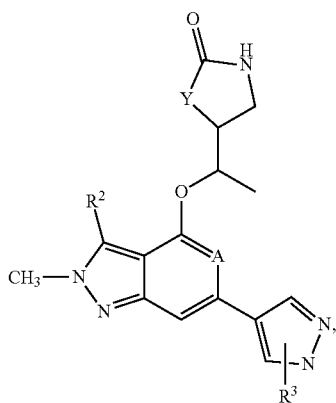

or of formula 1'

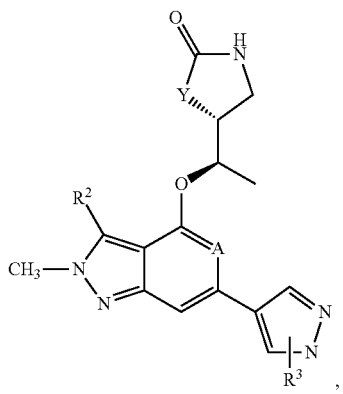

wherein A is either N or CH,
wherein Y is either —O— or —CH$_2$—
wherein R$^3$ is a substituent in ortho- or in meta-position of the pyrazolyl-ring of formula 1 and is selected from the group consisting of linear or branched —C$_{1-6}$-alkyl, —C$_{1-6}$-haloalkyl, —C$_{3-6}$-cycloalkyl, —C$_{1-4}$-alkylene-C$_{3-6}$-cycloalkyl, a five- or six-membered monocyclic heterocycle with 1, 2 or three heteroatoms each independently selected from O, S or N, a nine- to 10-membered bicyclic heterocycle with 1, 2 or 3 heteroatoms each independently selected from O, S or N,
wherein R$^3$ is optionally substituted by one, two, three or four substituents each independently from each other selected from the group consisting of halogen (F), —C$_{1-3}$-alkyl, oxo, —CN
wherein R$^2$ is selected from the group consisting of —C$_{1-3}$-alkyl, —C$_{1-3}$-haloalkyl, F, Br, Cl, and the pharmaceutically acceptable salts of the aforementioned compounds.

1. BACKGROUND TO THE INVENTION

1.1 SYK-Inhibitors

The present invention describes new compounds that inhibit the protein kinase SYK (spleen tyrosine kinase), the preparation and formulation thereof and their use for preparing a medicament.

SYK is an intracellular tyrosine kinase that has an important mediator function in the signal transduction of different receptors in B-cells, mast cells, monocytes, macrophages, neutrophils, T-cells, dendritic cells and epithelial cells. The receptors in which SYK performs an important function in signal transduction include for example the receptors for IgE (FcεRI) and IgG (FcγR1) on mast cells and B cells, the B-cell receptor (BCR) and the T-cell receptor (TCR) on B- and T-cells, the ICAM1 receptor (ICAM1R) on epithelial cells of the respiratory tract, the DAP12-receptor on natural killer cells, dendritic cells and osteoclasts, the dectin 1-receptor on a subpopulation of T-helper cells (Th-17 cells), as well as the integrin receptors for ß1-, ß2- and ß3-integrins on neutrophils, monocytes and macrophages (Wong et al.; Expert Opin. Investig. Drugs (2004) 13(7), 743-762; Ulanova et al.; Expert Opion. Ther. Target (2005) 9(5); 901-921; Wang et al.; J. Immunol. (2006) 177, 6859-6870; Leib und Gut-Landmann et al.; Nature Immunology (2007) 8, 630-638; Slack et al., European J. Immunol. (2007) 37, 1600-1612). The molecular processes are described best for the signal transduction of the FcεRI. In mast cells the binding of IgE to FcεRI causes the cross-linking of IgE-receptors and the recruiting and activation of Lyn (a tyrosine kinase from the Src family). Active Lyn phosphorylates so-called ITAM motifs, which are present in many of the receptors listed above, and thereby generates binding sites for the SH2-domain of SYK. As a result of the binding to the ITAM motif SYK is activated and then phosphorylates various substrates which are needed for the release of allergic and inflammatory mediators such as e.g. histamine and 3-hexosamidase (ßHA), as well as for the synthesis of lipid mediators, such as e.g. prostaglandins and leukotrienes.

In view of its central function in different signal transduction pathways SYK has been discussed as a therapeutic target for different diseases such as e.g. allergic rhinitis, asthma, autoimmune diseases, rheumatoid arthritis, osteopenia, osteoporosis, COPD and various leukaemias and lymphomas (Wong et al.; Expert Opin. Investig. Drugs (2004) 13(7), 743-762; Ulanova et al.; Expert Opion. Ther. Target (2005) 9(5); 901-921; Sigh and Masuda. Annual Reports in Medicinal Chemistry (2007) Vol 42; 379-391; Bajpai et al.; Expert Opin. Investig. Drugs (2008) Vol 15 (5); 641-659; Masuda and Schmitz; PPT (2008) Vol 21; 461-467; Riccaboni et al., Drug Discovery Today (2010) Vol 00 (0); 517-530; Efremov and Luarenti, Expert Opin Investig Drugs. (2011) 20(5):623-36).

Allergic rhinitis and asthma are diseases associated with allergic reactions and inflammatory processes and involving different cell types such as e.g. Mast cells, eosinophils, T-cells and dendritic cells. After exposure to allergens has occurred, the high affinity immunoglobulin receptors for IgE (FcεRI) and IgG (FcγR1) are activated and induce the release of pro-inflammatory mediators and bronchoconstrictors. An inhibitor of the SYK kinase activity should thus be able to inhibit these steps.

Rheumatoid arthritis (RA) is an autoimmune disease in which the bones and ligaments structures surrounding the joints are progressively destroyed. In the pathophysiology of RA, B-cells play a significant role, as has been demonstrated for example by the therapeutic use of rituximab, a B cell-depleting antibody. In addition to the function of SYK in the signal transduction of the BCR (which after being stimulated also induces the release of pro-inflammatory mediators), SYK also plays an important part in the maturation and proliferation of B cells (Cheng et al. Nature (1995) 378, 303-306, Cornall et al., PNAS (2000) 97(4), 1713-1718). An inhibitor of the SYK kinase activity may thus offer a therapeutic option for the treatment of autoimmune diseases such as RA and diseases with an increased proliferation of B cells, such as e.g. B-cell lymphomas.

Chronic obstructive pulmonary disease (COPD) is characterised by a successive deterioration in lung function and chronic inflammation of the airways, which is initiated and produced by noxious substances of all kinds and contributes to the maintenance of the course of the disease. At a cellular level, in COPD there is in particular a multiplication of T-lymphocytes, neutrophils, granulocytes and macrophages. In particular, there is an increase in the number of CD8-positive lymphocytes, that is directly connected with the impairment of lung function. Another characteristic of COPD are acute deteriorations in lung function (exacerbations), characterised by viral (e.g. Rhinovirus), or bacterial (e.g. *Streptococcus pneumoniae, Haemophilus influenzae* and *Moraxella catarrhalis*) infections.

In view of the pro-inflammatory function of SYK in macrophages, T-cells and neutrophils as described above (see: Wong et al.; Expert Opin. Investig. Drugs (2004) 13(7), 743-762; and references cited therein) an inhibitor of the SYK kinase activity could be a new therapeutic approach to the treatment of the inflammatory processes that underlie COPD. It has also been shown that SYK in epithelial cells of the respiratory tract is involved in the ICAM1R-mediated uptake and subsequent replication of the Rhinovirus and that a si-RNA against SYK blocks these steps (Wang et al.; J. Immunol. (2006) 177, 6859-6870; Lau et al.; J. Immunol. (2008) 180, 870-880). Thus, an inhibitor of the SYK kinase activity could also be used therapeutically in exacerbations caused by Rhinoviruses.

Various studies suggest that SYK is involved in the malignant transformation of lymphocytes (summarised in Sigh and Masuda, Annual Reports in Medicinal Chemistry (2007) Vol 42; 379-391). A TEL-SYK fusion protein with a constitutive SYK activity transformed B cells of a patient with myelodysplastic syndrome, a constitutively active ITK-SYK fusion protein was isolated from patients with peripheral T-cell lymphomas (PTCL). Moreover, constitutively active SYK was found in B-cell lymphoma cells of patients, especially in B-lineage acute lymphoblastic leukemia (B-ALL), follicular lymphoma (FL), diffuse large B-cell lymphoma (DLBCL), mantle cell lymphomas and B cell Non-Hodgkin Lymphomas (NHLs) as well as in acute myeloid leukemia (AML). On the basis of these data it seems that SYK is a proto-oncogene in haematopoietic cells and represents a potential target for the treatment of certain leukaemias and lymphomas.

Idiophathic thrombocytopenic purpura (ITP) is an autoimmune disease in which IgG autoantibodies against antigens present on platelets bind to and destroy platelets. Patients with ITP have an accelerated clearence of circulating IgG-coated platelets via macrophages in the spleen and the liver. In view of the pro-inflammatory FcγR-mediated function of SYK in macrophages an inhibitor of SYK is considered to have a therapeutic benefit in FcγR-mediated cytopenias like ITP. Indeed the SYK inhibitor R788 (R406) improved platelet counts in a single center, oben label study in patients with ITP (Podolanczuk et al; Blood (2009) 113, 3154-3169).

Bullous pemphigoid (Ujiie et al. Journal of Dermatology 2010; 37: 194-204) is a chronic, autoimmune, subepidermal, blistering skin disease that rarely involves mucous membranes. Bullous pemphigoid is characterized by the presence of immunoglobulin G (IgG) autoantibodies specific for the hemidesmosomal bullous pemphigoid antigens BP230 (BPAg1) and BP180 (BPAg2). Pemphigus vulgaris (Venugopal et al. Dermatol. Clin. 2011; 29:373-80) is a chronic blistering skin disease with skin lesions that are rarely pruritic, but which are often painful. Pemphigus vulgaris is an autoimmune disease caused by IgG autoantibodies directed against both desmoglein 1 and desmoglein 3 resulting in the loss of cohesion between keratinocytes in the epidermis. It is characterized by extensive flaccid blisters and mucocutaneous erosions. In both diseases IgG autoantibodies bind to Fc receptor gamma (FcRγ) and activate FcRγ and downstream signaling via SYK kinase. Thus, an inhibitor of the SYK kinase activity which blocks downstream signalling of the FcRγ could be used therapeutically to treat patients with bullous pemphigoid and pemphigus vulgaris.

Systemic lupus erythematosus (SLE) is a chronic autoimmune disease which can affect basically any organ of the body. It is characterised by a multisystem inflammation of the microvascular and the presence of autoantibodies. FcγR-deficient mice are protected from several aspects of SLE in disease-related preclinical models, suggesting that an inhibitor of SYK can have a therapeutic benefit in SLE in view of the pro-inflammatory FcγR-mediated function of SYK in various cells.

1.2 Prior Art 1,6-Naphthyridines are known as SYK-inhibitors. For example U.S. Pat. No. 3,928,367, U.S. Pat. No. 4,017,500, U.S. Pat. No. 4,115,395 and U.S. Pat. No. 4,260,759 describe 5-amino-1,6-naphthyridines with an antifungal and antibacterial activity. Further, WO 9918077 describes 5-piperazinyl-1,6-naphthyridines as serotonin antagonists. Additionally, U.S. Pat. No. 7,321,041 describes substituted 1,6-naphthyridines as SYK-inhibitors, however these 1,6-naphthyridines have a completely different substitution pattern from the compounds according to the invention. Also WO 2011092128 discloses 1,6-naphthyridines which are substituted in 5- and in 7-position.

In WO 2012/167733, WO 2012/167423 and in WO 2012/123312 other naphthryidine derivatives such as pyrido[3,4-b]pyrazines which were also substituted in 5- and in 7-position have been disclosed as SYK-inhibitors.

Additionally, WO 01/83485 discloses substituted imidazopyrimidines and triazolopyrimidines as SYK-inhibitors, whereas WO 2008/113469 discloses substituted imidazo- and triazolopyrimidines as GSK 3β-inhibitors.

Also quinolones are known as SYK-inhibitors. For instance, WO 2006038041 and WO 2013014060 both disclose quinoline-compounds which are substituted in the 5- and 7-position, however the substitution pattern—in particular in the 7-position—is completely different from the one of the compounds of formula 1 of the instant invention.

Additionally also PCT/EP2015055228, PCT/EP2015055237 and PCT/EP2015055242 have been filed (not yet published). Herein also diverse pyrazolyl-substituted heteroaryls are disclosed which are all not substituted at the 3-position of the compounds.

Furthermore, WO2015017610 discloses also pyrazolyl-substituted heteroaryls which all have core modifications compared to the compounds of the instant invention.

Furthermore Thoma et al "Orally bioavailabe SYK inhibitors with activity in a rat PK/PD model", Bioorganic & Medicinal Chemistry Letters (2015)

http://dx.doi.org/10.1016/j.bmcl.2015.08037 (article in press) has been published online wherein SYK-inhibitors with similar benzo- and pyrido-thiazole/isothiazole structures are disclosed. However the most promising compound No. 5 with satisfying SYK-inhibitory capacities has not been further pursued due to the fact that compound No. 5 also inhibited Aurora B (AURB) which severely impaired SYK-selectivity of compound No. 5.

Consequently it was the aim of the instant invention to provide effective SYK-inhibitors with excellent SYK inhibitory capacities which also show a sufficient SYK-selectivity.

Surprisingly it has now been found that the compounds of formulas 1 and 1' of the instant invention are particularly well suitable for the treatment of respiratory complaints, allergic diseases, osteoporosis, gastrointestinal diseases, autoimmune diseases, inflammatory diseases and diseases of the peripheral or central nervous system, particularly for the treatment of asthma, allergic rhinitis, rheumatoid arthritis, allergic dermatitis, lupus erythematosus (SLE) and COPD, in particular because all these compounds of the present invention show the following desired capacities at the same time:

- high SYK inhibition (reflected by "low" $IC_{50}$-values with respect to SYK-inhibition ($IC_{50}$-value <10 nMol in "SYK-inhibition assay" and of $EC_{50}$<150 nMol in "CD63-assay")
- excellent SYK-selectivity that means very low inhibition of other kinases such as Aurora B (reflected by "high" $IC_{50}$-values with respect to inhibition of AURB), as FLT3 (reflected by "high" $IC_{50}$-values with respect to inhibition of FLT3), as GSK3β (reflected by "high" $IC_{50}$-values with respect to inhibition of GSK3β) etc.
- good metabolic stability which can be measured by a low $Q_h$-percentage in human hepatocytes (% $Q_h$<20).

2. DESCRIPTION OF THE INVENTION

The instant invention refers to a compound of formula 1,

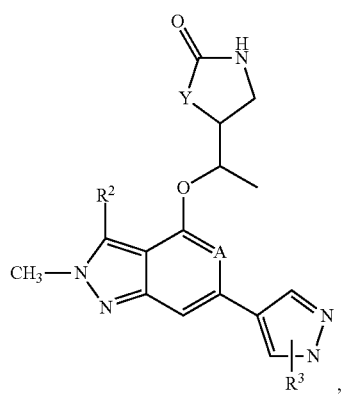

wherein A is either N or CH,
wherein Y is either —O— or $CH_2$,
wherein $R^3$ is a substituent in ortho- or in meta-position of the pyrazolyl-ring of formula 1 and is selected from the group consisting of linear or branched —$C_{1-6}$-alkyl, —$C_{1-6}$-haloalkyl, —$C_{3-6}$-cycloalkyl, —$C_{1-4}$-alkylene-$C_{3-6}$-cycloalkyl, a five- or six-membered monocyclic heterocycle with 1, 2 or three heteroatoms each independently selected from O, S or N, a nine- to 10-membered bicyclic heterocycle with 1, 2 or 3 heteroatoms each independently selected from O, S or N, wherein $R^3$ is optionally substituted by one, two, three or four substituents each independently from each other selected from the group consisting of halogen (F), —$C_{1-3}$-alkyl, oxo, —CN wherein $R^2$ is selected from the group consisting of —$C_{1-3}$-alkyl, —$C_{1-3}$-haloalkyl, F, Br, Cl, and the pharmaceutically acceptable salts of the aforementioned compounds.

In a preferred embodiment the invention relates to the compounds of formula 1'

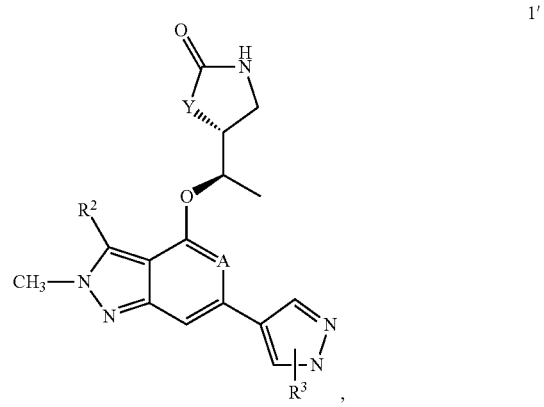

wherein A, Y, $R^2$ and $R^3$ are defined as mentioned above, and the pharmaceutically acceptable salts of the aforementioned compounds.

In further preferred embodiment the invention refers to the compounds of formula or of formula 1',
wherein A is either N or CH
wherein Y is either —O— or $CH_2$,
wherein $R^3$ is a substituent in ortho- or in meta-position of the pyrazolyl-ring of formula 1 and is selected from the group consisting of methyl, ethyl, n-propyl, isopropyl, n-butyl, isobutyl, tert-butyl, —$C_{1-6}$-fluoroalkyl, cyclopropyl, cyclobutyl, cyclopentyl, —$C_{1-2}$-alkylene-$C_{3-6}$-cyclopropyl, —$C_{1-2}$-alkylene-$C_{3-6}$-cyclobutyl, —$C_{1-2}$-alkylene-$C_{3-6}$-cyclopentyl, a five- or six-membered monocyclic heterocycle with 1 oxygen-atom, a 9- to 10-membered bicyclic heterocycle with 1 or 2 heteroatoms each independently selected from O, S or N,
wherein $R^3$ is optionally substituted by one, two, three or four substituents each independently from each other selected from the group consisting of F, Cl, Br, methyl, ethyl, —CN
wherein $R^2$ is selected from the group consisting of methyl, ethyl, isopropyl, —$CF_3$, F, Br, Cl, and the pharmaceutically acceptable salts of the aforementioned compounds.

In another preferred embodiment the invention relates to the aforementioned compounds of formula 1 or of formula 1',
wherein A is either N or CH,
wherein Y is either —O— or —$CH_2$—,
wherein $R^3$ is a substituent in ortho- or in meta-position of the pyrazolyl-ring of formula 1 and is selected from the group consisting of methyl, ethyl, n-propyl, isopropyl, n-butyl, isobutyl, tert-butyl, —$(CH_2)_2$—$CF_3$, —$CH_2$—$CH_2F$, cyclopropyl, cyclobutyl, cyclopentyl, -methylene-$C_{3-6}$-cyclopropyl, tetrahydrofuranyl, tetrahydropyranyl, hexahydrofuropyranyl, wherein R³ is optionally substituted by one, two, three or four substituents each independently from each other selected from the group consisting of F, Cl, Br, methyl, ethyl, —CN wherein R² is selected from the group consisting of methyl and F, and the pharmaceutically acceptable salts of the aforementioned compounds.

In another preferred embodiment the invention refers to the aforementioned compounds of formula 1 or of formula 1', wherein R² is methyl, and the pharmaceutically acceptable salts of the aforementioned compounds.

In a further preferred embodiment the invention relates to the aforementioned compounds of formula 1 or of formula 1', wherein R² is F, and the pharmaceutically acceptable salts of the aforementioned compounds.

In a further preferred embodiment the invention refers to the aforementioned compounds of formula 1 or of formula 1', wherein R³ is a substituent in meta-position of the pyrazolyl-ring of formula L and the pharmaceutically acceptable salts of the aforementioned compounds.

In another preferred embodiment the invention relates to the aforementioned compounds of formula 1 or of formula 1', wherein R³ is a substituent in ortho-position of the pyrazolyl-ring of formula L and the pharmaceutically acceptable salts of the aforementioned compounds.

In a further preferred embodiment the invention refers to the aforementioned compounds of formula 1 or of formula 1', wherein R³ is substituted by one, two, three or four substituents each independently from each other selected from the group consisting of F, methyl and —CN, and the pharmaceutically acceptable salts of the aforementioned compounds.

In another preferred embodiment the invention relates to the aforementioned compounds of formula 1 or of formula 1',
wherein A is either N or CH,
wherein Y is —CH₂—,
wherein R³ is a substituent in ortho- or in meta-position of the pyrazolyl-ring of formula 1 and is selected from the group consisting of methyl, ethyl, n-propyl, isopropyl, n-butyl, isobutyl, tert-butyl, —(CH₂)₂—CF₃, —CH₂—CH₂F,
wherein R³ is optionally substituted by one, two, three or four substituents each independently from each other selected from the group consisting of F, methyl and —CN
and the pharmaceutically acceptable salts of the aforementioned compounds.

In a particularly preferred embodiment the invention relates to the aforementioned compound of formula 1 or of formula 1', which is selected from the group consisting of

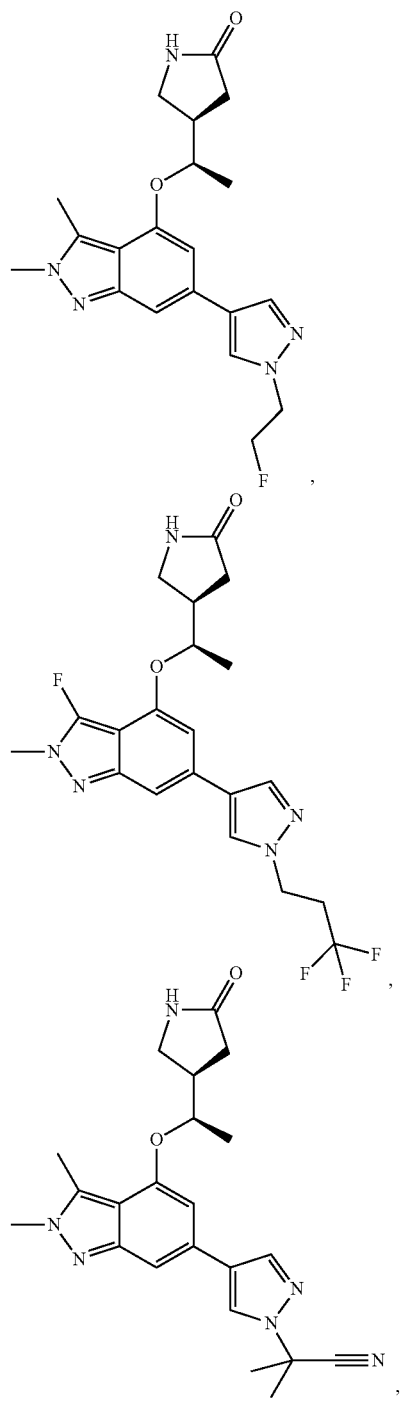

and the pharmaceutically acceptable salts of the aforementioned compounds.

In a further preferred embodiment the invention refers to the aforementioned compounds of formula 1 or of formula 1',
wherein A is either N or CH,
wherein Y is either —O— or CH₂,
wherein R³ is a substituent in ortho- or in meta-position of the pyrazolyl-ring of formula 1 and is selected from the group consisting of isopropyl, isobutyl and t-butyl,
wherein R³ is not further substituted,
and the pharmaceutically acceptable salts of the aforementioned compounds.

In another particularly preferred embodiment the invention relates to the aforementioned compound of formula 1 or of formula 1', which is selected from the group consisting of
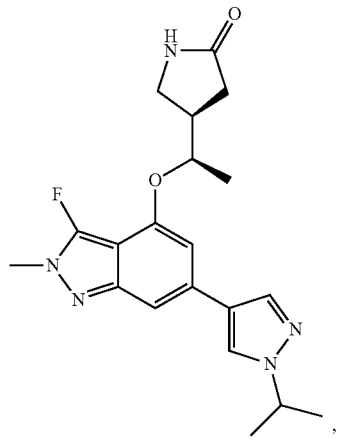
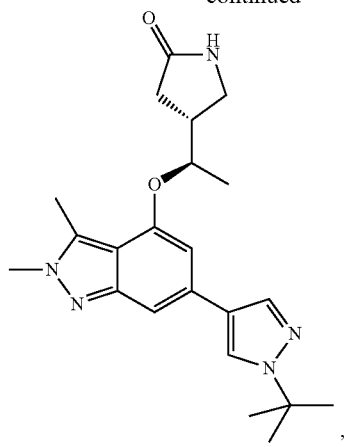
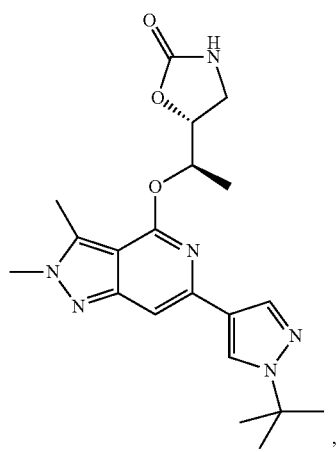
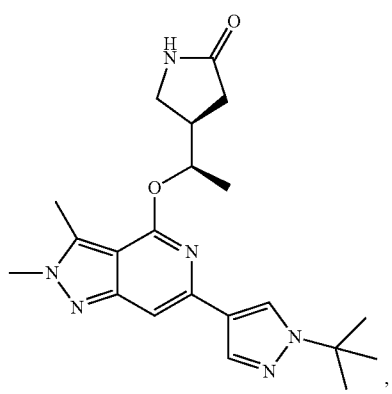
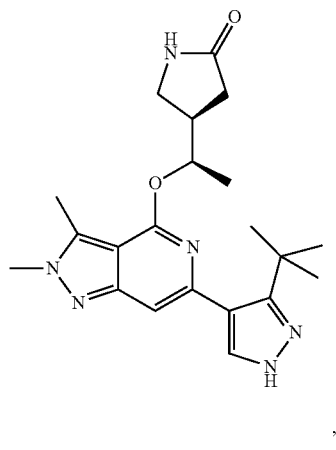
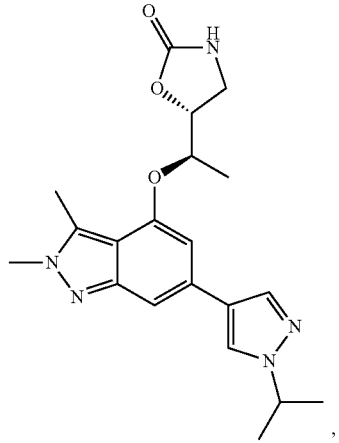

-continued

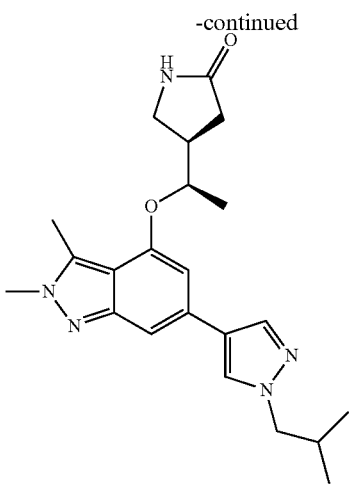

and the pharmaceutically acceptable salts of the aforementioned compounds.

In another particularly preferred embodiment the invention relates to the aforementioned compound of formula 1 or of formula 1', which is

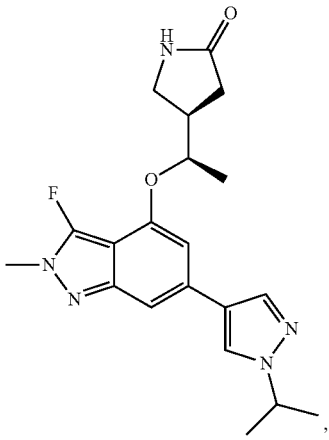 [SMILES: CC(C)n1cc(-c2cc(O[C@H](C)[C@H]3CNC(=O)C3)c3c(F)n(C)nc3c2)cn1]

and the pharmaceutically acceptable salts of the aforementioned compound.

In another particularly preferred embodiment the invention relates to the aforementioned compound of formula 1 or of formula 1', which is

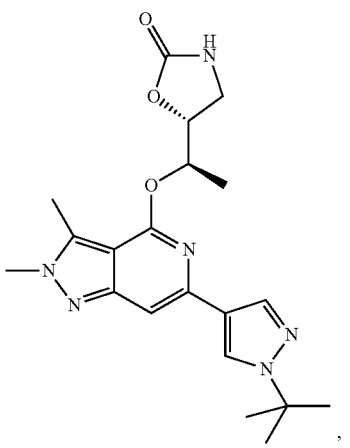 [SMILES: Cc1c2c(O[C@H](C)[C@H]3CNC(=O)O3)nc(-c3cnn(C(C)(C)C)c3)cc2nn1C]

, and the pharmaceutically acceptable salts of the aforementioned compound.

In another particularly preferred embodiment the invention relates to the aforementioned compound of formula 1 or of formula 1', which is

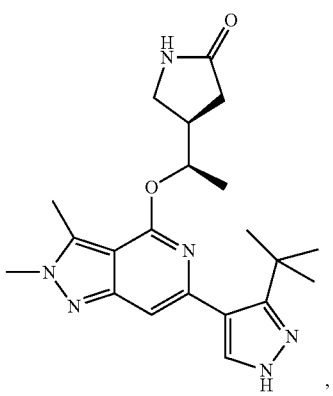 [SMILES: Cc1c2c(O[C@H](C)[C@H]3CNC(=O)C3)nc(-c3c[nH]nc3C(C)(C)C)cc2nn1C]

, and the pharmaceutically acceptable salts of the aforementioned compound.

In another particularly preferred embodiment the invention relates to the aforementioned compound of formula 1 or of formula 1', which is

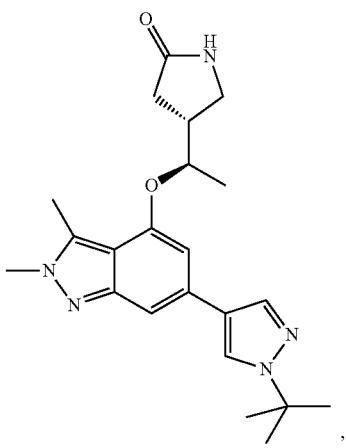 [SMILES: Cc1c2c(O[C@H](C)[C@H]3CNC(=O)C3)cc(-c3cnn(C(C)(C)C)c3)cc2nn1C]

, and the pharmaceutically acceptable salts of the aforementioned compound.

In another particularly preferred embodiment the invention relates to the aforementioned compound of formula 1 or of formula 1', which is

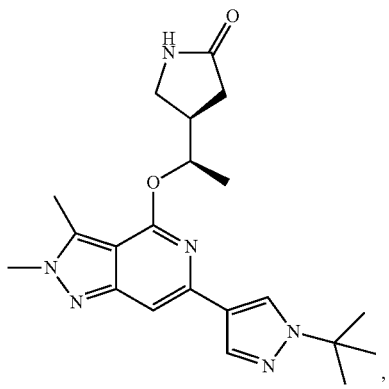 [SMILES: Cc1c2c(O[C@H](C)[C@H]3CNC(=O)C3)nc(-c3cnn(C(C)(C)C)c3)cc2nn1C]

and the pharmaceutically acceptable salts of the aforementioned compound.

In another particularly preferred embodiment the invention relates to the aforementioned compound of formula 1 or of formula 1', which is

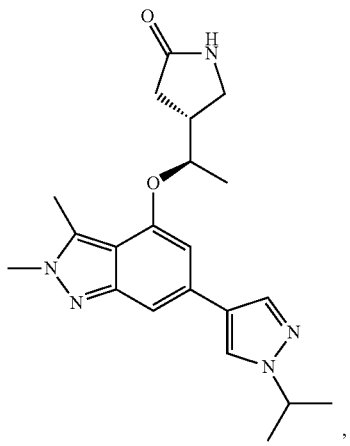 [SMILES: Cc1c2c(O[C@H](C)[C@H]3CNC(=O)C3)cc(-c3cnn(C(C)C)c3)cc2nn1C]

and the pharmaceutically acceptable salts of the aforementioned compound.

In another particularly preferred embodiment the invention relates to the aforementioned compound of formula 1 or of formula 1', which is

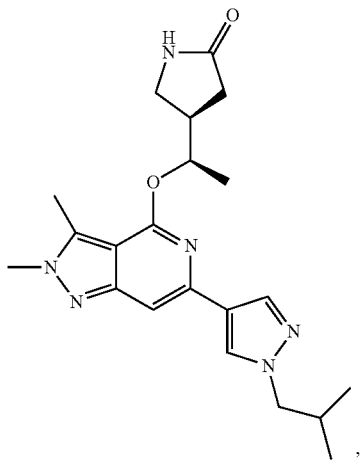 [SMILES: Cc1c2c(O[C@H](C)[C@H]3CNC(=O)C3)nc(-c3cnn(CC(C)C)c3)cc2nn1C]

and the pharmaceutically acceptable salts of the aforementioned compound.

In another particularly preferred embodiment the invention relates to the aforementioned compound of formula 1 or of formula 1', wherein wherein A is either N or CH, wherein Y is —CH$_2$—, wherein R$^3$ is a substituent in ortho- or in meta-position of the pyrazolyl-ring of formula 1 and is selected from the group consisting of cyclopropyl, cyclobutyl, cyclopentyl, -methylene-C$_{3-6}$-cyclopropyl, tetrahydrofuranyl, tetrahydropyranyl, hexahydrofuropyranyl, wherein R$^3$ is optionally substituted by one, two, three or four substituents each independently from each other selected from the group consisting of F, methyl and —CN and the pharmaceutically acceptable salts of the aforementioned compounds.

In another particularly preferred embodiment the invention relates to the aforementioned compound of formula 1 or of formula 1', which is selected from the group consisting of

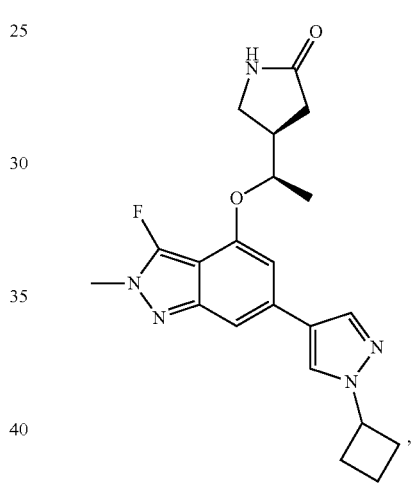

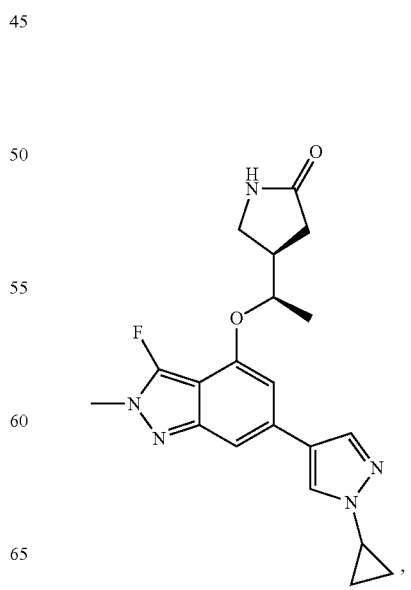

-continued
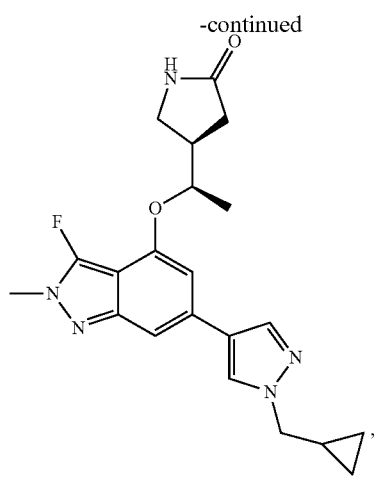
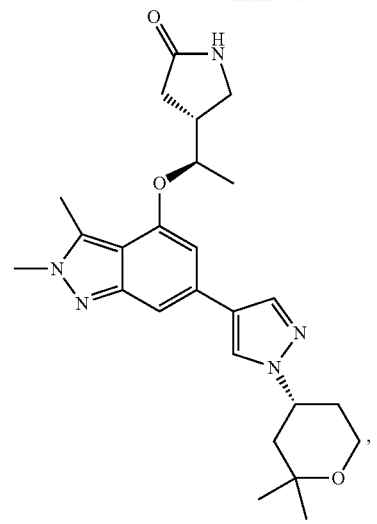
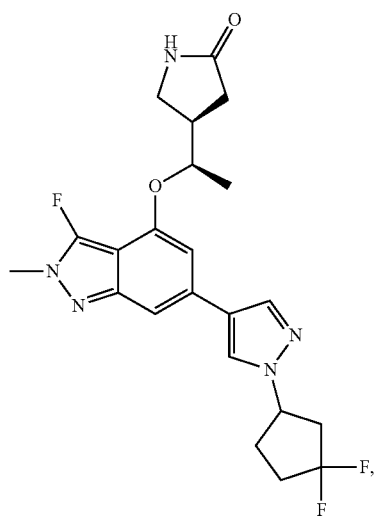
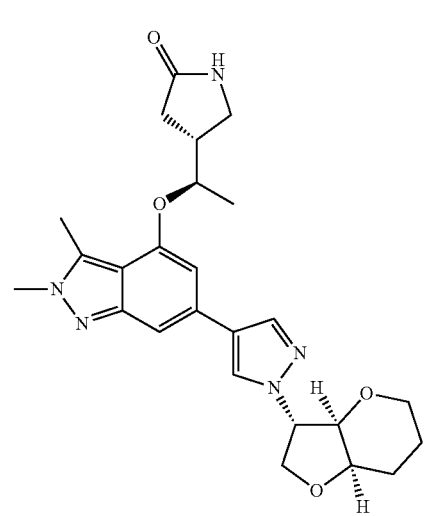
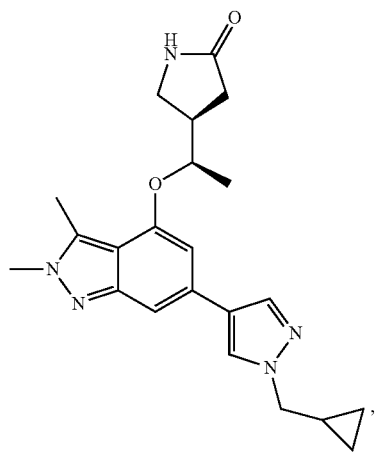
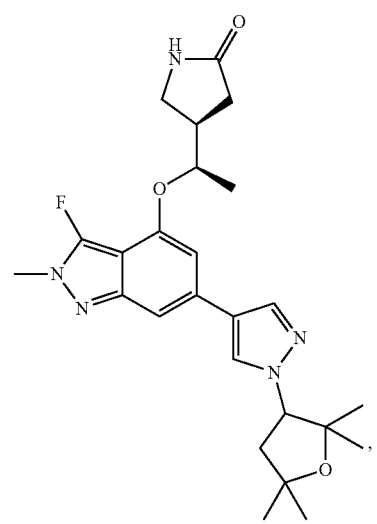

17
-continued

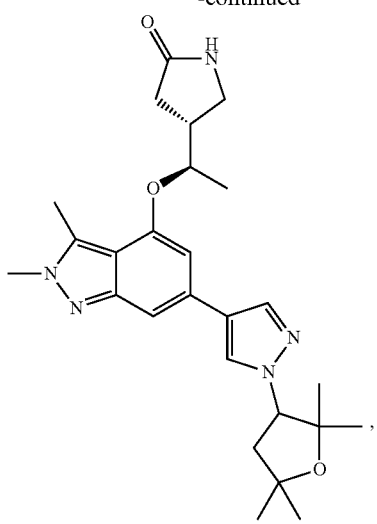

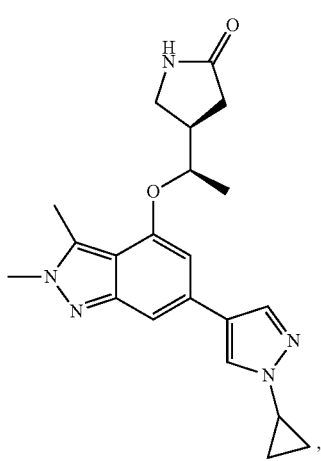

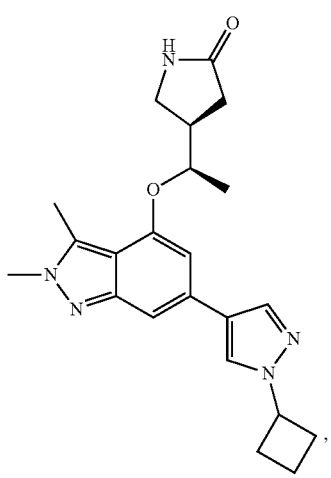

18
-continued

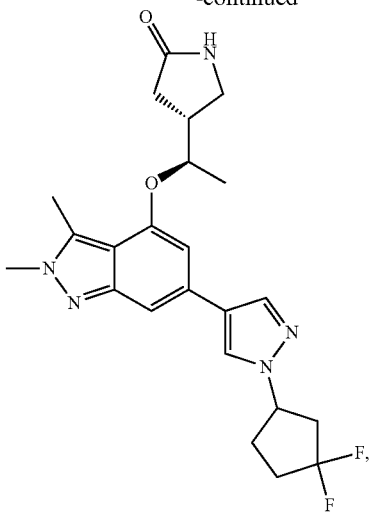

and the pharmaceutically acceptable salts of the aforementioned compounds.

In another particularly preferred embodiment the invention relates to the aforementioned compound of formula 1 or of formula 1', which is

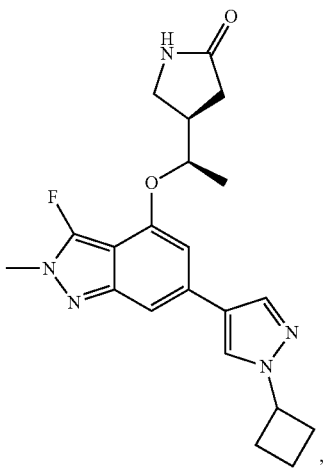 [SMILES: C[C@@H](Oc1cc(-c2cnn(C3CCC3)c2)cc2nn(C)c(F)c12)[C@H]1CNC(=O)C1]

and the pharmaceutically acceptable salts of the aforementioned compounds.

In another particularly preferred embodiment the invention relates to the aforementioned compound of formula 1 or of formula 1', which is

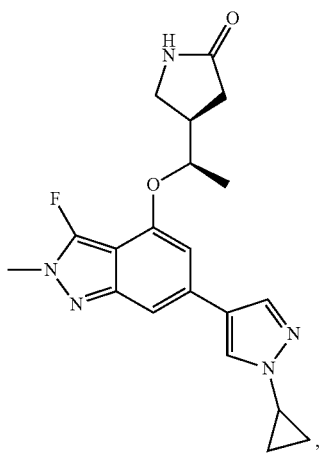 [SMILES: C[C@@H](Oc1cc(-c2cnn(C3CC3)c2)cc2nn(C)c(F)c12)[C@H]1CNC(=O)C1]

and the pharmaceutically acceptable salts of the aforementioned compounds.

In another particularly preferred embodiment the invention relates to the aforementioned compound of formula 1 or of formula 1', which is

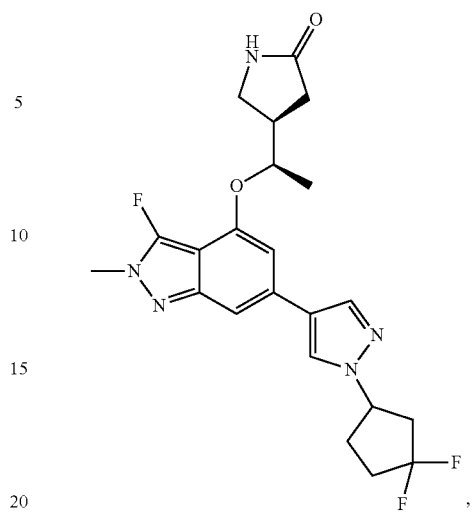

and the pharmaceutically acceptable salts of the aforementioned compounds.

In another particularly preferred embodiment the invention relates to the aforementioned compound of formula 1 or of formula 1', which is

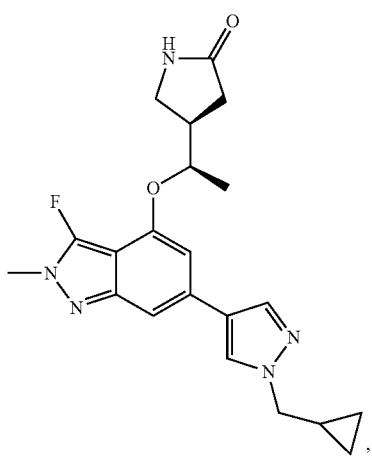 [SMILES: C[C@@H](Oc1cc(-c2cnn(CC3CC3)c2)cc2nn(C)c(F)c12)[C@H]1CNC(=O)C1]

and the pharmaceutically acceptable salts of the aforementioned compounds.

In another particularly preferred embodiment the invention relates to the aforementioned compound of formula 1 or of formula 1', which is

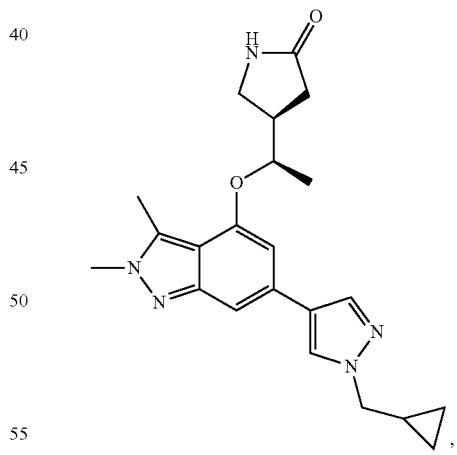

and the pharmaceutically acceptable salts of the aforementioned compounds.

In another particularly preferred embodiment the invention relates to the aforementioned compound of formula 1 or of formula 1', which is

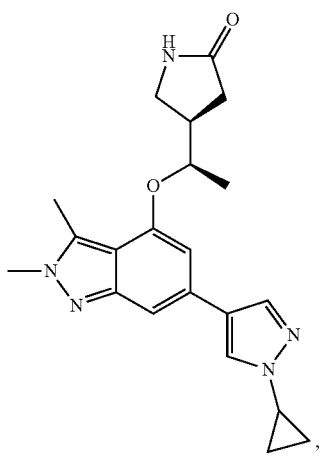

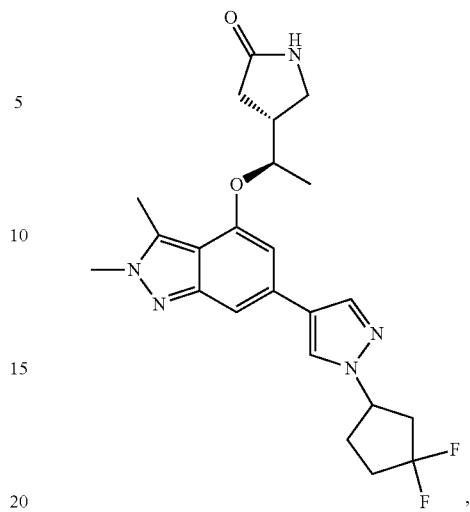

and the pharmaceutically acceptable salts of the aforementioned compounds.

In another particularly preferred embodiment the invention relates to the aforementioned compound of formula 1 or of formula 1', which is

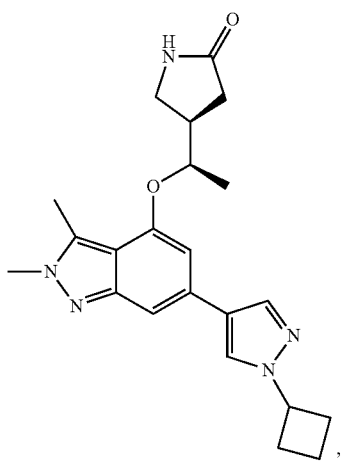 [SMILES: Cc1c2c(O[C@H](C)[C@H]3CNC(=O)C3)cc(-c3cnn(C4CCC4)c3)cc2nn1C]

and the pharmaceutically acceptable salts of the aforementioned compounds.

In another particularly preferred embodiment the invention relates to the aforementioned compound of formula 1 or of formula 1', which is and the pharmaceutically acceptable salts of the aforementioned compounds.

In a further preferred embodiment the invention relates to the aforementioned compounds for the treatment of a disease which can be treated by inhibition of the SYK enzyme.

In another preferred embodiment the invention relates to the aforementioned compounds for the treatment of a disease selected from the group consisting of allergic rhinitis, asthma, COPD, adult respiratory distress syndrome, bronchitis, B-cell lymphoma, dermatitis and contact dermatitis, allergic dermatitis, allergic rhinoconjunctivitis, rheumatoid arthritis, anti-phospholipid syndrome, Berger's disease, Evans's syndrome, ulcerative colitis, allergic antibody-based glomerulonephritis, granulocytopenia, Goodpasture's syndrome, hepatitis, Henoch-Schönlein purpura, hypersensitivity vasculitis, immunohaemolytic anaemia, autoimmune haemolytic anemia, idiopathic thrombocytopenic purpura, Kawasaki syndrome, allergic conjunctivitis, lupus erythematodes, lupus nephritis, capsule cell lymphoma, neutropenia, non-familial lateral sclerosis, artheriosclerosis, Crohn's disease, multiple sclerosis, myasthenia gravis, osteoporosis, osteolytic diseases, osteopenia, psoriasis, Sjögren's syndrome, sclerodermy, T-cell lymphoma, urticaria/angiooedema, Wegener's granulomatosis, coeliac disease Waldenstroem macroglubulinemia, systemic sclerosis (SSc), malaria and dengue.

In a further preferred embodiment the invention relates to the aforementioned compounds for the treatment of a disease selected from the group consisting of asthma, COPD, allergic rhinitis, adult respiratory distress syndrome, bronchitis, allergic dermatitis, contact dermatitis, idiopathic thrombocytopenic purpura, rheumatoid arthritis, lupus erythematodes, lupus nephritis, systemic sclerosis (SSc) and allergic rhinoconjunctivitis.

In another preferred embodiment the invention relates to the aforementioned compound for the treatment of a disease selected from the group consisting of asthma, COPD, allergic rhinitis, idiopathic thrombocytopenic purpura, allergic dermatitis, lupus erythematodes, lupus nephritis and rheumatoid arthritis.

In a further preferred embodiment the invention relates to pharmaceutical formulations, which contain one or more of the aforementioned compounds and a pharmaceutically acceptable excipient.

In another preferred embodiment the invention relates to pharmaceutical formulations, which contain one or more of the aforementioned compounds in combination with an active substance selected from the group consisting of anticholinergics, betamimetics, corticosteroids, PDE4-inhibitors, EGFR-inhibitors, LTD4-antagonists, CCR3-inhibitors, iNOS-inhibitors, CRTH2-antagonists, triple kinase inhibitors against PDGFR, FGFR and VEGFR, HMG-CoA reductase inhibitors and NSAIDs.

In another preferred embodiment the invention relates to an intermediate compound selected from the group consisting of formula 7

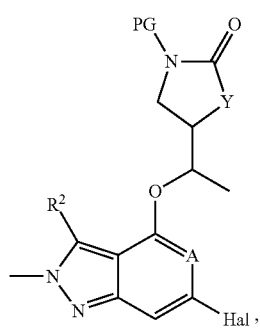

of formula 8

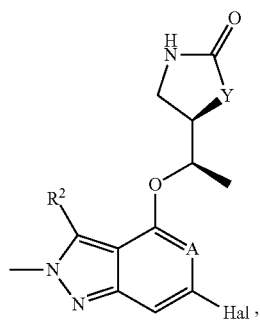

of formula 11

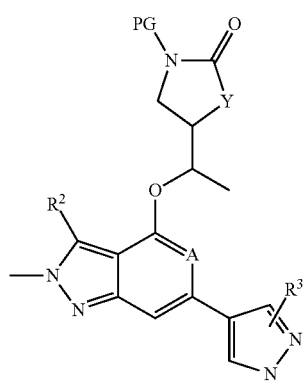

wherein R² is F or methyl,
wherein Y is either —O— or CH₂,
and wherein R³ is defined as in one of claims 1 to 3 and
wherein Hal is Cl or Br and wherein PG is a protecting group selected from the group consisting of benzyl, 1-phenylethyl, 1-(4-methoxyphenyl)ethyl.

In another preferred embodiment the invention relates to an intermediate compound selected from the group consisting of

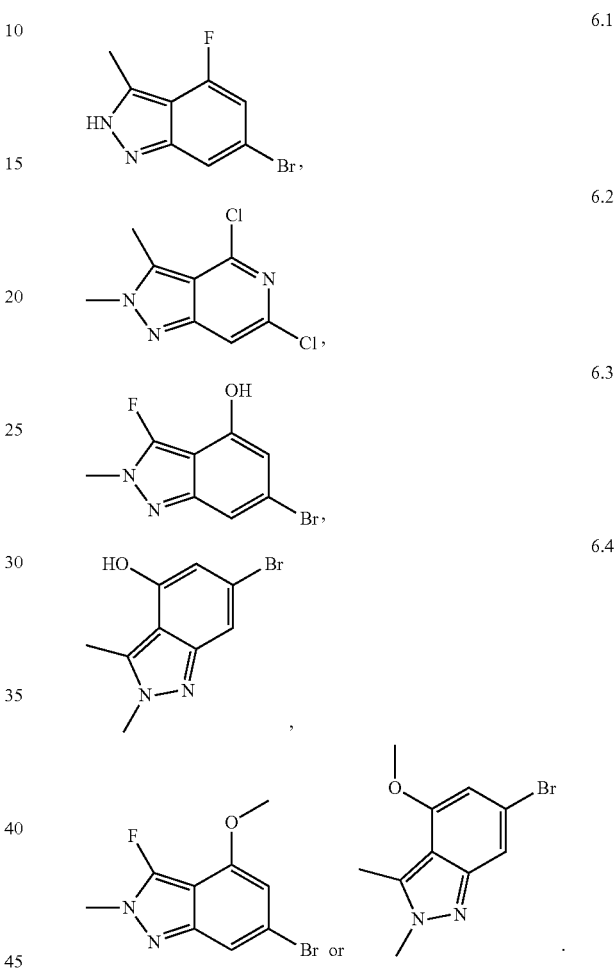

3. TERMS AND DEFINITIONS USED

Unless stated otherwise, all the substituents are independent of one another. If for example a number of $C_{1-6}$-alkyl groups are possible substituents at a group, in the case of three substituents, for example, $C_{1-6}$-alkyl could represent, independently of one another, a methyl, an n-propyl and a tert-butyl.

Within the scope of this application, in the definition of possible substituents, these may also be presented in the form of a structural formula. An asterisk (*) in the structural formula of the substituent is to be understood as being the linking point to the rest of the molecule. Mor3eover, the atom of the substituent following the linking point is understood as being the atom in position number 1. Thus for example the groups N-piperidinyl (I), 4-piperidinyl (II), 2-tolyl (III), 3-tolyl (IV) and 4-tolyl (V) are represented as follows:

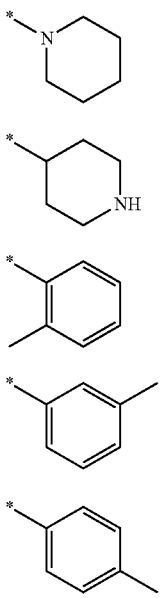

I

II

III

IV

V

If there is no asterisk (*) in the structural formula of the substituent, each hydrogen atom may be removed at the substituent and the valency thus freed may serve as a binding site to the rest of a molecule. Thus, for example, VI

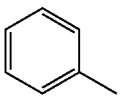

VI may represent 2-tolyl, 3-tolyl, 4-tolyl and benzyl.

Alternatively to the * within the scope of this application $X_1$ is also understood as being the linking point of the group $R^1$ to the structure of formula 1 and $X_2$ as being the linking point of the group $R^2$ to the structure of formula 1.

By the term "$C_{1-6}$-alkyl" (including those which are part of other groups) are meant branched and unbranched alkyl groups with 1 to 6 carbon atoms and by the term "$C_{1-3}$-alkyl" are meant branched and unbranched alkyl groups with 1 to 3 carbon atoms. "$C_{1-4}$-alkyl" accordingly denotes branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc., may also optionally be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples of these include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1, 3-dimethylpropylene or hexylene. Unless stated otherwise, the definitions propylene, butylene, pentylene and hexylene include all the possible isomeric forms of the groups in question with the same number of carbons. Thus, for example, propyl includes also 1-methylethylene and butylene includes 1-methylpropylene, 1,1-dimethylethylene, 1,2-dimethylethylene.

If the carbon chain is substituted by a group which together with one or two carbon atoms of the alkylene chain forms a carbocyclic ring with 3, 5 or 6 carbon atoms, this includes, inter alia, the following examples of the rings:

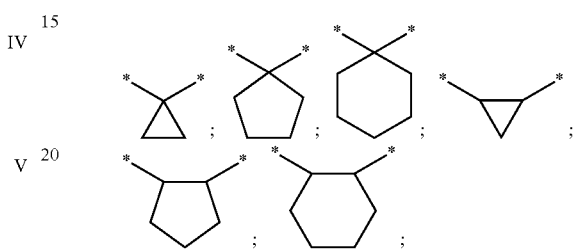

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples of these include: ethenylene, propenylene, 1-methylethenylene, butenylene, 1-methylpropenylene, 1,1-dimethylethenylene, 1, 2-dimethylethenylene, pentenylene, 1,1-dimethylpropenylene, 2,2-dimethylpropenylene, 1, 2-dimethylpropenylene, 1, 3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1, 1-dimethylethenylene, 1, 2-dimethylethenylene.

By the term "aryl" (including those which are part of other groups) are meant aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "aryl-$C_{1-6}$-alkylene" (including those which are part of other groups) are meant branched and unbranched alkylene groups with 1 to 6 carbon atoms, which are substituted by an aromatic ring system with 6 or 10 carbon atoms. Examples include: benzyl, 1- or 2-phenylethyl or 1- or 2-naphthylethyl. Unless otherwise stated, the aromatic groups may be substituted by one or more groups selected from among methyl, ethyl, iso-propyl, tert-butyl, hydroxy, fluorine, chlorine, bromine and iodine.

By the term "heteroaryl-$C_{1-6}$-alkylene" (including those which are part of other groups) are meant—even though they are already included under "aryl-$C_{1-6}$-alkylene"— branched and unbranched alkylene groups with 1 to 6 carbon atoms, which are substituted by a heteroaryl.

If not specifically defined otherwise, a heteroaryl of this kind includes five- or six-membered heterocyclic aromatic groups or 5-10-membered, bicyclic heteroaryl rings which may contain one, two, three or four heteroatoms selected from among oxygen, sulphur and nitrogen, and contain so many conjugated double bonds that an aromatic system is formed. The following are examples of five- or six-membered heterocyclic aromatic groups or bicyclic heteroaryl rings:

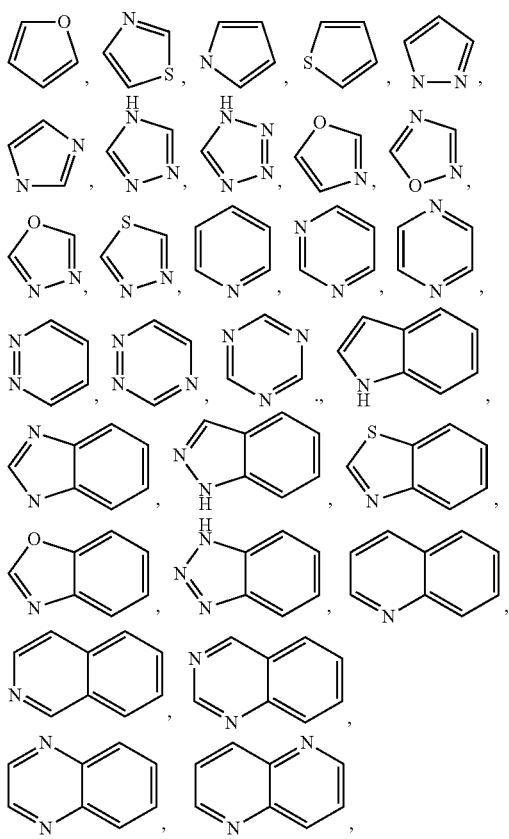

Unless otherwise stated, these heteroaryls may be substituted by one or more groups selected from among methyl, ethyl, iso-propyl, tert-butyl, hydroxy, fluorine, chlorine, bromine and iodine.

The following are examples of heteroaryl-$C_{1-6}$-alkylenes:

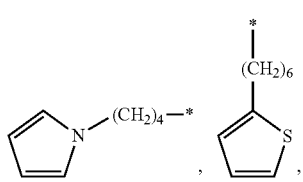

-continued

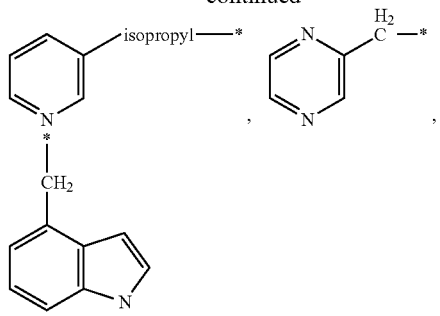

By the term "$C_{1-6}$-haloalkyl" (including those which are part by of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "$C_{3-7}$-cycloalkyl" (including those which are part of other groups) are meant cyclic alkyl groups with 3 to 7 carbon atoms, if not specifically defined otherwise. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

If not specifically defined otherwise, by the term "$C_{3-10}$-cycloalkyl" are also meant monocyclic alkyl groups with 3 to 7 carbon atoms and also bicyclic alkyl groups with 7 to 10 carbon atoms, or monocyclic alkyl groups which are bridged by at least one $C_{1-3}$-carbon bridge.

By the term "heterocyclic rings" or "heterocycle" are meant, unless stated otherwise, five-, six- or seven-membered, saturated, partially saturated or unsaturated heterocyclic rings which may contain one, two or three heteroatoms, selected from among oxygen, sulphur and nitrogen, while the ring may be linked to the molecule through a carbon atom or through a nitrogen atom, if there is one. Although included by the term "heterocyclic rings" or "heterocycles", the term "saturated heterocyclic ring" refers to five-, six- or seven-membered saturated rings. Examples include:

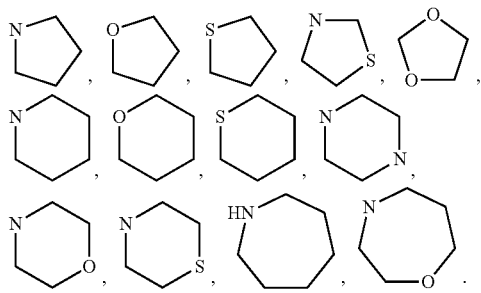

Although included by the term "heterocyclic rings" or "heterocyclic group", the term "partially saturated heterocyclic group" refers to five-, six- or seven-membered partially saturated rings which contain one or two double bonds, without so many double bonds being produced that an aromatic system is formed, unless specifically defined otherwise. Examples include:

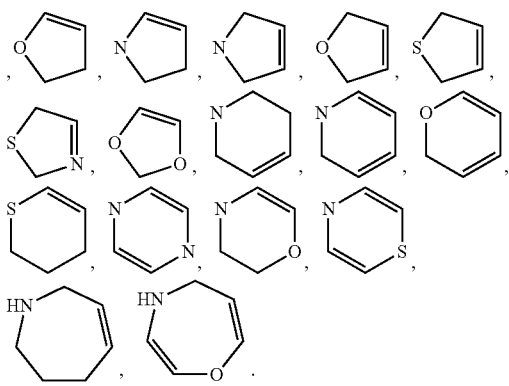

Although included by the term "heterocyclic rings" or "heterocycles", the term "heterocyclic aromatic rings", "unsaturated heterocyclic group" or "heteroaryl" refers to five- or six-membered heterocyclic aromatic groups or 5-10-membered, bicyclic heteroaryl rings which may contain one, two, three or four heteroatoms, selected from among oxygen, sulphur and nitrogen, and contain so many conjugated double bonds that an aromatic system is formed, unless not specifically defined otherwise. Examples of five- or six-membered heterocyclic aromatic groups include:

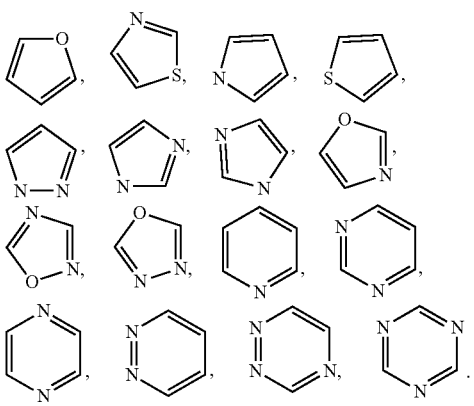

Unless otherwise mentioned, a heterocyclic ring (or heterocycle) may be provided with a keto group. Examples include:

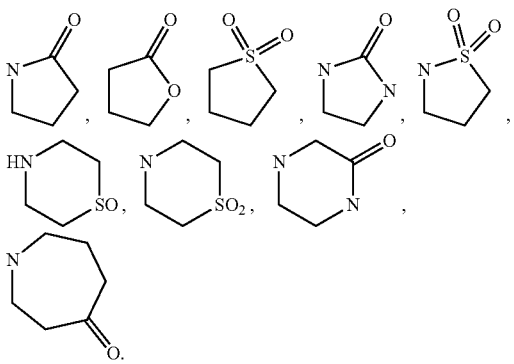

Although covered by the term "cycloalkyl", the term "bicyclic cycloalkyls" generally denotes eight-, nine- or ten-membered bicyclic carbon rings. Examples include

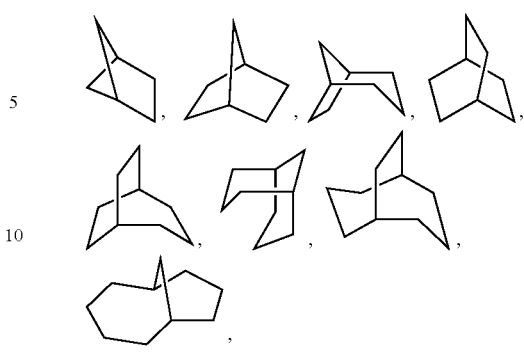

Although already included by the term "heterocycle", the term "bicyclic heterocycles" generally denotes eight-, nine- or ten-membered bicyclic rings which may contain one or more heteroatoms, preferably 1-4, more preferably 1-3, even more preferably 1-2, particularly one heteroatom, selected from among oxygen, sulphur and nitrogen, unless not specifically defined otherwise. The ring may be linked to the molecule through a carbon atom of the ring or through a nitrogen atom of the ring, if there is one. Examples include:

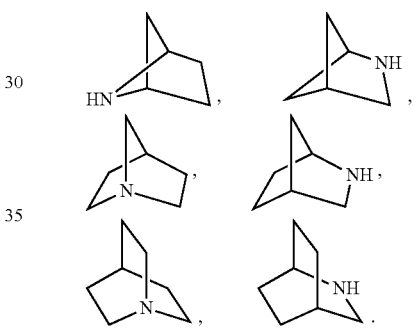

Although already included by the term "aryl", the term "bicyclic aryl" denotes a 5-10 membered, bicyclic aryl ring which contains sufficient conjugated double bonds to form an aromatic system. One example of a bicyclic aryl is naphthyl.

Although already included under "heteroaryl", the term "bicyclic heteroaryl" denotes a 5-10 membered, bicyclic heteroaryl ring which may contain one, two, three or four heteroatoms, selected from among oxygen, sulphur and nitrogen, and contains sufficient conjugated double bonds to form an aromatic system, unless specifically defined otherwise.

Although included by the term "bicyclic cycloalkyls" or "bicyclic aryl", the term "fused cycloalkyl" or "fused aryl" denotes bicyclic rings wherein the bridge separating the rings denotes a direct single bond. The following are examples of a fused, bicyclic cycloalkyl:

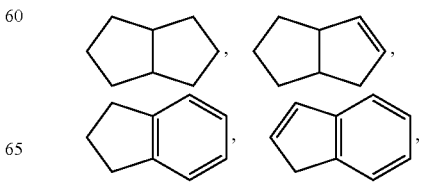

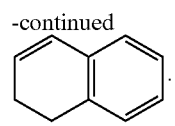

Although included by the term "bicyclic heterocycles" or "bicyclic heteroaryls", the term "fused bicyclic heterocycles" of "fused bicyclic heteroaryls" denotes bicyclic 5-10 membered heterorings which contain one, two, three or four heteroatoms, selected from among oxygen, sulphur and nitrogen and wherein the bridge separating the rings denotes a direct single bond. The "fused bicyclic heteroaryls" moreover contain sufficient conjugated double bonds to form an aromatic system. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

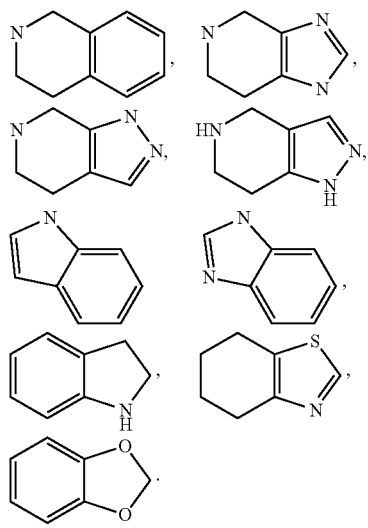

"Halogen" within the scope of the present invention denotes fluorine, chlorine, bromine or iodine. Unless stated to the contrary, fluorine, chlorine and bromine are regarded as preferred halogens.

Compounds of general formulas 1 or 1' may have acid groups, mainly carboxyl groups, and/or basic groups such as e.g. amino functions. Compounds of general formulas 1 or 1' may therefore be present as internal salts, as salts with pharmaceutically usable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically usable bases such as alkali metal or alkaline earth metal hydroxides or carbonates, zinc or ammonium hydroxides or organic amines such as e.g. diethylamine, triethylamine, triethanolamine, inter alia.

As mentioned previously, the compounds of formulas 1 or 1' may be converted into the salts thereof, particularly for pharmaceutical use into the physiologically and pharmacologically acceptable salts thereof. These salts may be present on the one hand as physiologically and pharmacologically acceptable acid addition salts of the compounds of formula 1 with inorganic or organic acids. On the other hand, the compound of formulas 1 or 1' when R is hydrogen may be converted by reaction with inorganic bases into physiologically and pharmacologically acceptable salts with alkali or alkaline earth metal cations as counter-ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. To prepare the alkali and alkaline earth metal salts of the compounds of formulas 1 or 1' wherein R denotes hydrogen, it is preferable to use the alkali and alkaline earth metal hydroxides and hydrides, of which the hydroxides and hydrides of the alkali metals, particularly sodium and potassium, are preferred, while sodium and potassium hydroxide are particularly preferred.

The compounds of general formulas 1 or 1' may optionally be converted into the salts thereof, particularly for pharmaceutical use into the pharmacologically acceptable acid addition salts with an inorganic or organic acid. Examples of suitable acids for this purpose include succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

The invention relates to the compounds of formula 1 or 1' in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The compounds of formula 1 or 1' according to the invention may optionally be present as racemates, but may also be obtained as pure enantiomers, i.e. in the (R) or (S) form. Preferred are the compounds with the specific stereochemistry of formula 1'.

The invention relates to the compounds in question, optionally in the form of the individual optical isomers, diastereomers, mixtures of diastereomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The invention relates to the respective compounds of formulas 1 or 1' in the form of the pharmacologically acceptable salts thereof. These pharmacologically acceptable salts of the compounds of formulas 1 or 1' may also be present in the form of their respective hydrates (e.g. Monohydrates, dihydrates, etc.) as well as in the form of their respective solvates.

By a hydrate of the compound according to the formulas 1 or 1' is meant, for the purposes of the invention, a crystalline salt of the compound according to formulas 1 or 1', containing water of crystallisation.

By a solvate of the compound according to formulas 1 or 1' is meant, for the purposes of the invention, a crystalline salt of the compound according to formulas 1 or 1', which 33
contains solvent molecules (e.g. Ethanol, methanol etc) in the crystal lattice.
The skilled man will be familiar with the standard methods of obtaining hydrates and solvates (e.g. recrystallisation from the corresponding solvent or from water).
34
4. METHODS OF PREPARATION
The Examples according to the invention were prepared as shown in Schemes 1, 2 or 3.
Scheme 1:
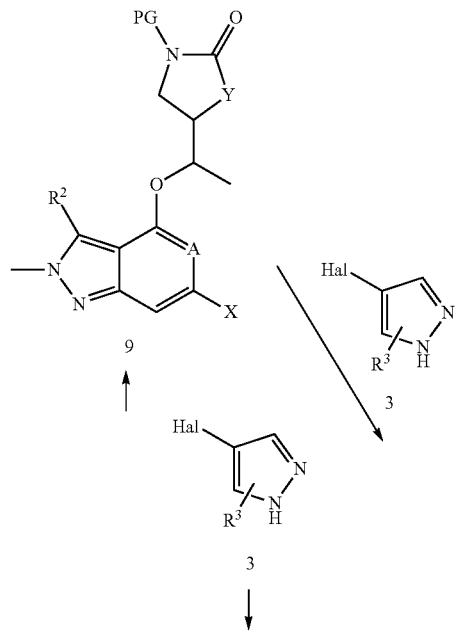
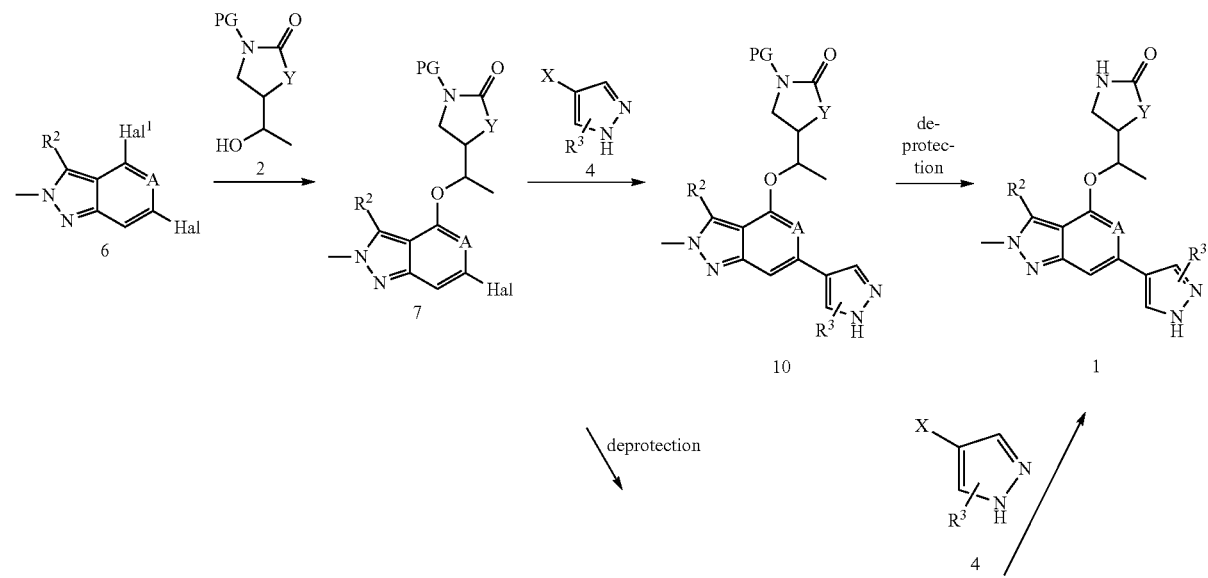

-continued
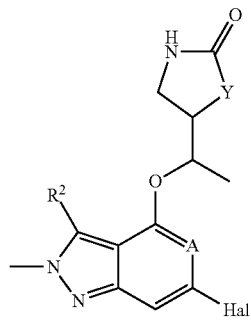
8
Building blocks applied in Scheme 1
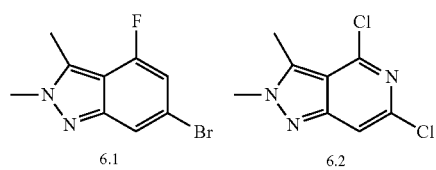
6.1    6.2
A is N, CH
Y is O, OH$_2$
Hal is Br or Cl
Hal$^1$ is Cl, F
with X being —B(OH)$_2$, -boronic acid pinacolester
PG is protecting group (e.g. benzyl, 1-phenylethyl, 1-(4-methoxyphenyl)ethyl)
and R$^2$ and R$^3$ are as herein before defined.
Scheme 2:
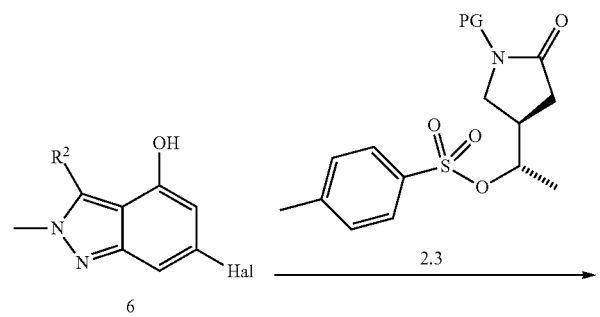
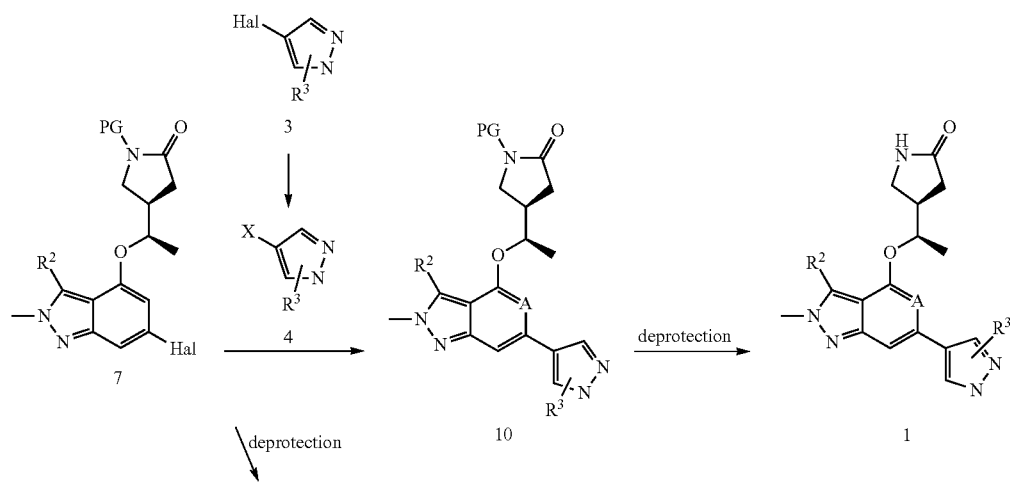

37
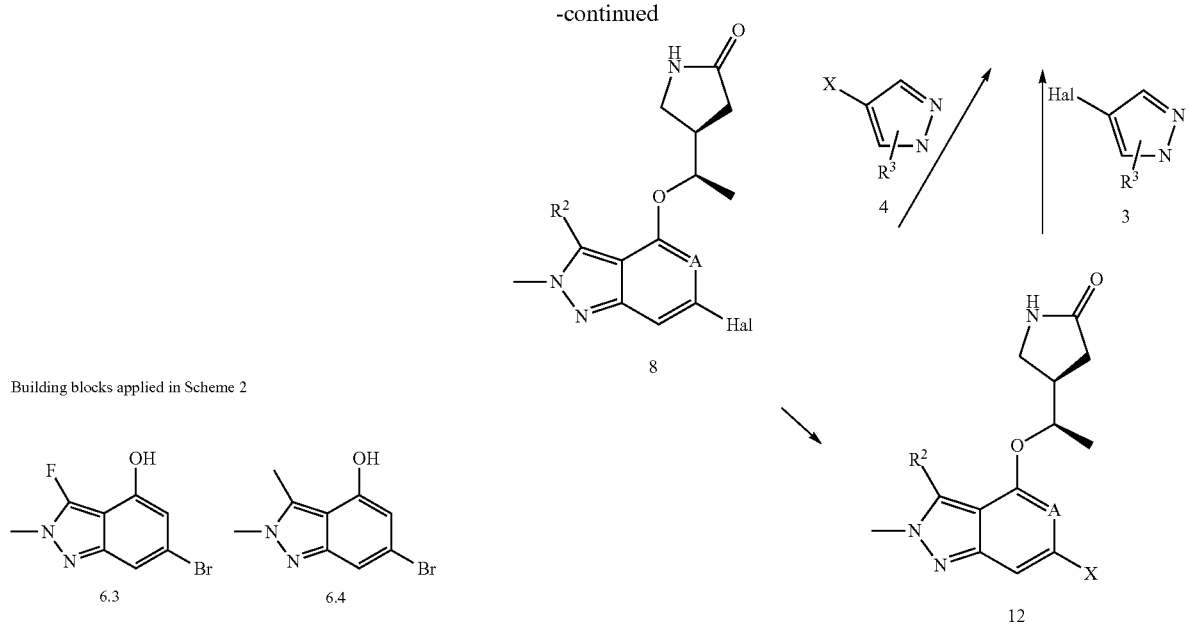
Building blocks applied in Scheme 2
Hal is Br or Cl
with X being —B(OH)$_2$, -boronic acid pinacolester
PG is protecting group (e.g. benzyl, 1-phenylethyl, 1-(4-methoxyphenyl)ethyl)
and R$^2$ and R$^3$ are as herein before defined.
Scheme 3
38
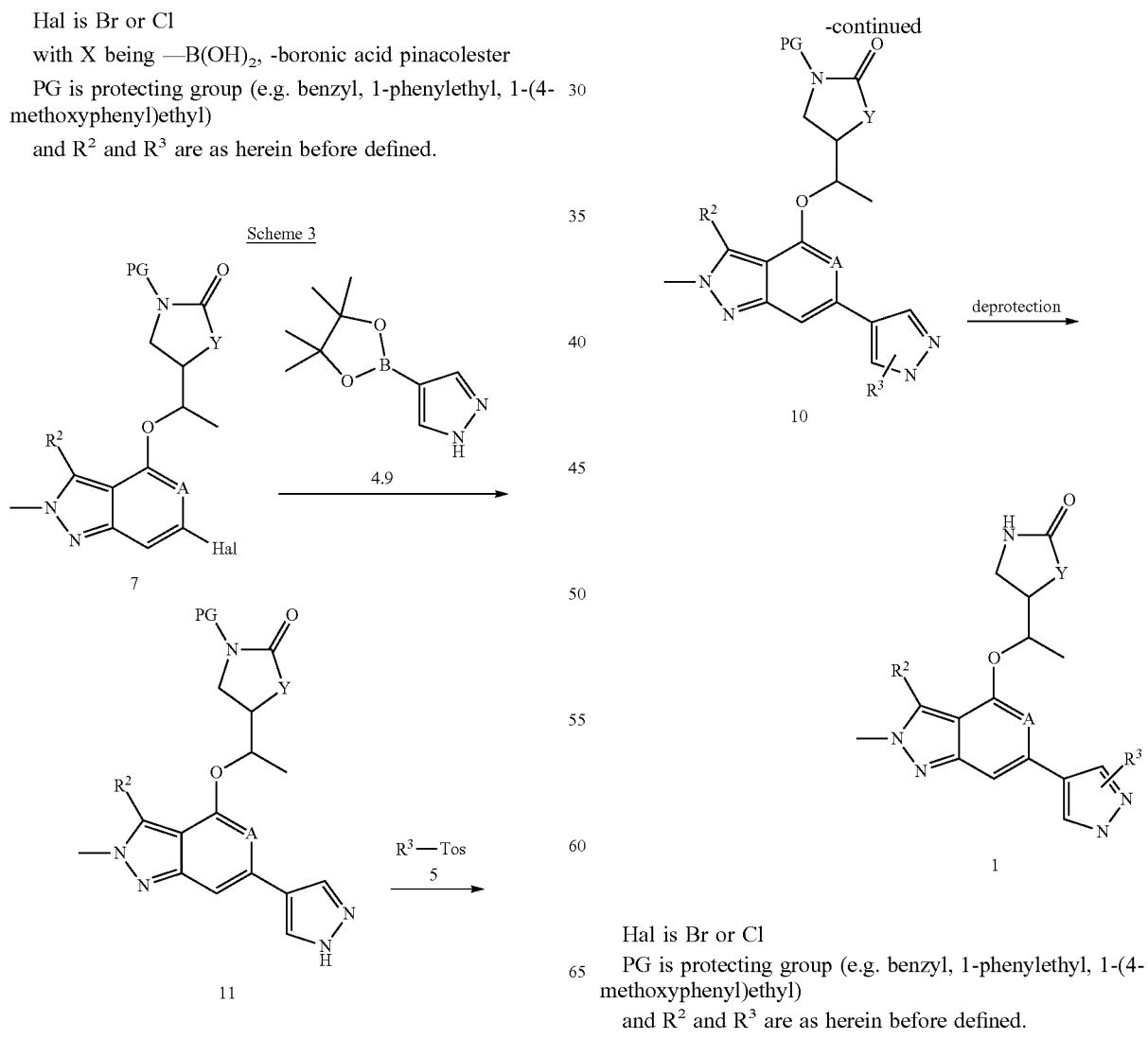
Hal is Br or Cl
PG is protecting group (e.g. benzyl, 1-phenylethyl, 1-(4-methoxyphenyl)ethyl)
and R$^2$ and R$^3$ are as herein before defined.

4.1. Starting Materials of Formula 2, 3, 4, 5, and 6
4.1.1. Synthesis of Compounds of Formula 2 from Scheme 1, 2 and 3

Synthesis of Synthesis of (R)-4-[(R)-1-Hydroxyethyl]-1-[(S)-1-(4-methoxyphenyl)-ethyl]-pyrrolidin-2-one (2.1) for Examples 1, 2, 4-12, 14, 15, 17, 19 and (R)-4-[(S)-1-Hydroxyethyl]-1-[(S)-1-(4-methoxyphenyl)-ethyl]-pyrrolidin-2-one (2.2 for Examples 13, 16, 18, 20, 21, 22

Step 1: Synthesis of (1'R,3R/S)-1-(1'-(4-Methoxyphenylethyl)-5-oxo-3-pyrrolidine carboxylic Acid (Mixture of Diastereoisomers)

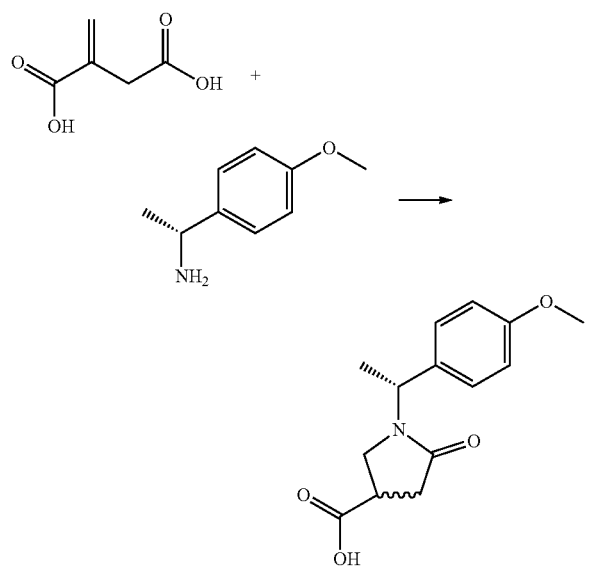

A suspension of 100 g of (R)-1-(4-methoxy-phenyl)-ethylamine and 95 g itaconic acid in 0.5 L 1-methyl-2-pyrrolidinone was heated to 80° C. for 1 hour. The solution was stirred for additional 4 hours at 120° C. The reaction mixture was cooled to 25° C. and poured into 1.5 L of demineralized water. The precipitate was filtered, washed with demineralized water and dried at 50° C.

Yield: 195 g (quantitative yield) solid as a Mixture of Diastereoisomers

Analysis (method G): $R_t$: 2.6 min and 2.7 min, (M+H)$^+$: 264

Step 2: Synthesis of (R/S)—N-Methoxy-5-oxo-1-[(S)-1-(4-methoxyphenyl)-ethyl]-pyrrolidine-3-carboxamide as a Mixture of Diastereoisomers

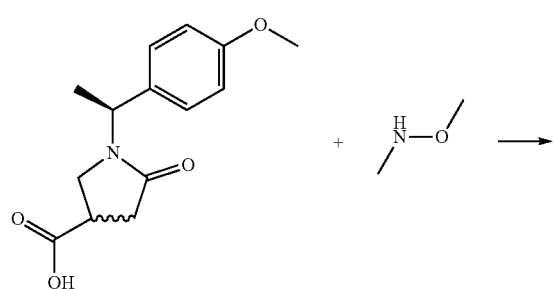

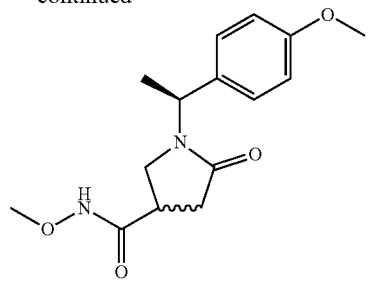

260 g of 1,1'-carbonyldiimidazole (CDI) were added to a solution of 285 g (1'R,3R/S)-1-(1'-(4-methoxyphenylethyl)-5-oxo-3-pyrrolidine carboxylic acid (mixture of diastereoisomers) in 1.4 L 2-methyltetrahydrofuran at 20° C. The suspension was stirred at 20° C. for 80 minutes. 235 mL ethyldiisopropylamine (DIPEA) and 130 g of N,O-dimethylhydroxylamine hydrochloride were added. The suspension was stirred for 3 hours at 20° C. Under cooling 850 mL 4M hydrochloric acid was added. The organic phase was separated and washed two times with 500 mL 1 N hydrochloric acid. The aqueous phase was reextracted two times with 500 mL ethyl acetate. The combined organic phases were dried over sodium sulfate. After filtration the solvent was evaporated under reduced pressure.

Yield: 271 g (82% of theory) of (R/S)—N-Methoxy-5-oxo-1-[(S)-1-(4-methoxyphenyl)-ethyl]-pyrrolidine-3-carboxamide (mixture of diastereoisomers) as an oil.

Analysis (method H): $R_t$: 11.1 min (41 area %) and 13.8 min (59 area %), (M+H)$^+$: 307

Step 3: Synthesis of (R/S)-4-Acetyl-1-[(S)-1-(4-methoxyphenyl)-ethyl]-pyrrolidine-2-one as a Mixture of Diastereoisomers

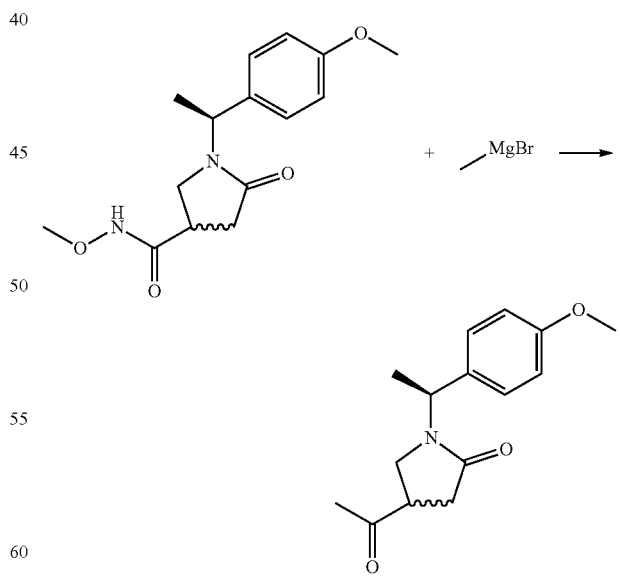

530 mL of a 3M solution of methylmagnesium bromide in diethylether were added slowly to a cooled solution of 271 g of (R/S)—N-methoxy-5-oxo-1-[(S)-1-(4-methoxyphenyl)-ethyl]-pyrrolidine-3-carboxamide (mixture of diastereoisomers) in 1.4 L of 2-methyltetrahydrofuran so that the temperature remained under 0° C. After complete addition the temperature was kept for 75 minutes at 0° C. and then warmed up to 20° C. The suspension was stirred 16 hours at 20° C. Under cooling 650 mL of a 4M hydrochloric acid were added. The organic phase was separated and washed with 500 mL saturated sodium carbonate solution and with 500 mL saturated brine. The organic phase was dried over sodium sulfate. After filtration the solvent was evaporated under reduced pressure.

Yield: 188 g (81% of theory) of (R/S)-4-Acetyl-1-[(S)-1-(4-methoxyphenyl)-ethyl]-pyrrolidine-2-one (mixture of diastereoisomers) as an oil.

Analysis (method H): R$_t$: 7.4 min and 9.6 min, (M+H)$^+$: 262

Step 4: Crystallization of (R)-4-Acetyl-1-[(S)-1-(4-methoxyphenyl)-ethyl]-pyrrolidine-2-one Under Base Induced Epimerization Conditions

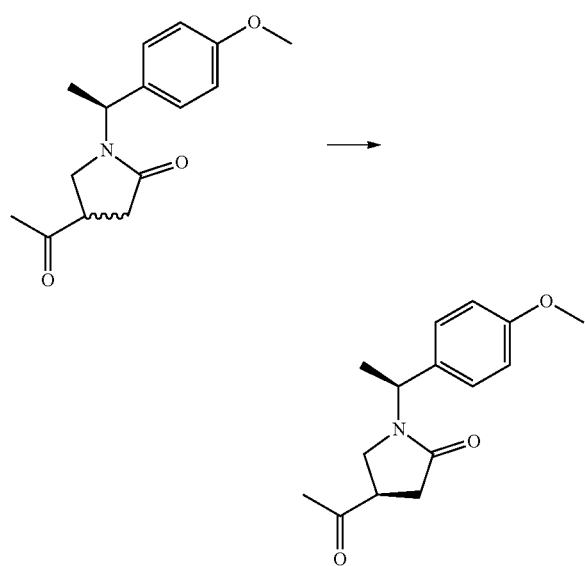

103 g of a mixture of diastereoisomers (R/S)-4-acetyl-1-[(S)-1-(4-methoxyphenyl)-ethyl]-pyrrolidine-2-one were dissolved in 155 mL 1-butanol at 25° C. 18 mL benzyltrimethylammonium hydroxide (40% solution in methanol) was added. The solution was stirred for 30 minutes at 25° C. The solution was cooled to 0° C. Precipitation started. The suspension was stirred for 15 minutes at 0° C. 100 mL n-heptane was added slowly and the suspension was stirred for 30 minutes at 0° C. The addition of 100 mL portions of n-heptane was repeated 4 times with subsequent stirring of the suspension at 0° C. for 30 minutes. The precipitate was isolated, washed with n-heptane and dried at 50° C.

Yield: 77.1 g of a beige solid (75% of theory) with a diastereoisomeric purity of ~95:5 (method H).

For further purification the crude product was dissolved in 310 mL 2-methyl-2-butanol at 40° C. (temperature <50° C.). The solution was slowly cooled to 0° C. Precipitation started. At 0° C. 385 mL of n-heptane were added and the suspension was stirred for 1 hour. The precipitate was filtrated, washed with n-heptane and dried at 50° C.

Yield: 68.7 g (67% of theory) of a colorless solid with a diastereoisomeric purity of >99:1.

Analysis (method H): R$_t$: 6.8 min, (M+H)$^+$: 262

Step 4: Crystallization of (R)-4-Acetyl-1-[(S)-1-(4-methoxyphenyl)-ethyl]-pyrrolidine-2-one Under Base Induced Epimerization Conditions

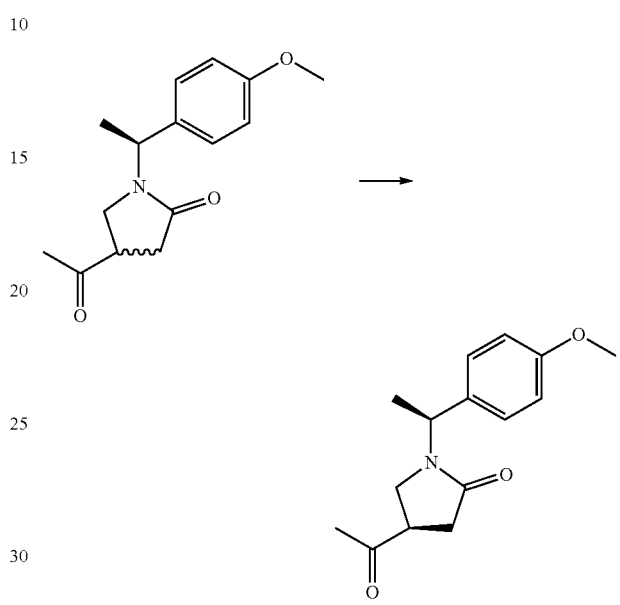

13.2 g of a mixture of diastereoisomers (R/S)-4-acetyl-1-[(S)-1-(4-methoxyphenyl)-ethyl]-pyrrolidine-2-one were dissolved in 18 mL of 1-butanol at 25° C. The solution was cooled to 3° C. and treated with 100 mg of (R)-4-Acetyl-1-[(S)-1-(4-methoxyphenyl)-ethyl]-pyrrolidine-2-one. The resulting mixture was agitated for 15 min at 3° C.; at which point, 2.3 mL benzyltrimethylammonium hydroxide (40% solution in methanol) were added. The solution was stirred for 30 minutes at 3° C. 64 mL n-heptane was added slowly over 1 h at 0 to 3° C. and the suspension was stirred for 60 minutes at 0° C. The precipitate was isolated, washed with n-heptane and dried at 30° C.

Yield: 10.6 g of a beige solid (80% of theory) with a diastereoisomeric purity of ~98:2 (method H).

Analysis (method H): R$_t$: 6.8 min, (M+H)$^+$: 262

Step 5: Synthesis of (R)-4-[(R)-1-Hydroxyethyl]-1-[(S)-1-(4-methoxyphenyl)-ethyl]-pyrrolidin-2-one 2.1

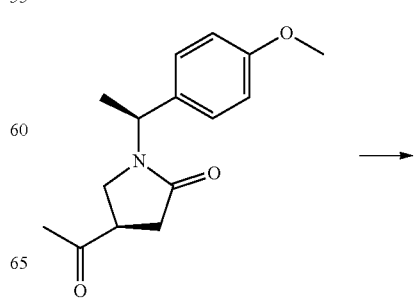

-continued

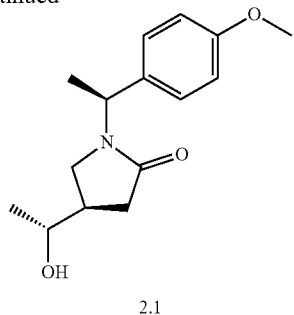

2.1

94.6 mg of dichloro (pentamethylcyclopentadienyl)-iridium(III) dimer and 105 mg of (S,S)—N-(p-toluenesulfonyl)-1,2-diphenylethylendiamine [(R,R)-TsDPEN] were dissolved in 20 mL of acetonitrile and subsequently charged to a slurry of 50 g of (R)-4-acetyl-1-[(S)-1-(4-methoxyphenyl)-ethyl]-pyrrolidine-2-one and 65 g of sodium formate in 500 mL of water at 25° C. The slurry was heated to 60° C. and agitated at this temperature while sparging with nitrogen for 3 h. The reaction was diluted at 60° C. with 500 mL of isopropyl acetate and subsequently cooled to ambient temperature. The layers were separated, and the organic portion was washed twice with 300 mL of water. The organic portion was concentrated to an oily solid. The residual material was crystallized three times from ethyl acetate and hexanes followed by drying in a vacuum oven with a nitrogen stream at 30° C.

25.4 g of a beige solid with a diastereomeric purity of >99:1

Step 5: Synthesis of (R)-4-[(S)-1-Hydroxyethyl]-1-[(S)-1-(4-methoxyphenyl)-ethyl]-pyrrolidin-2-one (2.2

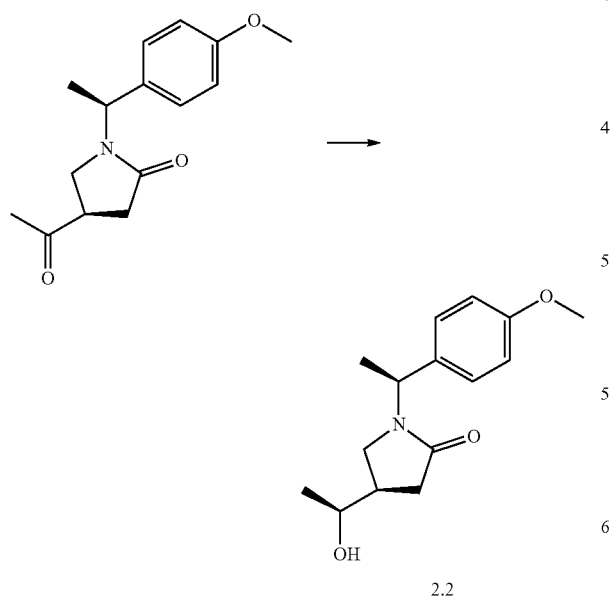

2.2

9.46 mg of dichloro (pentamethylcyclopentadienyl)-iridium(III) dimer and 10.52 mg of (R,R)—N-(p-toluenesulfonyl)-1,2-diphenylethylendiamine [(R,R)-TsDPEN] were dissolved in 1 mL of acetonitrile and subsequently charged to a slurry of 5 g of (R)-4-acetyl-1-[(S)-1-(4-methoxyphenyl)-ethyl]-pyrrolidine-2-one and 6.5 g of sodium formate in 50 mL of water at 25° C. The slurry was heated to 60° C. and agitated at this temperature while sparging with nitrogen for 3 h. The reaction was diluted at 60° C. with 50 mL of isopropyl acetate and subsequently cooled to ambient temperature. The layers were separated, and the organic portion was washed with 20 mL of water. The organic portion was concentrated to an oil. The oil was dissolved in 8 mL of isopropyl acetate at reflux. The solution was cooled to ambient temperature wherein crystallization occurred. The mixture was diluted dropwise with 10 mL of heptane at ambient temperature. The mixture was agitated for 30 minutes. The solids were collected by filtration, washed with a solution of 20 vol % isopropyl acetate in heptane and dried in a vacuum oven with a nitrogen stream at 55° C. 3.82 g of a beige solid with a diastereomeric purity of 99:1

Analysis (method I): $R_t$: 12.9 min, $(M+H)^+$: 264

Synthesis of [(1 S)-1-[(3R)-1-[(1 S)-1-(4-Methoxyphenyl)ethyl]-5-oxo-pyrrolidin-3-yl]ethyl]4-methyl-benzenesulfonate (2.3 for Example 13, 16, 18, 20, 21, 22

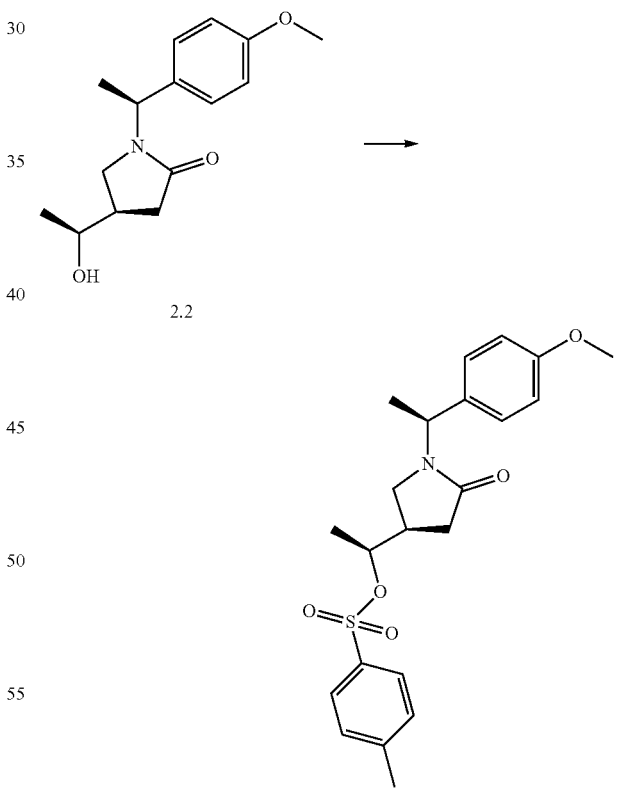

2.3

To a mixture of (R)-4-[(S)-1-Hydroxyethyl]-1-[(S)-1-(4-methoxyphenyl)-ethyl]-pyrrolidin-2-one 2.2 (20.0 g), p-toluenesulfonyl chloride (21.67 g) and N,N-dimethylpyridin-4-amine (0.92 g) was added 42 mL pyridine and dichloromethane (42 mL/DCM). The resulting mixture was stirred at 34° C. for 18 h under argon atmosphere. The reaction mixture was diluted with Isopropyl acetate and washed with water and 2M aqueous HCL. The combined organic phases were dried over magnesium sulfate, filtered and concentrated in vacuo. The residue was taken up in Isopropyl acetate and n-Heptane. The precipitate was filtered off, washed with n-Heptane/Isopropyl acetate to provide of [(1 S)-1-[(3R)-1-[(1 S)-1-(4-methoxyphenyl)ethyl]-5-oxo-pyrrolidin-3-yl]ethyl] 4-methylbenzenesulfonate (2.3) (19.83 g) as solid.

Analysis: HPLC-MS: $R_t$=0.680 min (method J), M+H=418

Synthesis of 5-(1-Hydroxy-ethyl)-3-(4-methoxy-benzyl)-oxazolidin-2-one (2.4 for Example 3

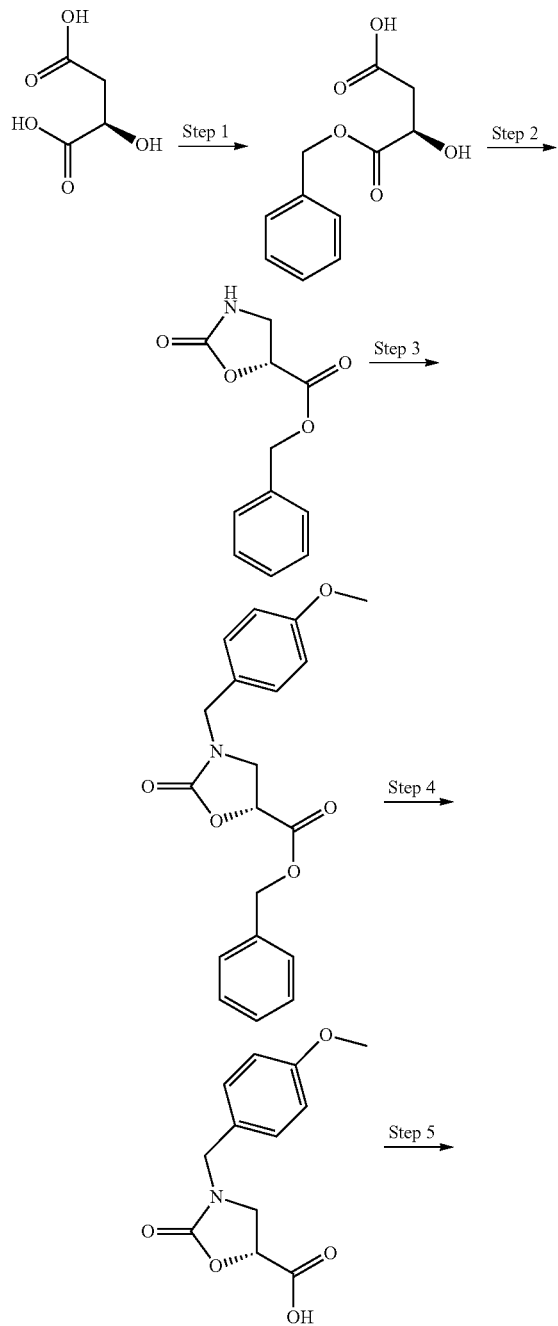

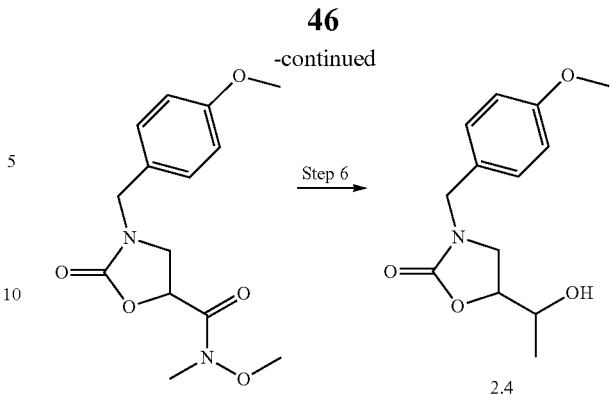

Step 1: To (R)-2-Hydroxy-succinic acid (10 g) was added under cooling trifluoracetic acid anhydride (25 mL) and the mixture is stirred at ambient temperature. After 4 h the solution was concentrated under vacuum to which benzyl alcohol was added and the mixture was stirred over night. The solution was concentrated under vacuum (3 mbar, 60° C.) and the residual oil (28 g) was used without further purification in the next step.

Analysis: HPLC-MS: $R_t$=0.99 min (method E), M+H=225

Step 2: The product from the previous step (23 g) was dissolved in toluene (350 mL) and Triethylamine (16 mL) and diphenylphosphorylazide (24.5 mL) was added. The mixture was stirred under reflux for 3 h, then partial concentrated and extracted with water (250 mL) and EtOAc (250 mL). The phases were separated and the water phase was extracted twice with EtOAc (100 mL). The combined organic phases were washed with sat. NaHCO₃, dried over MgSO₄ and concentrated. The residual was purified via SiO₂ (Cyclohexan/EtOAc 1:2) to provide 7.4 g of a white solid.

Analysis: HPLC-MS: $R_t$=0.95 min (method E), M+H=222

Step 3: To (R)-2-Oxo-oxazolidine-5-carboxylic acid benzyl ester (1.5 g) in acetonitrile (20 mL) was added Cs₂CO₃ (3.31 g) and after 10 mins 1-Bromomethyl-4-methoxy-benzene (1.86 g) and the mixture was stirred for 14 h at 45° C. Water (20 mL) and DCM (60 mL) was added and the mixture stirred for 10 mins. Then the phases were separated, the organic phase concentrated and the product purified via prep HPLC to provide (R)-3-(4-methoxy-benzyl)-2-oxo-oxazolidine-5-carboxylic acid benzyl ester (349 mg) as white solid.

Analysis: HPLC-MS: $R_t$=0.85 min (X018_S03), M+H=342

Step 4: To (R)-3-(4-Methoxy-benzyl)-2-oxo-oxazolidine-5-carboxylic acid benzyl ester (345 mg) in 2.5 mL water and dioxane (2.5 mL) was added 0.485 mL LiOH (2.5N) and the mixture stirred at ambient temperature for 1.5 h. Acetonitrile (10 mL), water (20 mL) and 1M aqueous HCL (1.2 mL) was added and the product lyophilized to provide a white solid (310 mg) which was used without further purification in the next step.

Analysis: HPLC-MS: $R_t$=0.52 min (X018_S01), M+H=252

Step 5: To (R)-3-(4-Methoxy-benzyl)-2-oxo-oxazolidine-5-carboxylic acid (310 mg) and dimethylhydroxylamine*HCl (210 mg) in DMF (5 mL) at 0° C. was added hydroxybenzotriazole (140 mg), N-methyl-morpholine (300 µL) and 1-Ethyl-3-(3-dimethylaminopropyl)carbodiimide xHCl (200 mg) and the mixture was stirred for 3.5 h. iPrOAc (50 mL) and a solution of citric acid 10%, 20 mL) was added and the phases were separated. The water phase was extracted twice with iPrOAc (20 mL) and the combined organic phased were washed with aqueous NaHCO$_3$ (5%, 20 mL). The dried organic phase was concentrated and purified via prep HPLC to provide (R)-3-(4-Methoxy-benzyl)-2-oxo-oxazolidine-5-carboxylic acid methoxy-methyl-amide (147 mg) of colourless oil.

Analysis: HPLC-MS: R$_t$=0.60 min (X018_S03), M+H=295

Step 6: To (R/S)-3-(4-methoxy-benzyl)-2-oxo-oxazolidine-5-carboxylic acid methoxy-methyl-amide (145 mg) in 2 mL THF was added methylmagnesiumbromide (1.4N, 490 µL) under cooling over 20 mins at −10° C. and the mixture was stirred for 30 mins. To this mixture was added 1N aqueous KHSO$_4$ (160 µL), NaBH$_4$ (56 mg) and EtOH (300 µL) at −1° C. and the mixture stirred for 30 mins. Dichloromethane (20 mL) and water (15 mL) was added and the phases were separated and the water phase extracted once with DCM. The combined organic phases were concentrated and purified via prep HPLC (water/acetonitrile/NH$_3$) to provide 5-(1-Hydroxy-ethyl)-3-(4-methoxy-benzyl)-oxazolidin-2-one (90 mg) 2.4 as colourless oil containing all 4 stereoisomers in a comparable amount.

Analysis: HPLC-MS: R$_t$=0.42 min (X011_S03), M+H=250

Chiral HPLC: Chirlapak AS-H 4, 6×250 mm, 5 µm 4 ml/min, scCO$_2$/Isopropanol, 20 mM NH$_3$, 20% in 10 mins, 150 bar. R$_t$=2.577 mins (product a), R$_t$=2.986 mins (product b), R$_t$=3.362 mins (product c), R$_t$=3.655 mins (product d).

4.1.2. Synthesis of pyrazoles with formula 3 and 4

4.1.2.1. Synthesis of halogenated pyrazoles 3

Synthesis of 4-Bromo-1-tert-butyl-pyrazole (3.1) for Examples 3, 13, 15

Step 1: Synthesis of 1-tert-Butyl-pyrazole

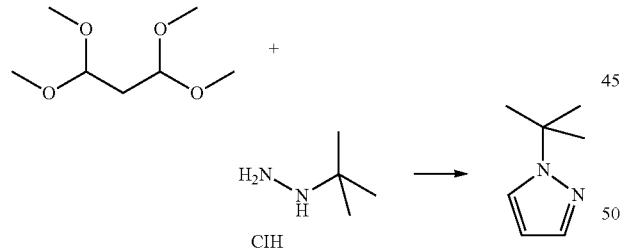

To a stirred mixture of 34.48 g of 1,1,3,3-tetramethoxy-propane and 26.20 g tert.-butylhydrazine hydrochloride in 230 mL ethanol was added 40.0 mL conc. hydrochloric acid dropwise below 50° C., then the mixture was stirred under reflux for 2 h. The reaction mixture was diluted with water. The solvent was almost removed by destillation and the aqueous residue extracted with diethylether. The combined aqueous phases were basified with 10N sodium hydroxide solution and extracted with diethylether. The combined organic phases were washed with saturated brine, dried over sodium sulfate, filtered and concentrated in vacuo to yield 21.90 g of 1-tert-butyl-pyrazole as oil.

Analysis: HPLC-MS: R$_t$=0.412 min (method A), M+H=125

Step 2: Synthesis of 4-Bromo-1-tert-butyl-pyrazole

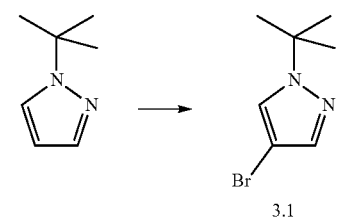

To a mixture of 21.9 g of 1-tert-butyl-pyrazole in 150 mL DCM was added 31.5 g N-bromosuccinimide in portions between 0 and 10° C. The resulting mixture was stirred for 30 min. The reaction mixture was allowed to reach ambient temperature. The precipitate was filtered off and washed with DCM. The combined organic extracts were washed with water and saturated brine, dried over magnesium sulfate, filtered and concentrated in vacuo to yield 34.0 g of 4-bromo-1-tert-butyl-pyrazole as oil.

Analysis: HPLC-MS: R$_t$=1.35 min (method B), M+H=203/205

Synthesis of 4-Bromo-1-(2,2,5,5-tetramethyl-tetrahydrofuran-3-yl)-1H-pyrazole (3.2) for Examples 14, 16

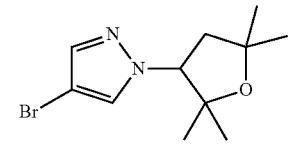

To a mixture of 1-(2,2,5,5-tetramethyl-tetrahydrofuran-3-yl)-1H-pyrazole (900 mg) in 15 mL DCM was added N-bromosuccinimide (830 mg) at room temperature. The resulting mixture was stirred for 2 h. To the reaction mixture was then added 15 mL of saturated brine. The organic phase was dried over Na$_2$SO$_4$ filtered and concentrated in vacuo to yield 1.26 g of 3.2 as oil which subsequently crystallized.

Analysis: HPLC-MS: R$_t$=0.601 min (method X018_S03), M+H=273/275

Synthesis of 2-(4-Bromo-pyrazol-1-yl)-2-methyl-propionitrile (3.3) for Example 17

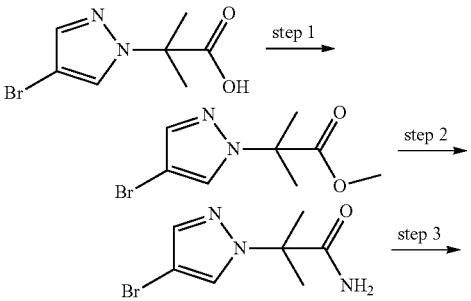

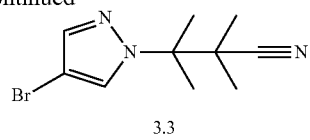

3.3

Step 1: The acid (4 g) was dissolved in methanol (40 mL) and thionylchlorid (4.5 mL) was added at 10° C. The mixture was stirred over night at room temperature, then evaporated and dissolved in DCM. The organic phase was extracted with aqueous sodium bicarbonate, dried over MgSO$_4$ and after filtration concentrated under vacuum to yield 4 g methylester for step 2.

Analysis: MS: M+H=247/249, R$_t$=1.121 min (method Z001_005)

Step 2: The methylester (1 g) was dissolved in methanol (4 mL) containing 10% NH$_3$. 0.5 g calcium chloride was added and the mixture stirred for 20 h at room temperature. The mixture was concentrated and distributed between isopropylacetat (50 mL) and water (20 mL). The water phase was again extracted with isopropylacetat (20 mL) and the combined organic phases dried and concentrated under vacuum to yield 830 mg amide.

Analysis: MS: M+H=232/234, R$_t$=0.705 min (method Z018_S04)

Step 3: The amide (336 mg) was dissolved in 400 μL POCOl$_3$ and stirred at 90° C. for 1.5 h. The reaction mixture was poured onto water and the pH was adjusted to 7-8 via addition of aqueous NaHCO$_3$. The water phase was extracted 3× with DCM and th organic phases were concentrated in vacuo to yield 284 mg 3.3.

Analysis: MS: M+H=214, R$_t$=0.58 min (method X011_S03)

Synthesis of
4-Bromo-1-(3,3-difluoro-cyclopentyl)-1H-pyrazole
3.4 for Examples 7, 22

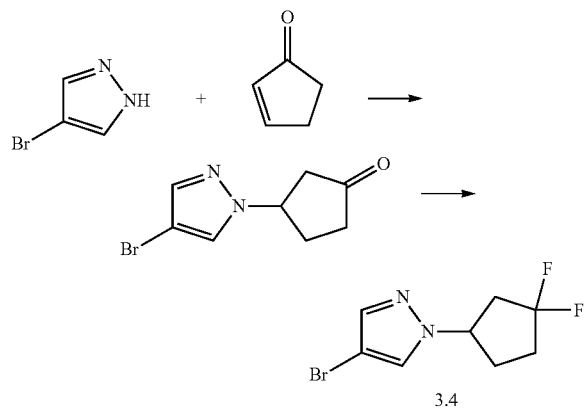

3.4

Step 1: The 4-bromopyrazole (12 g) and 2-cyclopenten-1-one (7.1 g) was suspended in acetonitrile (100 mL). Then scandium trifluoromethansulfonate (0.5 g) was added (slightly exothermic) and the mixture was stirred at room temperature over night and 2 h at 40° C.

The mixture was concentrated and the yellow oil was purified via silica gel (2 kg SiO$_2$, gradient cyclohexane→cyclohexane:ethylacetate 7:3) to yield 16.8 g ketone.

Analysis: MS: M+H=229/231, R$_t$=0.622 min (method X018_S03)

Step 2: The ketone (5 g) was dissolved in dichloromethane (80 mL) and [Bis(2-methoxyethyl)amino]sulfurtrifluoride (45 mL, 50% in THF) was added in portions at 30° C. The mixture was poured onto aqueous sodium bicarbonate solution and extracted with dichloromethane. The organic phase was washed with brine, dried over Na$_2$SO$_4$ and after filtration concentrated at 40 mbar to yield 3.67 g 3.4

Analysis: MS: M+H=251/253, R$_t$=0.848 min (method X018_S03)

The following halogenides were commercially available:
4-Bromo-1-(3,3,3-trifluoropropyl)-1H-pyrazole 3.5 for Examples 12
4-Chloro-1-(2-Fluoro-ethyl)-1H-pyrazole 3.6 for Example 11
4-Bromo-3-tert-butyl-1H-pyrazole 3.7 for Example 4

4.1.3. Synthesis of compounds of formula 4 (Scheme 1 and 2)

Synthesis of 1-tert-Butyl-4-(4,4,5,5-tetramethyl-1,3,2-dioxaborolan-2-yl)pyrazole (4.1) for Examples 3, 13, 15

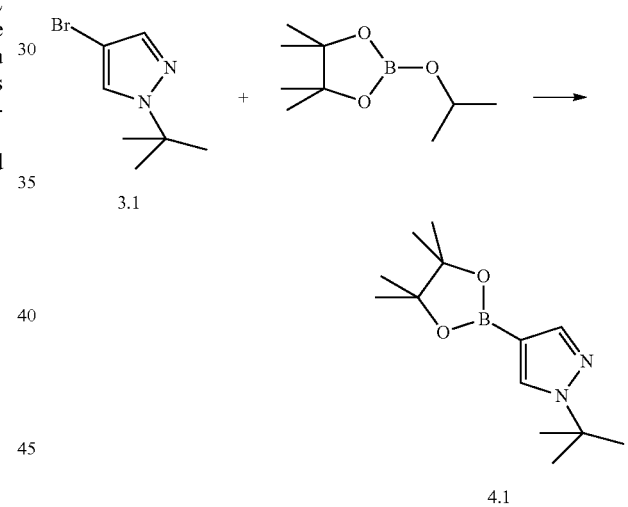

4.1

To a stirred mixture of 4-bromo-1-tert-butyl-pyrazole 3.1 (50 g) in 230 mL THF was added dropwise 2.5M N-butyllithium (100 mL, hexane) under argon atmosphere below −60° C., then the mixture was stirred at this temperature for 5 min, before 2-Isopropoxy-4,4,5,5-tetramethyl-1,3,2-dioxaborolane (52 mL) were added dropwise below −60° C. The reaction mixture was allowed to reach ambient temperature. The mixture was cooled with an ice bath and diluted with aqueous phosphate buffer and water and neutralized with 2M aqueous hydrochloric acid. The organic solvent was removed by destillation and the residue was extracted with DCM. The combined organic extracts were washed with saturated brine, dried over sodium sulfate, filtered and concentrated in vacuo to yield 1-tert-butyl-4-(4,4,5,5-tetramethyl-1,3,2-dioxaborolan-2-yl)pyrazole (44.26 g) as solid.

Analysis: HPLC-MS: R$_t$=0.904 min (method F), M+H=251

Synthesis of 3-Tert-butyl-1H-pyrazol-4-yl-4-boronic Acid (4.2) for Example 4

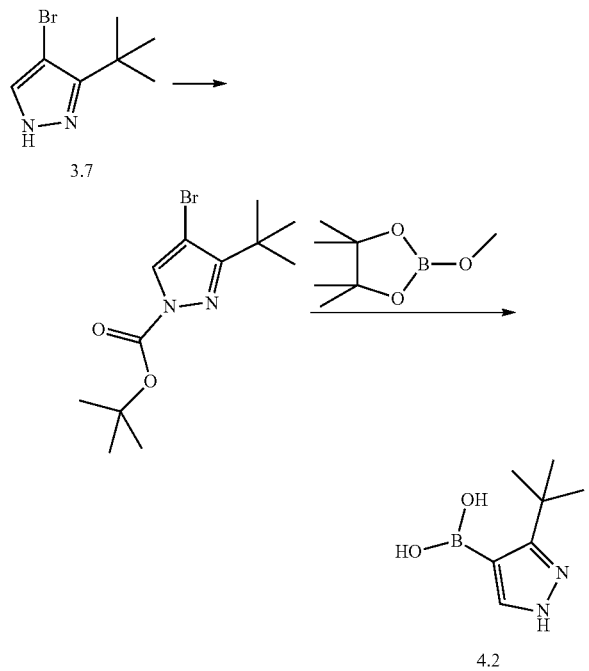

4.1.4. Synthesis of compounds of formula 5

Synthesis of Toluene-4-sulfonic Acid (3R,3aS,7aR)-(hexahydro-furo[3,2-b]pyran-3-yl) ester (5.1) for Example 10

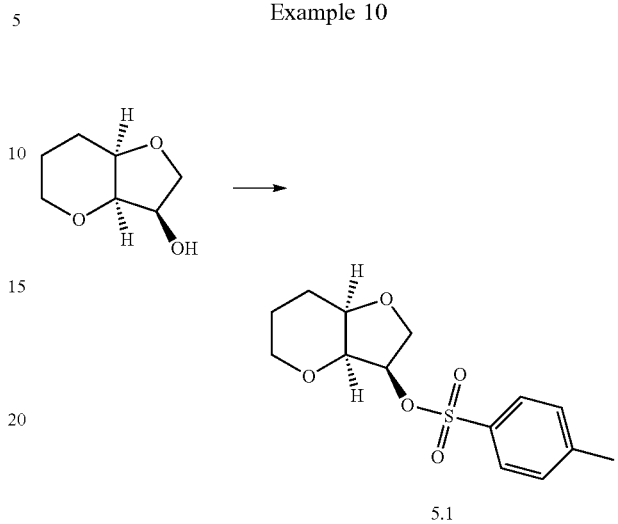

(3R,3aR,7aR)-Hexahydro-furo[3,2-b]pyran-3-ol (300 mg) was dissolved in Dichloromethane (3 mL) and pyridine (0.445 g). p-Toluene sulfonic acid chloride (0.524 g) and DMAP (15 mg) was added and the mixture stirred for 68 h at room temperature. Then water (20 mL) and dichlormethane (20 mL) was added and stirring continued for 15 min. The phases were separated and the organic phase concentrated. Purification was achieved via flash chromatography on silica gel (cyclohexane→cyclohexane/ethylacetate 1:1) to provide 5.1 (0.451 g) as colourless oil.

Step 1: 4-Bromo-3-tert-butyl-1H-pyrazole 3.7 (580 mg) was dissolved in dichloromethane (20 mL) and triethylamine (477 µL) and di-tert-butyldicarbonate (623 mg) at room temperature for 48 h. The mixture was extracted with water and the organic phase separated and concentrated to yield 833 mg as colorless oil.

Analysis: HPLC-MS: $R_t$=0.80 min (X012_S01), M+H=249

Step 2: 4-Bromo-3-tert-butyl-pyrazole-1-carboxylic acid tert-butyl ester (369 mg) was dissolved in THF (6 mL) and cooled to −78° C. n-BuLi (837 µL, 1.6M) was added and the mixture stirred for 20 min. Then 2-methoxy-4,4,4,4-tetramethyl-1,3,2-dioxaborolane (239 L) was added and the mixture was allowed to warm to room temperature over night. Water and DCM was added to the reaction mixture and the organic phase was separated. The water phase was purified via prep HPLC to provide 39 mg 4.2.

Analysis: HPLC-MS: $R_t$=0.47 min (X012_S01), M+H=169

The following boronic acids, boronic esters were commercially available:
1-(Cyclopropylmethyl)-4-(4,4,5,5-tetramethyl-1,3,2-dioxaborolan-2-yl)-1H-pyrazole 4.4 for Example 6, 8
1-Cyclopropyl-4-(4,4,5,5-tetramethyl-1,3,2-dioxaborolan-2-yl)-1H-pyrazole 4.5 for Examples 5, 20
1-Isopropyl-1H-pyrazole-4-boronic acid pinacol ester 4.6 for Examples 2, 18
1-Cyclobutyl-4-(4,4,5,5-tetramethyl-1,3,2-dioxaborolan-2-yl)-1H-pyrazole 4.8 for Examples 1, 21
4-(4,4,5,5-Tetramethyl-1,3,2-dioxaborolan-2-yl)-1H-pyrazole 4.9 for Examples 9, 10
Isobutyl-4-(4,4,5,5-tetramethyl-1,3,2-dioxaborolan-2-yl)-1H-pyrazole 4.10 for Example 19

Analysis: HPLC-MS: $R_t$=0.52 min (X012_S01), M+H=299

The following tosylate was commercially available:
(S)-2,2-Dimethyltetrahydro-2H-pyran-4-yl 4-methylbenzenesulfonate 5.2 for Example 9

4.1.5. Synthesis of Heterocyclic 6 from Scheme 1, 2 and 3

Synthesis of 6-Bromo-2,3-dimethyl-2H-indazol-4-ol (6.1) for Examples 8-11, 13, 16-22

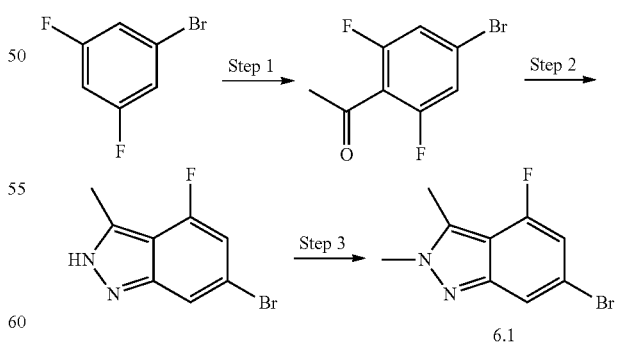

Step 1: 1-Bromo-3,5-difluorobenzene (100 g) was dissolved in THF (600 mL) and cooled to −78° C. LDA (300 mL, 2N in heptane/THF/ethylbenzene) was added over 20 min and the mixture stirred for 1 h. This mixture was added via transfer canula to acetic anhydride (250 mL, cooled to -78° C.) within 30 mins. Then the mixture was warmed to −30° C., THF was removed in vacuum and dichloromethane (300 mL) was added. The mixture was basified with saturated sodium bicarbonate solution and extracted 3× with dichloromethane (300 mL). The organic phase was washed with sat. ammonia chloride solution and sat. brine, dried and concentrated at 100 mbar/50° C. in vacuum. The residue was fractional destilled in vacuum at 30 to 10 mbar/70-100° C. to yield 57.8 g and 74.7 g (content 80%) desired product.

Analysis: HPLC-MS: $R_t$=0.974 min (Z018_S04), M+H=235

Step 2: To 1-(4-Bromo-2,6-difluoro-phenyl)ethanone (22.05 g) dissolved in THF (80 mL) was added hydrazine hydrate (10 mL) at ambient temperature and the mixture was stirred over night. Water (50 mL) and 2-Me-THF (70 mL) were added and the organic phase was dried and concentrated in vacuum. The crude product was dissolved in acetonitrile (70 mL) at 80° C. and cooled to room temperature for 2 days. The precipitate was filtered and washed with acetonitrile and dried under vacuum for 45 min at 45° C. to provide 15.6 g white needles.

Analysis: HPLC-MS: $R_t$=0.58 min (X011_S03), M+H=229/231

Step 3: The indazole (32 g) from the previous step was suspended in dichloromethane (400 mL) and trimethyloxonium tetrafluoroborate (26.75 g) was added and the mixture stirred for 24 h at room temperature. Saturated sodium bicarbonate (150 mL) was added and the mixture was basified to pH 9 with sodium carbonate (10 mL). The precipitate was filtered off, the phases separated and the water phase extracted with iPrOAc. The combined organic phases were dried and concentrated in vacuum to yield 33.1 g raw material which was dissolved in methyl-tert-butyl ether (100 mL) and heated to reflux and cooled to room temperature. The precipitate was filtered off after 2 days to yield 6.1 (22.4 g) as light yellow crystals.

Analysis: HPLC-MS: $R_t$=0.673 min (X018_S02), M+H=243/245

Synthesis of 4,6-Dichloro-2,3-dimethyl-2H-pyrazolo [4,3-c]pyridine (6.2) for Examples 3, 4, 15

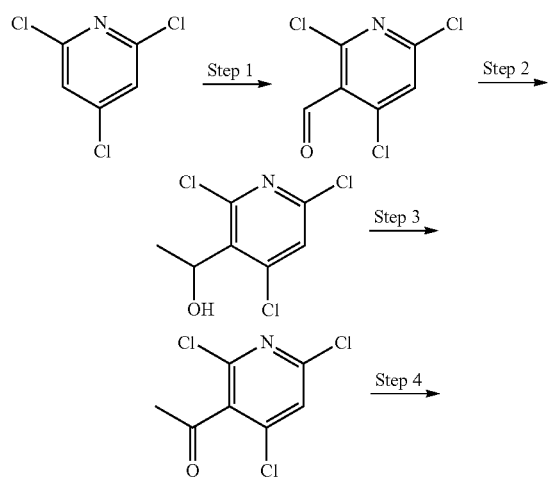

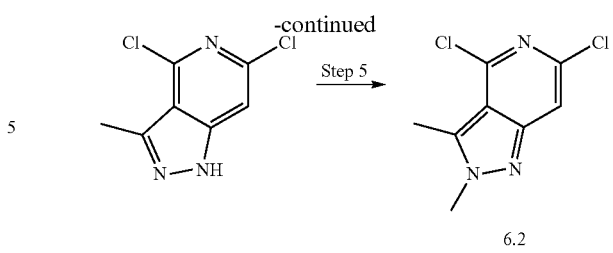

Step 1: To a solution of 2,4,6-trichloro-pyridine (5.00 g) in tetrahydrofuran (anhydrous, 50.00 mL) at −78° C. under a nitrogen atmosphere was added n-butyl lithium (2.5M in hexane) (10.96 ml) dropwise. The mixture was stirred at −78° C. for 1 h and then piperidine-1-carbaldehyde (3.04 mL) was added drop wise. The reaction was stirred at −78° C. for 1 h. The reaction mixture was quenched with sat NH$_4$Cl aq (50 ml). The mixture was extracted with TBME (3×40 mL) and the organic phase washed successively with 1M HCl (75 mL) and sat. ammonium carbonate (75 mL). The organic phase were dried (Na$_2$SO$_4$) and concentrated and the residue purified by Biotage Isolera FCC (SiO$_2$: 50 g) eluting with 10-50% TBME in cyclohexane to give 2.94 g of product as a yellow solid.

Analysis: HPLC-MS: $R_t$=1.27 min (method P)
$^1$H NMR (DMSO, 250 MHz) δ 8.07 (1H, s), 10.28 (1H, s)

Step 2: To methylmagnesium bromide (3M in diethyl ether, 3.83 mL) was added dropwise to a stirred solution of 2,4,6-trichloro-pyridine-3-carbaldehyde (2.20 g) in tetrahydrofuran (anhydrous, 44 mL) at −78° C. under a nitrogen atmosphere. The reaction was stirred at −78° C. for 30 mins and then allowed to warm to room temperature. The reaction was quenched with NH$_4$Cl (25 mL) and neutralised to pH 7-8 with 1M HCl. The aqueous phase was extracted with EtOAc (3×50 mL) the combined organic phase dried (Na$_2$SO$_4$) and concentrated. The crude material was purified by Biotage Isolera (SiO$_2$; 50 g) eluting in 0-100% EtOAc in Cyclohexane to give 1.39 g (58.7%) as colourless oil.

Analysis: HPLC-MS: $R_t$=1.19 min (method P), M+H=226/228
$^1$H NMR (CDCl$_3$, 500 MHz) b 1.64 (3H, d, J=6.9 Hz), 2.67 (1H, d, J=9.2 Hz), 5.51 (1H, d, J=6.9 Hz), 7.33 (1H, s)

Step 3: To a stirred solution of 1-(2,4,6-trichloro-pyridin-3-yl)-ethanol (2.57 g) in dichloromethane (51.4 mL) was added N-methyl morpholine-N-oxide (1.994 g). The reaction was stirred at room temperature for 10 mins after which time tetra-n-propylammonium perruthenate (TPAP) (135.6 mg) was added and stirring continued for 7 days. The mixture was filtered through celite and the filtrate concentrated and purified by Biotage Isolera FCC (SiO$_2$; 25 g) eluting with 7:1 cyclohexane-EtOAc to give 1.74 g as colourless oil.

Analysis: HPLC-MS: $R_t$=1.27 min (method P), M+H=224/226
$^1$H NMR (CDCl$_3$, 500 MHz) b 2.59 (3H, s), 7.38 (1H, s)

Step 4: To a solution of 1-(2,4,6-trichloro-pyridin-3-yl)-ethanone (1.75 g in ethanol, absolute (8.75 mL) was added hydrazinehydrate (0.76 mL). The reaction was stirred at room temperature over the weekend (40 h). The solvent was evaporated and water (10 mL) added. The aqueous phase was extracted with DCM (3×10 mL), the combined organic phases were dried (Na$_2$SO$_4$) and concentrated. The crude material was purified by Biotage Isolera FCC (SiO$_2$; 50 g) eluting 10-30% EtOAc in cyclohexane to give 0.74 g of product as an off white solid.

Analysis: HPLC-MS: $R_t$=1.15 min (method P), M+H=202/204

$^1$H NMR (DMSO, 500 MHz) b 2.64 (3H, s), 7.64 (1H, s)

Step 5: To a solution of 4,6-dichloro-3-methyl-1H-pyrazolo[4,3-c]pyridine (550.00 mg) in dioxan (11.00 mL) under a nitrogen atmosphere was added trimethyloxonium tetrafluoroborate (563.70 mg). The reaction was stirred at room temperature for 1 h. NaHCO$_3$ (10 mL) was added and the mixture extracted with DCM (3×10 mL). The combined organics were dried (Na$_2$SO$_4$), concentrated and the crude residue purified by Biotage Isolera FCC (SiO$_2$; 10 g) 50/50 EtOAc/cyclohexane to give 380 mg of 6.2 (64.6%) as a white solid.

Analysis: HPLC-MS: $R_t$=1.16 min (method P), M+H=216/218

$^1$H NMR (CDCl$_3$, 500 MHz) b 2.84 (3H, s), 4.10 (3H, s), 7.39 (1H, s)

Synthesis of 6-Bromo-3-fluoro-2-methyl-2H-indazol-4-ol (6.3) for Examples 1, 2, 5-7, 12, 14

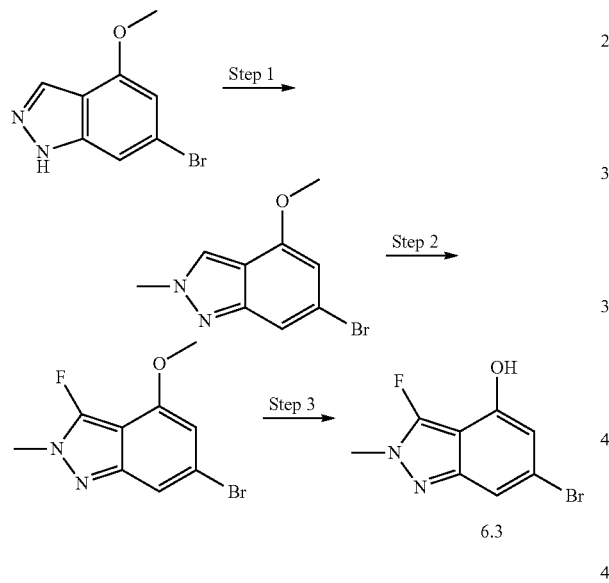

6.3

Step 1: 25 g 6-Bromo-4-methoxy-1H-indazole (commercially available from JW-Pharmlab) was suspended in 400 mL dichloromethane and 20 g trimethyloxonium tetrafluoroborate was added and the mixture stirred for 4 h at room temperature. The reaction mixture was diluted with water (300 mL), filtered via cellulose and diatomic earth and the organic phase was extracted with semi saturated aqueous sodium bicarbonate. The organic phase was dried and concentrated in vacuum to yield 24.6 g.

Analysis: HPLC-MS: $R_t$=0.938 min (Z018_S04), M+H=241/243

$^1$H NMR (DMSO, 400 MHz) b 3.90 (3H, s), 4.10 (3H, s), 6.51 (1H, s), 7.38 (1H, s), 8.37 (1H, s)

Step 2: The indazole (5 g) from the previous step was dissolved in 70 mLTHF and cooled to −78° C. LDA (13.5 mL, 2M in THF) was added slowly and the mixture stirred for 30 mins after which time N-fluorobenzenesulfonimide (9.16 g) was added. After 30 mins the reaction mixture was allowed to warm up, then water and dichloromethane was added and the organic phase was separated and concentrated. The residue was dissolved in DMF/water/TFA and purified via prep HPLC to yield 2.95 g.

Analysis: HPLC-MS: $R_t$=0.56 min (X012_S01), M+H=259/261 $^1$H NMR (DMSO, 400 MHz) b 3.90 (3H, s), 3.94 (3H, s), 6.49 (1H, s), 7.26 (1H, s)

Step 3: 2-Fluoroindazole (2.9 g) from the previous step was dissolved in DCM (10 mL) and boron tribromide (3.24 mL) and the mixture was heated under reflux over night after which time water was added and the mixture was basified with 1N NaOH. The water phase was separated, acidified with 4N HCl and the precipitate was filtered off and dried at 60° C. for 2 h under vacuum to give 6.3 (2.4 g).

Analysis: HPLC-MS: $R_t$=0.41 min (X012_S01), M+H=245/246

$^1$H NMR (DMSO, 400 MHz) b 3.92 (3H, s), 6.34 (1H, s), 7.08 (1H, s), 10.80 (1H, s)

Synthesis of 6-Bromo-2,3-dimethyl-2H-indazol-4-ol (6.4) for Examples 13, 16, 18, 20-22

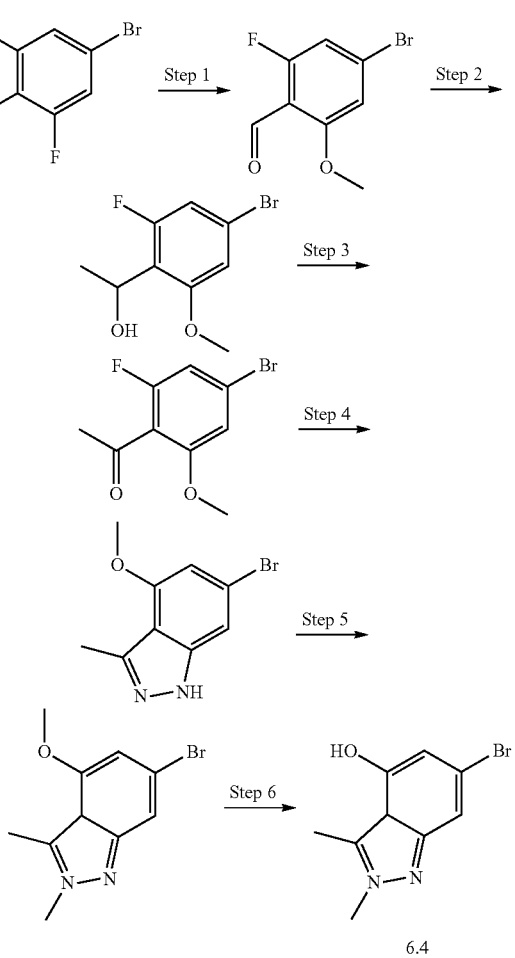

6.4

Step 1: Bromo-2,6 difluoro-benzaldehyde (200 g) were dissolved in 1 L of methanol and Cs$_2$CO$_3$ (300 g) were added under cooling at 10° C. and stirring continued at 30° C. over night. The mixture was acidified to pH 6 with aqueous HCl and the formed precipitate filtered. The precipitate was suspended in EtOH/water 3:1 (800 mL) and dissolved in the heat and cooled to ambient temperature for 2 days. The precipitate (91 g) was collected and purified via SiO$_2$ (MPLC, cyclohexan/ethylacetate 9:1) to give 65.5 g product. The mother liquor was concentrated and extracted with DCM and also purified via SiO$_2$ (MPLC, cyclohexan/ethylacetate 9:1) to give 29.4 g product.

Analysis: HPLC-MS: R$_t$=0.987 min (Z018_S04)

$^1$H NMR (DMSO, 400 MHz) δ 3.91 (3H, s), 7.25-7.33 (2H, m), 10.23 (1H, s)

Step 2: 4-Bromo-2-fluoro-6-methoxy-benzaldehyde (65.5 g) was dissolved in THF (250 mL) and methylmagnesiumbromide (220 mL, 1.4N in toluene/THF) was added at 0° C. and stirred for 48 h at room temperature. Additional methylmagnesiumbromide (60 mL, 1.4N in toluene/THF) was added and stirring continued for 4 h. The mixture was concentrated, suspended in DCM and water (50 mL) and HCl (4N, 20 mL) was added under ice cooling. A precipitate was filtered off, the phases were separated and the water phase was extracted twice with DCM. The organic phases were tried and concentrated to give 70 g product.

Analysis: HPLC-MS: R$_t$=0.950 min (Z018_S04), M+H$^+$= 231/233

$^1$H NMR (DMSO, 400 MHz) δ 1.37-1.38 (3H, d), 3.82 (3H, s), 4.95-4.96 (1H, d), 5.10-5.13 (1H, dt), 7.02-7.06 (2H, m)

Step 3: 1-(4-Bromo-2-fluoro-6-methoxy-phenyl)ethanol (90 g) was dissolved in DCM (500 mL) and tetrapropylammoniumperruthenate (0.6 g, TPAP) and N-methyl morpholine N-oxide (42 g, NMO) and the mixture stirred for 3 h at room temperature. Additional TPAP (0.5 g) and NMO (10 g) were added and the mixture stirred for 3 h after which time it was diluted with DCM and water and the organic phase was separated. 2,4,6 Trimercaptotraizine resin (9 g, 0.5 mnol/g) were added to the organic phase and stirred for 30 mins, dried with Na$_2$SO$_4$, filtered via cellulose and diatomic earth and concentrated in vacuum to yield 100 g (content 70%) product which was used in the next step without further purification.

Analysis: HPLC-MS: R$_t$=0.993 min (Z018_S04), M+H$^+$=247/249

$^1$H NMR (DMSO, 400 MHz) b 2.45 (3H, s), 3.87 (3H, s), 7.22-7.23 (2H, m)

Step 4: 100 g product (content 70%) from the previous step was suspended in ethyleneglycol and hydrazine hydrate (200 mL) and the mixture was stirred at 100° C. for 4 h, then at 70° C. for 48 h. The mixture was poured onto ice water and extracted 3× with DCM. The combined organic phases were tried (Na$_2$SO$_4$) to provide 85 g product as yellow solid which was used in the next step without further purification.

Analysis: HPLC-MS: R$_t$=0.940 min (Z018_S04), M+H$^+$= 241/243

Step 5: 50 g product from the previous step was dissolved in DCM (200 mL) and trimethyl-oxoniumtetrafluoroborate (30 g) was added in portions at 0° C. and stirred overnight at room temperature. To the mixture was added aqueous NaHCO$_3$ and the pH adjusted to 9 with Na$_2$CO$_3$. The mixture was then extracted 3× with DCM and twice with ethylacetate, the organic phases were dried and the residue purified via SiO$_2$ (MPLC, 2.5 kG, cyclohexane/ethylacetate 4:1) and the desired fractions combined to give 18 g product.

Analysis: HPLC-MS: R$_t$=0.944 min (Z018_S04), M+H$^+$= 255/257

$^1$H NMR (DMSO, 400 MHz) b 2.66 (3H, s), 3.89 (3H, s), 3.96 (3H, s), 6.40 (1H, s), 7.26 (1H, s)

Step 6: To 6-Bromo-4-methoxy-2,3-dimethyl-2H-indazole (2.3 g) in DCM (20 mL) was added borontribromide (25 mL, 1M in DCM) and the mixture was stirred for 2 h at 40° C. The mixture was concentrated and extracted with water and DCM. The precipitate was collected and dried to provide 1.62 g 6.4.

Analysis: HPLC-MS: R$_t$=0.761 min (Z018_S04), M+H$^+$= 241/243

$^1$H NMR (DMSO, 400 MHz) b 2.67 (3H, s), 3.94 (3H, s), 6.28 (1H, s), 7.08 (1H, s), 10.40 (1H, s)

4.2. Synthesis of Intermediates 7, 8 and 9, from Scheme 1 and 2

Synthesis of ((R)-4-[(R)-1-(6-Bromo-2,3-dimethyl-2H-indazol-4-yloxy)-ethyl]-1-[(S)-1-(4-methoxy-phenyl)-ethyl]-pyrrolidin-2-one (7.1) for Examples 8-11, 13, 16-22

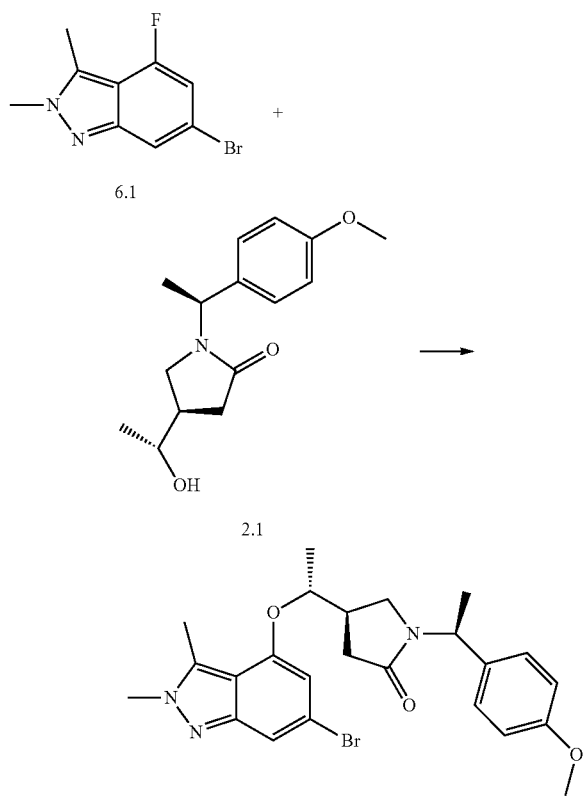

6.1 (32.8 g) was dissolved in DMA (400 mL), then 2.1 (39 g) was added and the mixture was heated to 80° C. Potassium tert-butylat (25 g) was added and the mixture stirred for 20 mins at 80° C. and subsequently cooled to room temperature. Aqueous NH$_4$Cl (100 mL) and water (200 mL) was added. Then the mixture was extracted 3× with i-PrOAc (300 mL) and the combined organic phases were dried over Mg$_2$SO$_4$ and evaporated under reduced pressure to yield 75.1 g (content 88%) product, from which 12 g were purified via preparative HPLC to yield 10.0 g 7.1.

Analysis: HPLC-MS: R$_t$=0.597 min (X016_S01), M+H=486/484

$^1$H NMR (DMSO, 400 MHz) δ 1.16 (3H, d, J=6.1 Hz), 1.41 (3H, d, J=7.2 Hz), 2.33-2.39 (1H, m), 2.44 (3H, s), 2.73 (1H, s), 2.78-2.82 (1H, m), 2.89 (1H, s), 3.18 (1H, d, J=5.1 Hz), 3.49 (1H, t, J=9.2 Hz), 3.64 (3H, s), 3.93 (3H, s), 4.60-4.66 (1H, m), 5.18-5.23 (1H, q, J=7.2 Hz), 6.37 (1H, s), 6.57-6.60 (2H, m), 7.09-7.11 (2H, m), 7.21 (1H, d, J=1.2 Hz)

Alternatively 7.1 was synthesized the following:

Synthesis of (R)-4-[(R)-1-(6-Chloro-2,3-dimethyl-2H-pyrazolo[4,3-c]pyridin-4-yloxy)-ethyl]-1-[(S)-1-(4-methoxy-phenyl)-ethyl]-pyrrolidin-2-one (7.2) for Examples 3, 4, 15

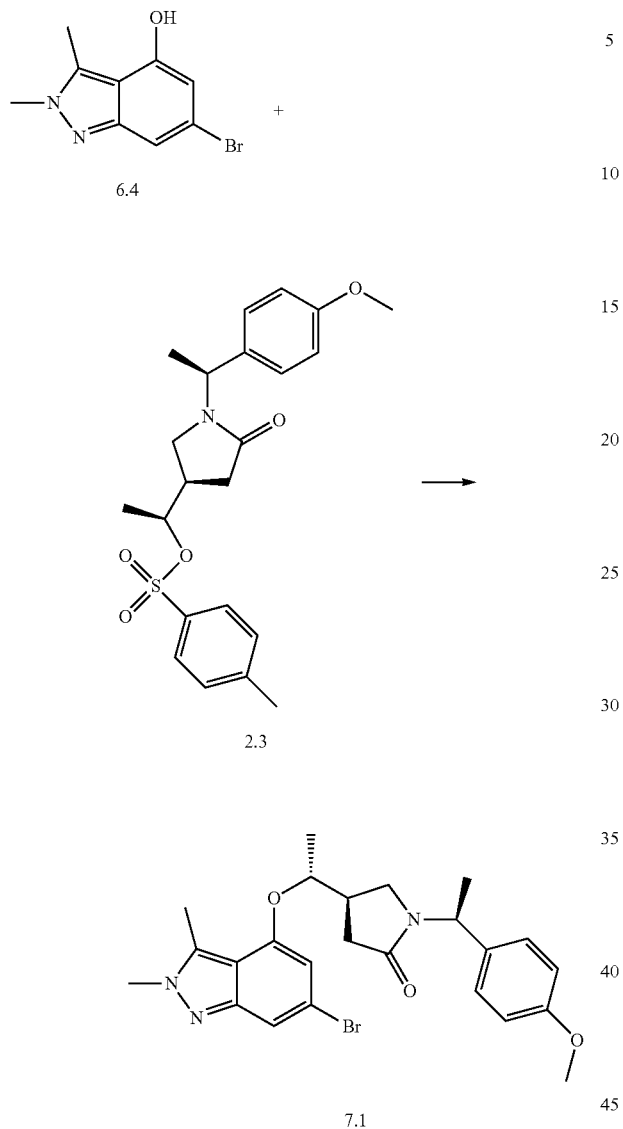

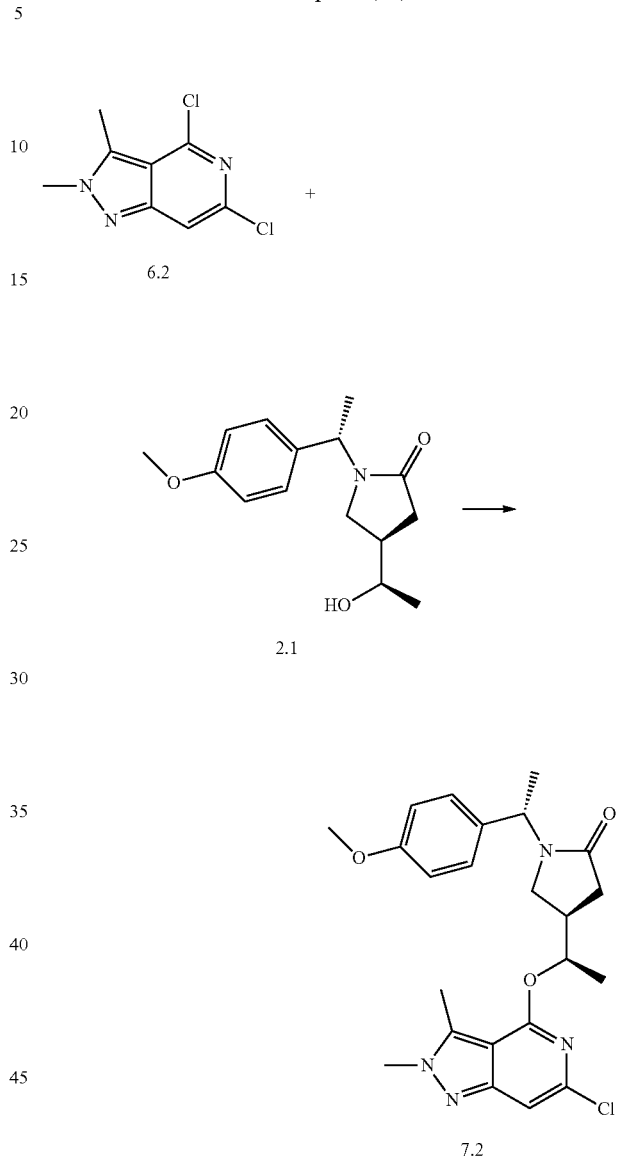

6-Bromo-2,3-dimethyl-2H-indazol-4-ol 6.4 (10.5 g), potassium carbonate (16.8 g) and 2.3 (18.6 g) were suspended in anhydrous DMF and stirred for 2 h at 70° C. and over night at 50° C. Additional 2.3 (5 g) and potassium carbonate (5 g) were added and the mixture stirred for 3 h at 70° 0. The mixture was concentrated, water and DCM was added and the water phase was extracted 3× with DCM (250 mL). The organic phase was washed with $KHSO_4$ and dried ($Na_2SO_4$) and concentrated. The mixture was purified via $SiO_2$ (DCM: MeOH 9:1) to give 12.7 g 7.1

Analysis: HPLC-MS: $R_t$=1.029 min (Z018_S04), M+H=486/488

$^1$H NMR (DMSO, 400 MHz) δ 1.16 (3H, d, J=6.1 Hz), 1.41 (3H, d, J=7.2 Hz), 2.33-2.39 (1H, m), 2.44 (3H, s), 2.73 (1H, s), 2.78-2.82 (1H, m), 2.89 (1H, s), 3.18 (1H, d, J=5.1 Hz), 3.49 (1H, t, J=9.2 Hz), 3.64 (3H, s), 3.93 (3H, s), 4.60-4.66 (1H, m), 5.18-5.23 (1H, q, J=7.2 Hz), 6.37 (1H, s), 6.57-6.60 (2H, m), 7.09-7.11 (2H, m), 7.21 (1H, d, J=1.2 Hz)

2.1 (3.2 g) was dissolved in THF (50 mL) and NaH (1.08 g, 60% dispersion in mineral oil) was added and the mixture stirred for 5 mins, then 6.2 (2.5 g) was added and stirring continued at 50° C. for 3 h. After cooling, aqueous $NH_4Cl$ (50 mL) was added and the mixture extracted 2× with iPrOAc and the combined organic phases dried ($MgSO_4$) and concentrated. The product was purified via prep HPLC to give 7.2 (3.65 g) as white solid.

Analysis: HPLC-MS: $R_t$=0.60 min (X012_S01), M+H=443

$^1$H NMR (DMSO, 400 MHz) b 1.22 (3H, d, J=6.2 Hz), 1.40 (3H, d, J=7.2 Hz), 2.37-2.43 (1H, m), 2.45 (3H, s), 2.51-2.56 (1H, m), 2.64-2.72 (1H, m), 2.76-2.80 (1H, m), 3.53 (1H, t, J=9.3 Hz), 3.62 (3H, s), 3.96 (3H, s), 5.16-5.18 (1H, q, J=7.2 Hz), 5.33-5.35 (1H, m), 6.47-6.49 (2H, m), 7.01-7.03 (3H, m)

Synthesis of (1R,4R)-4-[(R)-1-(6-Bromo-3-fluoro-2-methyl-2H-indazol-4-yloxy)-ethyl]-1-[1-(4-methoxy-phenyl)-ethyl]-pyrrolidin-2-one (7.3) for Examples 1, 2, 5-7, 12, 14

Synthesis of (R)-5-[(R)-1-(6-Chloro-2,3-dimethyl-2H-pyrazolo[4,3-c]pyridin-4-yloxy)-ethyl]-3-(4-methoxy-benzyl)-oxazolidin-2-one (7.4) for Examples 3

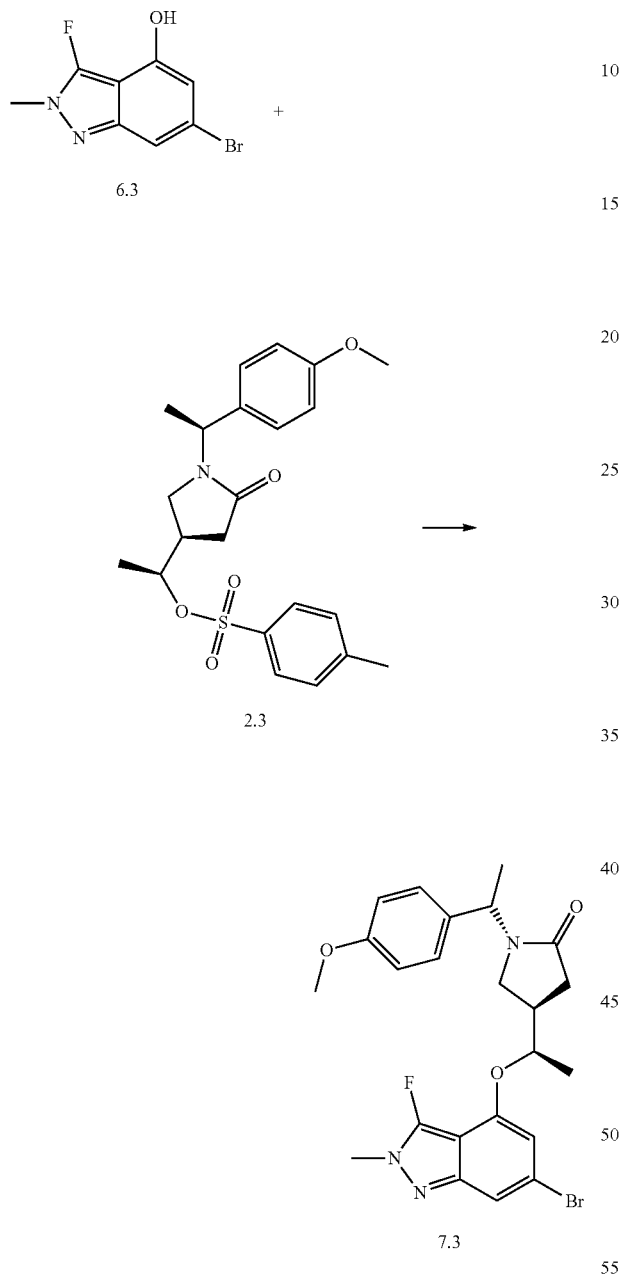

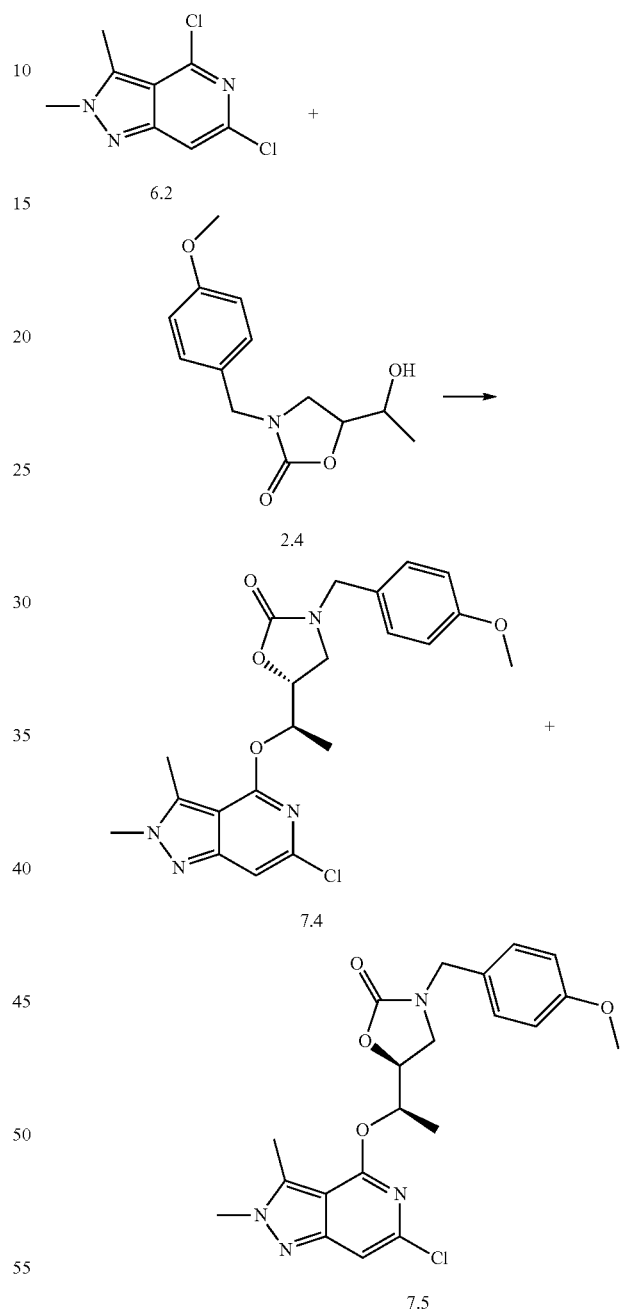

2.4 g 6.3 was dissolved in DMF (20 mL), potassium carbonate (5.41 g) and 2.3 (6.13 g) was added and the mixture stirred at 70° C. over night. The mixture was concentrated in vacuum, water was added and the mixture was extracted 3× with DCM. The organic phase was separated to yield 5.5 g (content 80%) product 7.3 which was used without further purification in the next step.

Analysis: HPLC-MS: $R_t$=0.61 min (X012_S01), M+H=490/492

To 6.2 (75 mg) and NaH (32 mg) was added 2.4 (90 mg) dissolved in dimethylacetamide (DMA; 2 mL) and the solution was stirred for 5 h. The mixture was purified via prep HPLC (water/acetonitril/NH$_3$) to provide 7.4 (38 mg) and 7.5 (46 mg) as white solids. (7.4 and 7.5 as mixture of enantiomers)

Analysis 7.4: HPLC-MS: $R_t$=0.83 min (X018_S03), M+H=431

Analysis 7.5: HPLC-MS: $R_t$=0.87 min (X018_S03), M+H=431

Synthesis of (R)-4-[(R)-1-(6-Bromo-2,3-dimethyl-2H-indazol-4-yloxy)-ethyl]-pyrrolidin-2-one (8.1) for Examples 8, 13, 18, 19, 20

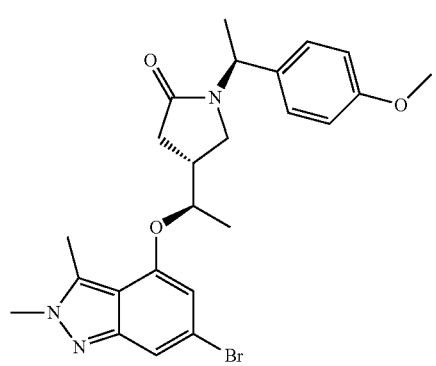

7.1

Synthesis of (R)-4-[(R)-1-(6-Chloro-2,3-dimethyl-2H-pyrazolo[4,3-c]pyridin-4-yloxy)-ethyl]-pyrrolidin-2-one (8.2) for Examples 4, 15

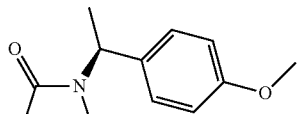

7.2

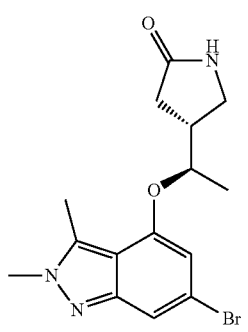

8.1

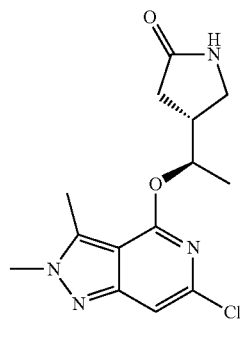

8.2

A mixture of 7.1 (2.3 g) in TFA (40 mL) and anisole (5 mL) was stirred at 80° C. for 15 h and 8 h at room temperature. The reaction mixture was concentrated, diluted with acetonitrile (8 mL), basified with 25% NH₃ and diluted with water and separated via prep HPLC. The yellow oil was dissolved in Methyl tert-butyl ether and formed a white precipitate which was collected after 3 days to give 8.1 (1.35 g).

Analysis: HPLC-MS: $R_t$=0.45 min (X012_S01), M+H=352/354

¹H NMR (DMSO, 400 MHz) b 1.28 (3H, d, J=6.1 Hz), 2.15-2.35 (2H, m), 2.63 (3H, s), 2.72-2.82 (1H, m), 3.07-3.11 (1H, m), 3.37 (1H, t, J=8.9 Hz), 3.95 (3H, s), 4.63-4.69 (1H, m), 6.45 (1H, s), 7.23 (1H, d, J=1.0 Hz), 7.55 (1H, s)

7.2 (2.4 g, content 85%) was stirred in TFA (20 mL) at 80° C. for 4 h after which time it was concentrated. The residual was dissolved in iPrOAc and sat. aqueous NaHCO₃ (30 mL) and water (20 mL) was added. The precipitate was collected, washed with water, iPrOAc and petrol ether to provide 890 mg white solid 8.2.

Analysis: HPLC-MS: $R_t$=0.48 min (X012_S02), M+H=309

¹H NMR (CDCl₃, 500 MHz) b 1.41 (3H, d, J=6.3 Hz), 2.43-2.57 (2H, m), 2.86 (1H, ddd, J=14.1, 8.3, 6.0 Hz), 3.32 (1H, dd, J=9.6, 6.4 Hz), 3.55 (1H, t, J=9.1 Hz), 4.00 (3H, s), 5.59 (1H, m), 5.72 (1H, s), 7.03 (1H, s)

65

Synthesis of (R)-4-[(R)-1-(6-Bromo-3-fluoro-2-methyl-2H-indazol-4-yloxy)-ethyl]-pyrrolidin-2-one (8.3) for Examples 1, 2, 5, 6

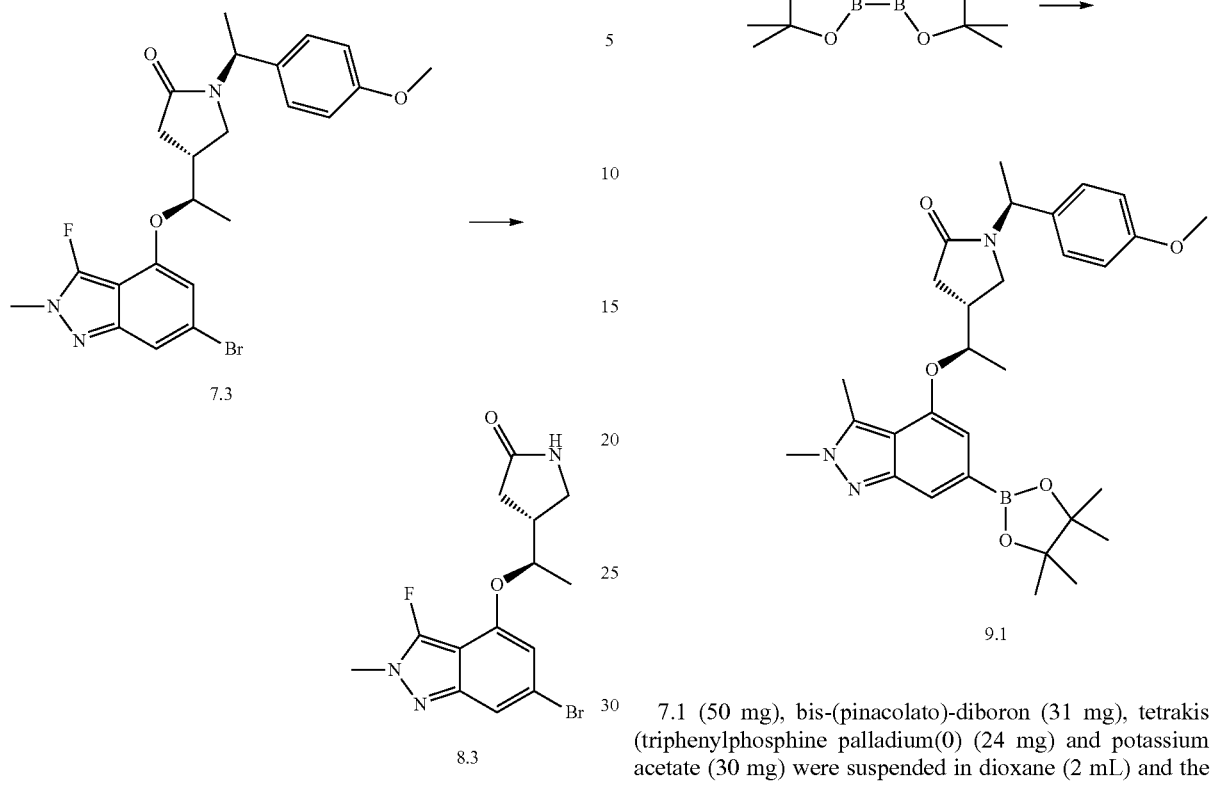

7.3

8.3

A mixture of 7.3 (2.8 g) in 10 mL TFA was stirred at 80° C. for 2 h. The reaction mixture was poured in water, basified with NaOH (4N) and extracted with DCM. The organic phase was concentrated and purified via $SiO_2$ and the desired fractions were combined to give 8.3 (0.868 g).

Analysis: HPLC-MS: $R_t$=0.46 min (X012_S02), M+H=357/359

4.1.6. Synthesis of boronic acids and boronic esters 9 and 12 from Scheme 1 and 2

Synthesis of (R)-4-{(R)-1-[2,3-Dimethyl-6-(4,4,5,5-tetramethyl-[1,3,2]dioxaborolan-2-yl)-2H-indazol-4-yloxy]-ethyl}-1-[(S)-1-(4-methoxy-phenyl)-ethyl]-pyrrolidin-2-one (9.1) for Examples 11, 16, 17, 22

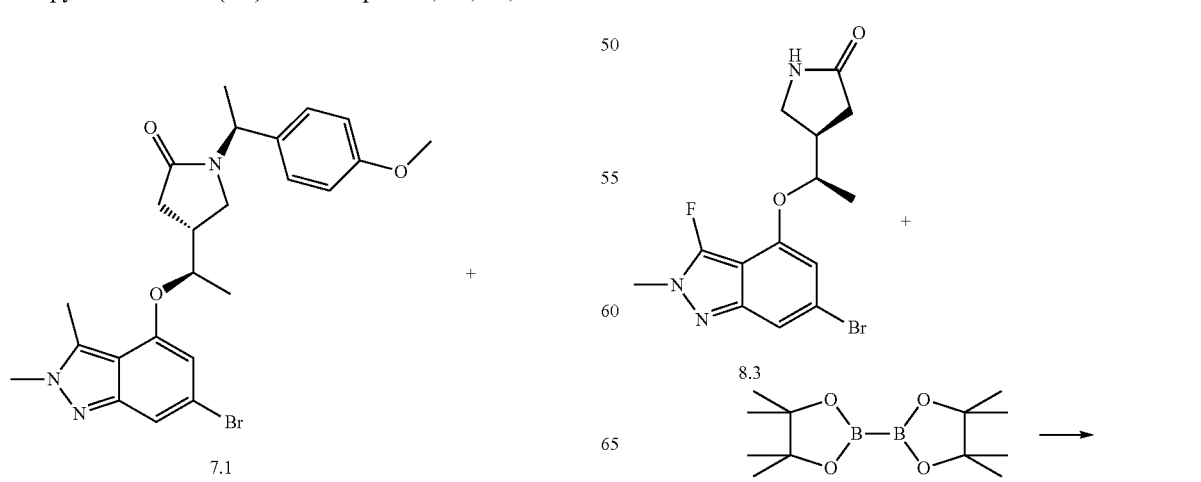

7.1

66

-continued

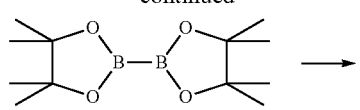

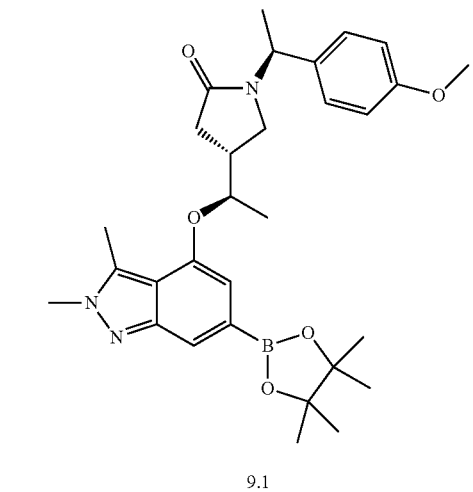

9.1

7.1 (50 mg), bis-(pinacolato)-diboron (31 mg), tetrakis(triphenylphosphine palladium(0) (24 mg) and potassium acetate (30 mg) were suspended in dioxane (2 mL) and the mixture stirred at 100° C. for 1.5 h. The mixture was diluted with DCM (20 mL) and water (20 mL) and the organic phase was separated and concentrated to yield 9.1 (84 mg, content 50%) as oil, which was used in the next step without further purification.

Analysis: HPLC-MS: $R_t$=0.41 (acid)+0.61 (ester, 9.1) min (X016_S01), M+H=452 and 534

Synthesis of (R)-4-{(R)-1-[3-Fluoro-2-methyl-6-(4,4,5,5-tetramethyl-[1,3,2]dioxaborolan-2-yl)-2H-indazol-4-yloxy]-ethyl}-pyrrolidin-2-one (12.1) for Example 12, 14

8.3

-continued

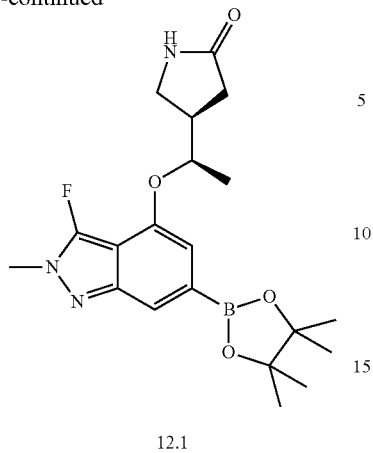

12.1

8.3 (400 mg), bis-(pinacolato)-diboron (342 mg) and potassium acetate (330 mg) and were suspended in dioxane (5 mL) and degassed with nitrogen for 5 min.

(2-Dicyclohexylphosphino-2',4',6'-triisopropyl-1,1'-biphenyl)[2-(2-amino-1,1'-biphenyl)]palladium(II) methanesulfonate (95 mg) was added and the mixture stirred at 75° C. over night after which time it was filtered via Agilent StratoSpheres PL-Thiol MP SPE using MeOH as eluent and concentrated to yield 12.1 (400 mg) as oil which was used without further purification.

Analysis: HPLC-MS: Rt=0.51 min M+H: 404 (method X012_S01).

4.3 Synthesis of the Patent Examples of Formula 1 Via Intermediates with Formula 8-11

Synthesis of (R)-4-{(R)-1-[6-(1-Cyclobutyl-1H-pyrazol-4-yl)-3-fluoro-2-methyl-2H-indazol-4-yloxy]-ethyl}-pyrrolidin-2-one (Example 1)

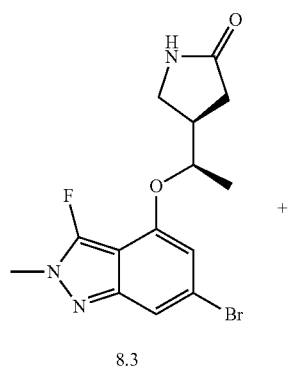

8.3

-continued

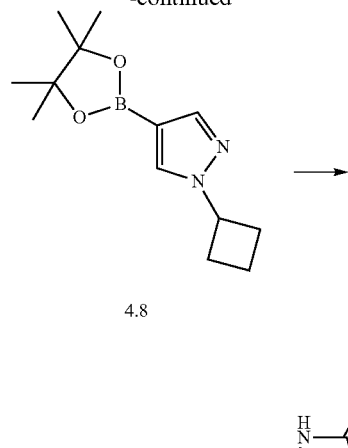

4.8

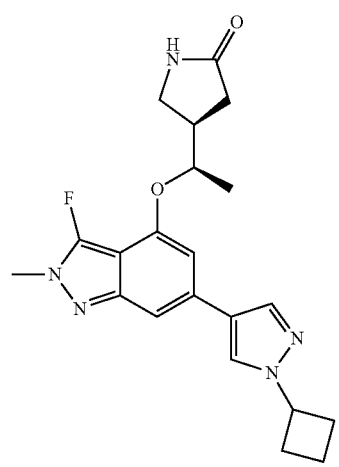

Example 1

To 8.3 (70 mg) in dioxan (1 mL) and 2M aqueous $Na_2CO_3$ (295 μL) was added borolane 4.8 (48.7 mg) and 1,1'-Bis(diphenylphosphino)ferrocenedichloropalladium(II) (A), 7.2 mg) and the mixture was stirred for 45 mins at 70° C. The mixture was filtered via Agilent StratoSpheres PL-Thiol MP SPE using MeOH as eluent and purified via prep HPLC to yield after lyophilisation 43 mg of Example 1.

Analysis: HPLC-MS: $R_t$=0.68 min (001_CA02), M+H=398

$^1$H NMR (DMSO, 400 MHz) b 1.31 (3H, d, J=6.1 Hz), 1.78-1.85 (2H, m), 2.17-2.32 (2H, m), 2.38-2.44 (3H, m), 2.75-2.77 (1H, m), 3.09-3.13 (1H, m), 3.37 (1H, t, J=9.0 Hz), 3.92 (3H, s), 4.73-4.85 (2H, m), 6.66 (1H, s), 7.18 (1H, s), 7.53 (1H, s), 7.96 (1H, s), 8.33 (1H, s)

The following examples were synthesized in anlogous manner to Example 1 using the following palladium catalyst systems:

| Example | formula 8 | Boronic acid/ester (corresponding to formula 4) | Yield catalyst | Analysis |
|---|---|---|---|---|
| Example 2 (R)-4-{(R)-1-[3-Fluoro-6-(1-isopropyl-1H-pyrazol-4-yl)-2-methyl-2H-indazol-4-yloxy]-ethyl}-pyrrolidin-2-one | 8.3 | 1-Isopropyl-4-(4,4,5,5-tetramethyl-1,3,2-dioxaborolan-2-yl)pyrazole 4.6 | 39 mg (51%) A) | HPLC-MS: $R_t$ = 0.64 min (001_CA02)M + H = 386 |

-continued

| Example | Boronic acid/ester (corresponding to formula 8 formula 4) | | Yield catalyst | Analysis |
|---|---|---|---|---|
| Example 4 (R)-4-{(R)-1-[6-(3-tert-Butyl-1H-pyrazol-4-yl)-2,3-dimeth-yl-2H-pyrazolo[4,3-c]pyridin-4-yloxy]-ethyl}-pyrrolidin-2-one | 8.2 | 3-Tert-butyl-1H-pyrazol-4-yl-4-boronic acid 4.2 | 15 mg (32%) B) | HPLC-MS: $R_t$ = 46 min (X012_S01) M + H = 397 $^1$H NMR (DMSO, 400 MHz) δ 1.30 (9H, s), 1.36 (3H, d, J = 6.2 Hz), 2.22-2.35 (2H, m), 2.65 (3H, s) 2.75-2.84 (1H, m), 3.12-3.17 (1H, m), 3.40 (2H, t, J = 9.0 Hz), 3.98 (3H, s), 5.66-5.71 (1H, m), 6.59 (1H, s), 7.42 (1H, s), 7.53 (1H, s) |
| Example 5 (R)-4-{(R)-1-[6-(1-Cycloprop-yl-1H-pyrazol-4-yl)-3-fluoro-2-methyl-2H-indazol-4-yloxy]-ethyl}-pyrrolidin-2-one | 8.3 | 1-Cyclopropyl-4-(4,4,5,5-tetramethyl-[1,3,2] dioxaborolan-2-yl)-1H-pyrazole 4.5 | 44 mg (58%) A) | HPLC-MS: $R_t$ = 0.62 min (001_CA02), M + H = 384 |
| Example 6 (R)-4-{(R)-1-[6-(1-Cycloprop-ylmethyl-1H-pyrazol-4-yl)-3-fluoro-2-methyl-2H-indazol-4-yloxy]-ethyl}-pyrrolidin-2-one | 8.3 | 1-(Cyclopropyl-methyl)-4-(4,4,5,5-tetramethyl-1,3,2-dioxaborolan-2-yl)-1H-pyrazole 4.4 | 47 mg (60%) A) | HPLC-MS: $R_t$ = 0.66 min (001_CA02), M + H = 398 |
| Example 8 (R)-4-{(R)-1-[6-(1-Cyclopropylmethyl-1H-pyrazol-4-yl)-2,3-dimethyl-2H-indazol-4-yloxy]-ethyl}-pyrrolidin-2-one | 8.1 | 1-(Cyclopropyl-methyl)-4-(4,4,5,5-tetra-methyl-1,3,2-dioxaborolan-2-yl)-1H-pyrazole 4.4 | 22 mg (40%) A) | HPLC-MS: $R_t$ = 0.55 min (X011_S03), M + H = 395 |
| Example 13 (R)-4-{(R)-1-[6-(1-tert-Butyl-1H-pyrazol-4-yl)-2,3-dimethyl-2H-indazol-4-yloxy]-ethyl}-pyrrolidin-2-one | 8.1 | 1-tert-Butyl-4-(4,4,5,5-tetramethyl-1,3,2-dioxaborolan-2-yl) pyrazole 4.1 | 120 mg (47%) A) | HPLC-MS: $R_t$ = 0.51 min (X018_S01), M + H = 396 $^1$H NMR (DMSO, 400 MHz) δ 1.32 (3H, d, J = 6.0 Hz), 1.56 (9H, s), 2.20-2.38 (2H, m), 2.63 (3H, s) 2.75-2.85 (1H, m), 3.12-3.16 (1H, m), 3.40 (1H, t, J = 9.1 Hz), 3.94 (3H, s), 4.75-4.80 (1H, m), 6.59 (1H, s), 7.57 (1H, s), 7.89 (1H, s), 8.26 (1H, s) |
| Example 15 (R)-4-{(R)-1-[6-(1-tert-Butyl-1H-pyrazol-4-yl)-2,3-dimethyl-2H-pyrazolo[4,3-c]pyridin-4-yloxy]-ethyl}-pyrrolidin-2-one | 8.2 | 1-tert-Butyl-4-(4,4,5,5-tetramethyl-1,3,2-dioxaborolan-2-yl)pyrazol 4.1 | 630 mg (60%) A) | HPLC-MS: $R_t$ = 0.48 min (X012_S01), M + H = 397 $^1$H NMR (MeOD, 500 MHz) δ 1.47 (3H, d, J = 6.3 Hz), 1.63 (9H, s) 2.54 (2H, dd, J = 8.2, 5.1 Hz), 2.70 (3H, s), 2.88-2.99 (1H, m), 3.36 (1H, dd, J = 10.1, 5.8 Hz), 3.59 (1H, dd, J = 10.0, 8.7 Hz), 4.00 (3H, s), 5.72 (1H, p, J = 6.2 Hz), 7.16 (1H, s), 8.18 (1H, s) |

-continued

| Example | formula 8 | Boronic acid/ ester (corresponding to formula 4) | Yield catalyst | Analysis |
|---|---|---|---|---|
| Example 18 (R)-4-{(R)-1-[6-(1-Isopropyl-1H-pyrazol-4-yl)-2,3-dimethyl-2H-indazol-4-yloxy]-ethyl}-pyrrolidin-2-one | 8.1 | 1-Isopropyl-4-(4,4,5,5-tetramethyl-1,3,2-dioxaborolan-2-yl)pyrazole 4.6 | 430 mg (99%) B) | HPLC-MS: $R_t$ = 0.52 min (X018_S03), M + H = 382 $^1$H NMR (DMSO, 400 MHz) δ 1.32 (3H, d, J = 6.1 Hz), 1.46 (6H, d, J = 6.7 Hz), 2.19-2.37 (2H, m), 2.63 (3H, s), 2.75-2.85 (1H, m), 3.11-3.15 (1H, m), 3.40 (1H, t, J = 9.1 Hz), 3.95 (3H, s), 4.47-4.53 (1H, m), 4.74-4.80 (1H, m), 6.59 (1H, s), 7.20 (1H, s), 7.58 (1H, s), 7.89 (1H, s), 8.23 (1H, s) |
| Example 19 (R)-4-{(R)-1-[6-(1-Isobutyl-1H-pyrazol-4-yl)-2,3-dimethyl-2H-indazol-4-yloxy]-ethyl}-pyrrolidin-2-one | 8.1 | 1-Isobutyl-4-(4,4,5,5-tetramethyl-1,3,2-dioxaborolan-2-yl)-1H-pyrazole 4.10 | 242 mg (98%) B) | HPLC-MS: $R_t$ = 0.43 min (X017_S01), M + H = 396 |
| Example 20 (R)-4-{(R)-1-[6-(1-Cyclopropyl-1H-pyrazol-4-yl)-2,3-dimethyl-2H-indazol-4-yloxy]-ethyl}-pyrrolidin-2-one | 8.1 | 1-Cyclopropyl-4-(4,4,5,5-tetramethyl-[1,3,2]dioxaborolan-2-yl)-1H-pyrazole 4.5 | 23 mg (35%) A) | HPLC-MS: $R_t$ = 0.58 min (003_CA04), M + H = 381 |
| Example 21 (R)-4-{(R)-1-[6-(1-Cyclobutyl-1H-pyrazol-4-yl)-2,3-dimethyl-2H-indazol-4-yloxy]-ethyl}-pyrrolidin-2-one | 8.1 | 1-Cyclobutyl-4-(4,4,5,5-tetramethyl-1,3,2-dioxaborolan-2-yl)-1H-pyrazole 4.8 | 145 mg (65%) B) | HPLC-MS: $R_t$ = 0.57 min (X018_S03), M + H = 394 |

A) 1,1'-Bis(diphenylphosphino)ferrocenedichloropalladium(II) or
B) Dicyclohexyl-[2-(2,4,6-triisopropylphenyl)phenyl]phosphane [2-(2-aminophenyl)phenyl]-methylsulfonyloxy-palladium Example 13 was alternatively synthesized via the following synthesis procedure:

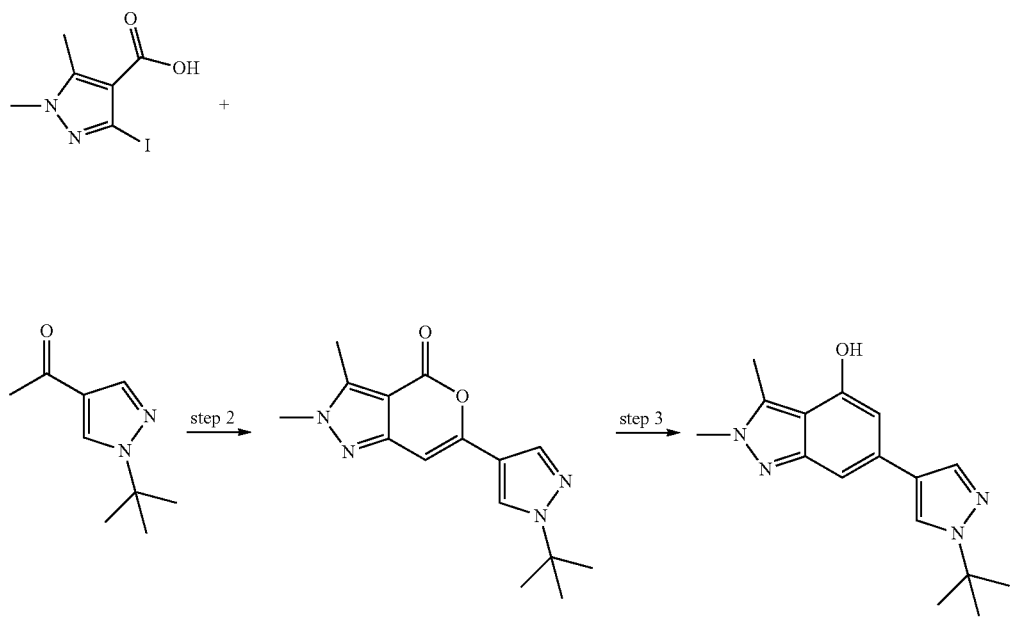

-continued

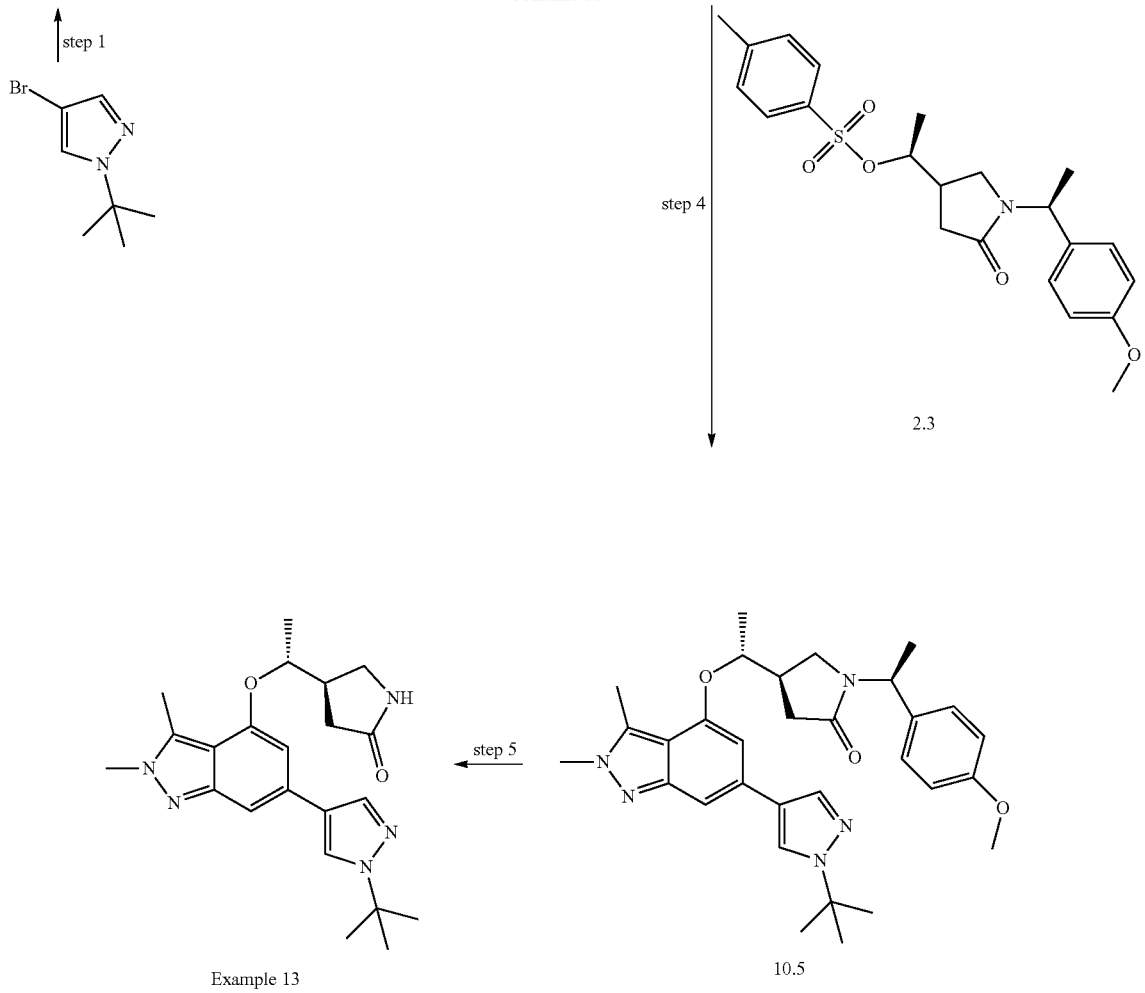

Example 13

Step 1: Isopropyl magnesium chloride lithium chloride complex (1.3 M in THF, 28.4 mL, 37 mmol) was charged to a solution of 4-bromo-1-(tert-butyl)-1H-pyrazole (5.0 g, 25 mmol) in anhydrous THF (25 mL) under argon at ambient temperature. Anhydrous dioxane (3.3 g, 37 mmol) was charged to the reaction, and the reaction was agitated at 45° C. for 4 h. The resulting mixture was cooled to ambient temperature and charged to an anhydrous solution of acetic anhydride (7.5 g, 73 mmol) in THF (25 mL) at −20° C. The resulting mixture was warmed to ambient temperature and concentrated to a residue. The mixture was dissolved in methyl t-butyl ether (50 mL) and washed with water (25 mL). The organic portion was concentrated to provide crude 1-(1-(tert-butyl)-1H-pyrazol-4-yl)ethan-1-one as an oil (7.6 g, 36 wt %) and 67% yield. Crystallization in a mixture of methyl t-butyl ether and heptane provided analytically pure material 1-(1-(tert-Butyl)-1H-pyrazol-4-yl)ethan-1-one. $^1$H NMR (500 MHz, CDCl$_3$) δ=7.96 (s, 1H), 7.86 (s, 1H), 2.37 (s, 3H), 1.55 (s, 9H).

Step 2: Degassed 1,4 dioxane (10 mL) was charged to a mixture of palladium acetate (51 mg, 0.23 mmol), tri-t-butylphosphonium tetrafluoroborate (128 mg, 0.44 mmol), lithium t-butoxide (1.47 g, 18 mmol), 3-iodo-1,5-dimethyl-1H-pyrazole-4-carboxylic acid (1.0 g, 3.7 mmol, Organic Letters (2015), 17(12), 2964-2967) and 1-(1-t-butyl)-1H-pyrazole-4-yl)ethan-1-one (0.68 g, 4.1 mmol) at ambient temperature under argon. The agitated mixture was heated to 80° C. over approximately 15 min and stirred at this temperature for 30 min. The reaction was cooled to ambient temperature and diluted with trifluoroacetic acid (30 ml) and acetonitrile (15 mL). The mixture was agitated at 78° C. for 10 h. The reaction was cooled to ambient temperature and concentrated to a solid residue. The residue was dissolved in a mixture of isopropyl acetate and water. The aqueous layer pH was adjusted to pH ~10 with 3M NaOH.

The layers were separated, and the organic portion was washed twice with water. The organic portion was concentrated to a solid (1.92 g). The solid was dissolved in hot n-propanol (7 mL) and cooled to ambient temperature wherein crystallization occurred. The mixture was diluted with water (10 mL) dropwise and agitated for 30 min. The solids were collected by filtration and washed with a solution of 20 vol % n-propanol in water. The solids were dried in a vacuum oven at 50° C. with a nitrogen stream to provide 6-(1-(tert-butyl)-1H-pyrazol-4-yl)-2,3-dimethylpyrano[4,3-c]pyrazol-4(2H)-one as a solid in ~94 wt % purity (49% yield). $^1$H NMR (CDCl$_3$, 400 MHz), δ=7.96 (s, 1H), 7.83 (s, 1H), 6.61 (s, 1H), 3.89 (s, 3H), 2.66 (s, 3H), 1.62 (s, 9H).

Step 3: Dimethyl methylphosphonate (1.2 g, 10 mmoL) was charged dropwise to an anhydrous slurry of lithium diisopropyl amide (2.0 M, 4.6 mL, 9.2 mmol) in THF (15 mL) at −78° C. under argon. After agitation for 50 min, an anhydrous slurry of 6-(1-(tert-butyl)-1H-pyrazol-4-yl)-2,3-dimethylpyrano[4,3-c]pyrazol-4(2H)-one (0.89 g, 3.11 mmol) in THF (10 mL) was charged to the above lithiated phosphonate solution at −78° C. The reaction mixture was agitated at −78° C. for 1 h and allowed to warm to ambient temperature over 1 h. The reaction was quenched with methanol (3 mL) and agitated for 1 h. Aqueous 3 M HCl (4 mL) was charged to the reaction, and the reaction was agitated overnight at ambient temperature. The reaction was diluted with water (15 mL) and concentrated in vacuo to remove the organic solvents. The resulting slurry was diluted with isopropyl acetate and water. The aqueous layer pH was adjusted to 3-4 with 3 M HCl. The layers were separated, and the aqueous portion was back extracted with isopropyl acetate. The combined organic layers were concentrated to a solid in vacuo. The solid was dissolved in hot n-propanol (6 mL), cooled to ambient temperature and diluted with water (35 mL) dropwise with stirring. The mixture was agitated for 1 h at ambient temperature. The solids were collected by filtration washed with water, and dried in a vacuum oven at 50° C. with a nitrogen stream to provide 6-(1-(tert-butyl)-1H-pyrazol-4-yl)-2,3-dimethyl-2H-indazol-4-ol (760 mg, 84 wt %, 72% yield). $^1$H NMR (DMSO-d6, 400 MHz), δ=9.86 (s, 1H), 8.11 (s, 1H), 7.75 (s, 1H), 7.11 (s, 1H), 6.41 (s, 1H), 3.94 (s, 3H), 2.67 (s, 3H), 1.55 (s, 9H).

Step 4: A mixture of potassium carbonate (610 mg, 4.4 mmol), (S)-1-((R)-1-((S)-1-(4-methoxyphenyl)ethyl)-5-oxopyrrolidin-3-yl)ethyl 4-methylbenzenesulfonate (810 mg, 1.9 mmol), and 6-(1-(tert-butyl)-1H-pyrazol-4-yl)-2,3-dimethyl-2H-indazol-4-ol (418 mg, 1.5 mmol) in anhydrous dimethyl formamide (1.5 mL) were agitated under nitrogen at 70° C. for 18 h. Additional (S)-1-((R)-1-((S)-1-(4-methoxyphenyl)ethyl)-5-oxopyrrolidin-3-yl)ethyl 4-methylbenzenesulfonate (0.280 mg, 0.66 mmol) was charged to the reaction, and the reaction was agitated at 70° C. for 20 h. The reaction was diluted with isopropyl acetate and water. The layers were separated, and the organic portion was washed twice. The organic portion was concentrated to an oily solid. Purification by silica gel chromatography (Methanol in ethyl acetate) provided the intended product (R)-4-((R)-1-((6-(1-(tert-butyl)-1H-pyrazol-4-yl)-2,3-dimethyl-2H-indazol-4-yl)oxy)ethyl)-1-((S)-1-(4-methoxyphenyl)ethyl)pyrrolidin-2-one (10.5) as a foam in approximately 90% purity (769 mg, 89%). $^1$H NMR (CDCl$_3$, 500 MHz), δ=7.77 (s, 1H), 7.72 (s, 1H), 7.24 (s, 1H), 7.15 (d, J=8.74 Hz, 2H), 6.23 (d, J=8.54 Hz, 2H), 6.26 (s, 1H), 5.46 (q, J=7.41 Hz, 1H), 4.50-4.56 (m, 1H), 3.97 (s, 3H), 3.69 (s, 3H), 3.48 (t, J=9.0 Hz, 1H), 2.93-3.0 (m, 1H), 2.62-2.80 (m, 2H), 2.55-2.62 (m, 1H), 2.48 (s, 3H), 1.64 (s, 9H), 1.50 (d, J=7.4 Hz, 3H), 1.31 (d, J=6.3 Hz, 3H).

Step 5: A solution of (R)-4-((R)-1-((6-(1-(tert-butyl)-1H-pyrazol-4-yl)-2,3-dimethyl-2H-indazol-4-yl)oxy)ethyl)-1-((S)-1-(4-methoxyphenyl)ethyl)pyrrolidin-2-one (585 mg, 1.1 mmol) in trifluoroacetic acid (3 mL) and anisole (1.5 mL) was agitated at 75° C. under nitrogen for 18 h. The reaction was cooled to ambient temperature and diluted with isopropyl acetate and water. The aqueous portion pH was adjusted to 6 with aqueous 3M NaOH. The layers were separated and the organic portion was concentrated to an oil. Purification by silica gel chromatography (EtOH in EtOAc) provided example 13 as a foam (420 mg, 94%).

Synthesis of (R)-5-{(R)-1-[6-(1-tert-Butyl-1H-pyrazol-4-yl)-2,3-dimethyl-2H-pyrazolo[4,3-c]pyridin-4-yloxy]-ethyl}-oxazolidin-2-one (Example 3)

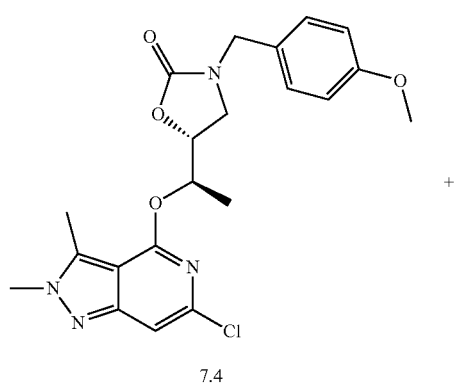

7.4

+

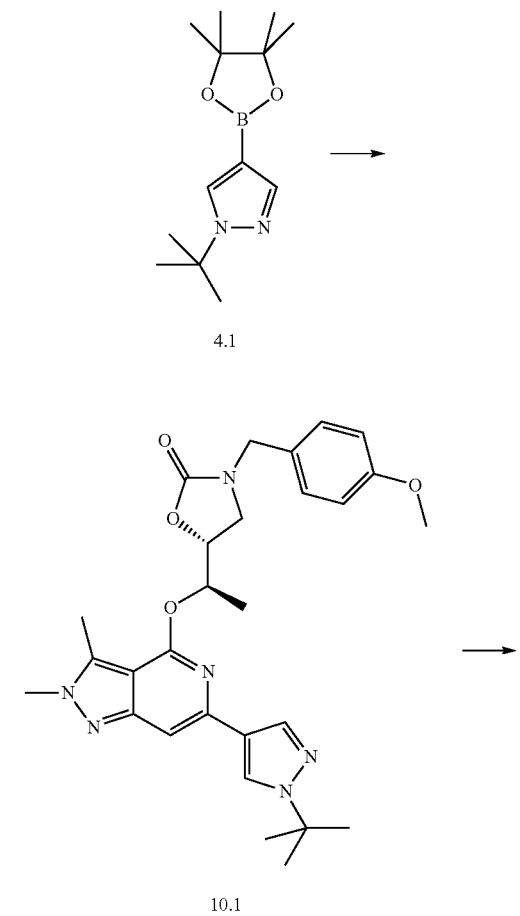

4.1

10.1

-continued

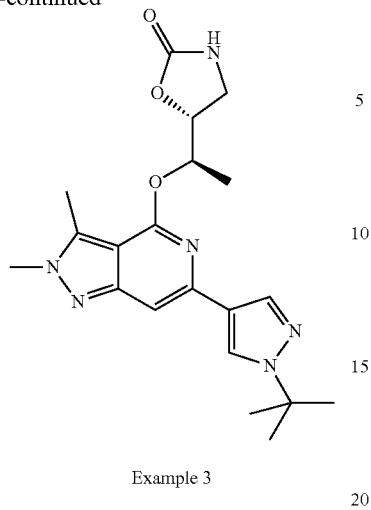

Example 3

Step 1: To 4.1 (46 mg) and dicyclohexyl-[2-(2,4,6-triiso-propylphenyl) phenyl]phosphane [2-(2-aminophenyl)phenyl]-methylsulfonyloxy-palladium (15 mg) was added 7.4 (38 mg), dissolved in dioxane (1 mL) and MeOH (0.2 mL) and 2M aqueous $Na_2CO_3$ (0.175 mL), and the mixture was heated for 50 mins at 90° C. After which time MeOH (10 mL) was added and the mixture was filtered via Agilent StratoSpheres PL-Thiol MP SPE and concentrated. The residual was dissolved in DCM (20 mL) and extracted with water (20 mL) and the water phase extracted with DCM (10 mL). The combined organic phases were dried and concentrated to yield 10.1 (74 mg) which was used without further purification for the next step.

Analysis: HPLC-MS: $R_t$=0.86 min (X018_S03), M+H=519

Step 2: To 10.1 (74 mg) was added trifluoracetic acid (2.956 g) and the mixture was stirred for 30 h at 75° C. The mixture was then concentrated and purified via prep HPLC (water/acetonitrile/$NH_3$) to provide a white solid which was then separated via Chiral SFC (Knauer Eurocel 01; 80% $scCO_2$/20% MeOH+20 mM $NH_3$; 120 bar BPR; 40° C. to provide Example 3 (13 mg) as white solid.

Analysis: HPLC-MS: $R_t$=0.92 min (V011_S01), M+H=399

Synthesis of (R)-4-((R)-1-{6-[1-((R)-2,2-Dimethyl-tetrahydro-pyran-4-yl)-1H-pyrazol-4-yl]-2,3-dimethyl-2H-indazol-4-yloxy}-ethyl)-pyrrolidin-2-one (Example 9)

-continued

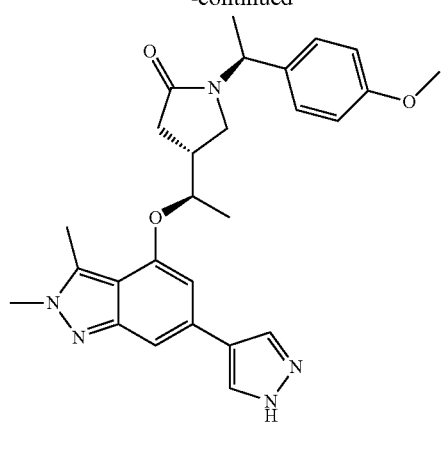

11.1

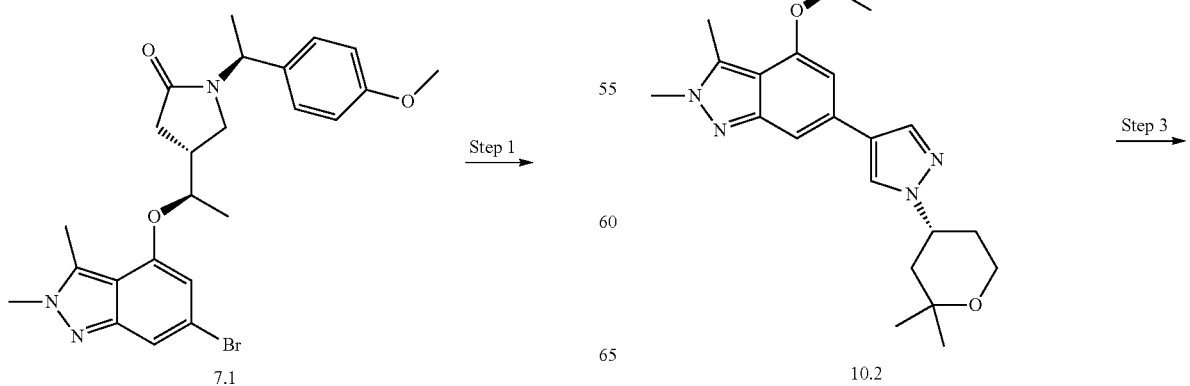

-continued

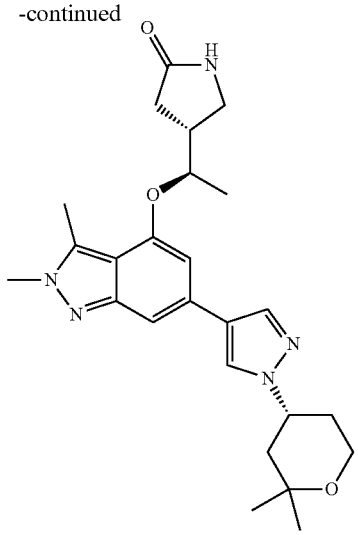

Example 9

Step 1: To 7.1 (200 mg), 4-(4,4,5,5-Tetramethyl-[1,3,2] dioxaborolan-2-yl)-1H-pyrazole 4.9 (120 mg), Dicyclohexyl-[2-(2,4,6-triisopropylphenyl)phenyl]phosphane [2-(2-aminophenyl) phenyl]-methylsulfonyloxy-palladium (40 mg) was added dioxane (3 mL) and 2M aqueous $Na_2CO_3$ (0.7 mL) and the mixture was stirred for 2 h at 90° C. The mixture was diluted with DCM (50 mL) and water (30 mL). After phase separation the water phase was extracted 2× with DCM (25 mL). The combined organic phases were dried ($MgSO_4$) and purified via prep HPLC to provide 11.1 as yellow oil (137 mg).

Analysis: HPLC-MS: $R_t$=0.44 min (X012_S01), M+H=474

Step 2: To 5.2 (61 mg) and $Cs_2CO_3$ (93 mg) was added 11.1 (68 mg) dissolved in DMF (1 mL) and the suspension was heated to 70° C. for 3 h. Additional 5.2 (45 mg) and $Cs_2CO_3$ (93 mg) was added and stirring continued for 5 h at 70° C., then further 5.2 (45 mg) and $Cs_2CO_3$ (93 mg) was added and stirring continued at 80° C. for 10 h and 3 days at ambient temperature. The mixture was diluted with DCM (20 mL) and water (20 mL) and the phases were separated. The water phase was extracted with DCM (20 mL) and the combined organic phases were dried, concentrated and purified via prep HPLC to provide 10.2 (57 mg) as colorless oil.

Analysis: HPLC-MS: $R_t$=0.65 min (X012_S01), M+H=586

Step 3: To 10.2 (57 mg) was added trifluoracetic acid (2 mL) and the mixture was stirred for 3 h at 80° C. The mixture was concentrated and purified via prep HPLC to provide Example 9 (23.7 mg)

Analysis: HPLC-MS: $R_t$=0.90 min (003_CA03), M+H=452

Synthesis of 4-(1-{6-[(R)-(3S,3aR,7aR)-1-(Hexahydro-furo[3,2-b]pyran-3-yl)-1H-pyrazol-4-yl]-2,3-dimethyl-2H-indazol-4-yloxy}-ethyl)-pyrrolidin-2-one (Example 10)

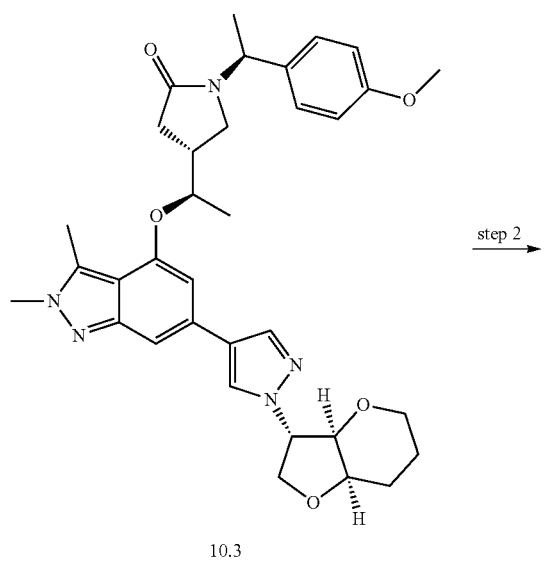

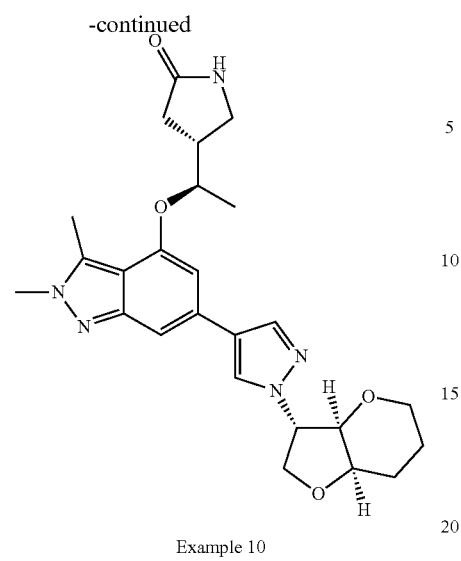

Example 10

Step 1: To 5.1 (64 mg) and Cs₂CO₃ (93 mg) was added 11.1 (68 mg) dissolved in DMF (1 mL) and the suspension was heated to 70° C. for 3 h. Additional 5.1 (45 mg) and Cs₂CO₃ (93 mg) was added and stirring continued for 5 h at 70° C., then further 5.1 (45 mg) and Cs₂CO₃ (93 mg) was added and stirring continued at 80° C. for 10 h and 3 days at ambient temperature and 3 h at 100° C. The mixture was diluted with DCM (20 mL) and water (20 mL) and the phases were separated. The water phase was extracted with DCM (20 mL) and the combined organic phases were dried, concentrated and purified via prep HPLC to provide 10.3 (42 mg) as colorless oil.

Analysis: HPLC-MS: $R_t$=0.64 min (X012_S01), M+H=600

Step 2: To 10.3 (41 mg) was added trifluoracetic acid (2 mL) and the mixture was stirred for 3 h at 80° C. The mixture was concentrated and purified via prep HPLC to provide Example 10 (17.1 mg).

Analysis: HPLC-MS: $R_t$=0.88 min (003_CA03), M+H=466

Synthesis of (R)-4-((R)-1-{6-[1-(2-Fluoro-ethyl)-1H-pyrazol-4-yl]-2,3-dimethyl-2H-indazol-4-yloxy}-ethyl)-pyrrolidin-2-one (Example 11)

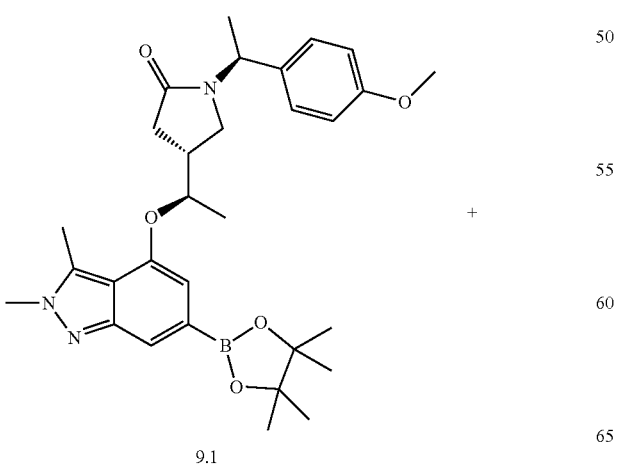

9.1

+

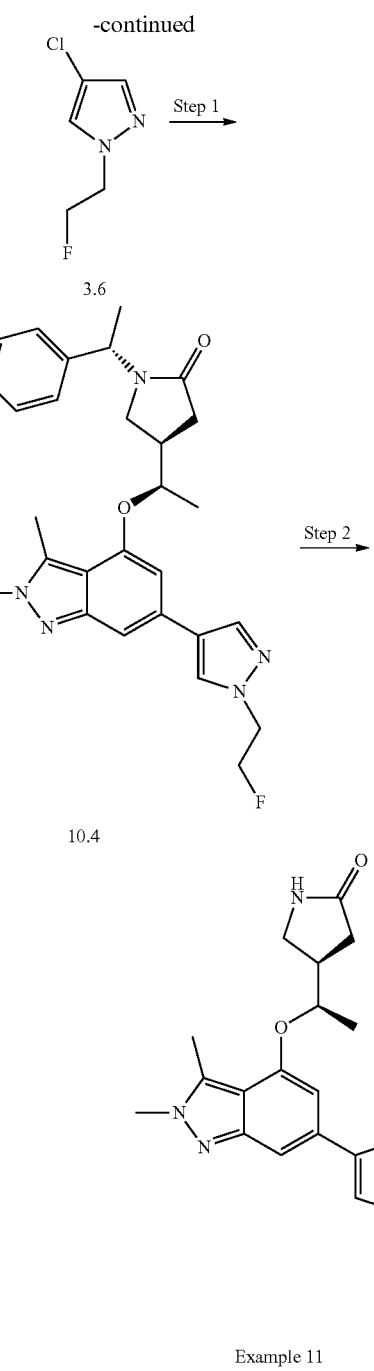

To 9.1 (150 mg), 3.6 (35 mg) and Dicyclohexyl-[2-(2,4,6-triisopropylphen-yl)phenyl]phosphane [2-(2-aminophenyl)phenyl]-methylsulfonyloxy-palladium (17 mg) in dioxan (1 mL) and 2M aqueous Na₂CO₃ (394 µL) was heated for 3 h mins at 100° C. Water was added and the water phase was extracted 3× with DCM and the combined organic phases concentrated, dissolved in MeOH and filtered via Agilent StratoSpheres PL-Thiol MP SPE and concentrated to provide 10.4 which was used without further purification for the next step.

Analysis: HPLC-MS: $R_t$=0.53 min (X011_S03), M+H=520

Step 2: To 10.4 (107 mg) was added trifluoracetic acid (1.5 mL) and heated for 2.5 h at 70° C. To the mixture was added water and sat aqueous NaHCO₃ and the water phase was extracted 2× with DCM. The combined organic phases were concentrated and purified via prep HPLC to provide Example 11 (12 mg) as white solid.

Analysis: HPLC-MS: $R_t$=0.41 min (X011_S03), M+H=386

$^1$H NMR (DMSO, 400 MHz) δ 1.32 (3H, d, J=6.0 Hz), 2.19-2.37 (2H, m), 2.63 (3H, s), 2.75-2.84 (1H, m), 3.11-3.15 (1H, m), 3.40 (1H, t, J=9.1 Hz), 3.94 (3H, s), 4.40 (1H, t, J=4.7 Hz), 4.47 (1H, t, J=4.7 Hz), 4.73-4.78 (2H, m), 4.86 (1H, t, J=4.7 Hz), 6.56 (1H, s), 7.20 (1H, s), 7.56 (1H, s), 7.96 (1H, s), 8.23 (1H, s)

The following Examples were synthesized in analogous manner to Example 11 using intermediate 9.1 and one of the following palladium catalyst systems:

| Example | Bromide (corresponding to formula 3) | Yield A) or B) | Analysis |
|---|---|---|---|
| Example 16 (R)-4-((R)-1-{2,3-Dimethyl-6-[1-(2,2,5,5-tetramethyl-tetrahydro-furan-3-yl)-1H-pyrazol-4-yl]-2H-indazol-4-yloxy}-ethyl)-pyrrolidin-2-one | 4-Bromo-1-(2,2,5,5-tetramethyl-tetrahydro-furan-3-yl)-1H-pyrazole 3.2 | 27 mg (41%) (two steps) B) | HPLC-MS: $R_t$ = 0.70 min (003_CA04), M + H = 466 $^1$H NMR (DMSO, 400 MHz) δ 0.77 (3H, d, J = 1.1 Hz), 1.27 (3H, s), 1.33 (3H, d, J = 6.0 Hz), 1.37 (6H, s), 2.20-2.38 (3H, m), 2.64 (3H, s), 2.76-2.85 (2H, m), 3.11-3.15 (1H, m), 3.38-3.42 (1H, m), 3.95 (3H, s), 4.74-4.81 (2H, m), 6.66 (1H, s), 7.24 (1H, s), 7.56 (1H, s), 7.97 (1H, s), 8.34 (1H, d, J = 4.0 Hz) |
| Example 17 2-(4-{2,3-Dimethyl-4-[(R)-1-((R)-5-oxo-pyrrolidin-3-yl)-ethoxy]-2H-indazol-6-yl}-pyrazol-1-yl)-2-methyl-propionitrile | 2-(4-Bromo-pyrazol-1-yl)-2-methyl-propionitrile 3.3 | 6 mg (9%) (two steps) A) | HPLC-MS: $R_t$ = 0.41 min (X012_S01), M + H = 407 |
| Example 22 (R)-4-((R)-1-{6-[1-(3,3-Difluoro-cyclopentyl)-1H-pyrazol-4-yl]-2,3-dimethyl-2H-indazol-4-yloxy}-ethyl)-pyrrolidin-2-one | 4-Bromo-1-(3,3-difluoro-cyclopentyl)-1H-pyrazole 3.4 | 80 mg (35%) B) | HPLC-MS: $R_t$ = 0.592 min (X018_S03), M + H = 444 |

A) 1,1'-Bis(diphenylphosphino)ferrocenedichloropalladium(II) or
B) Dicyclohexyl-[2-(2,4,6-triisopropylphenyl)phenyl]phosphane [2-(2-aminophenyl)phenyl]-methylsulfonyloxy-palladium Synthesis of (R)-4-((R)-1-{3-Fluoro-2-methyl-6-[1-(3,3,3-trifluoro-propyl)-1H-pyrazol-4-yl]-2H-indazol-4-yloxy}-ethyl)-pyrrolidin-2-one (Example 12)

To 12.1 (40 mg), 3.5 (19 mg) and 1,1'-Bis(diphenylphosphino)ferrocenedichloropalladium(II) (2.9 mg) in dioxane (1 mL) and 2M aqueous Na₂CO₃ (119 μL) was heated over night at 45° C. The mixture was diluted with MeOH and filtered via Agilent StratoSpheres PL-Thiol MP SPE, concentrated and purified via prep HPLC to provide Example 12 (8 mg).

Analysis: HPLC-MS: $R_t$=0.48 min (X011_S03), M+H=440

$^1$H NMR (DMSO, 400 MHz) b 1.31 (3H, d, J=6.1 Hz), 2.17-2.32 (2H, m), 2.71-2.81 (1H, m), 2.85-2.98 (2H, m), 3.09-3.13 (1H, m), 3.37 (1H, t, J=901 Hz), 3.92 (3H, d, J=1.2 Hz), 4.39 (2H, t, J=6.9 Hz), 4.70-4.76 (1H, m), 6.63 (1H, s), 7.17 (1H, s), 7.53 (1H, s), 8.00 (1H, s), 8.32 (1H, s)

The following Example 14 was synthesized in analogous manner to Example 12

| Example | Bromide (corresponding to formula 3) | Yield | Analysis |
|---|---|---|---|
| Example 14 (R)-4-((R)-1-{3-Fluoro-2-methyl-6-[1-(2,2,5,5-tetramethyl-tetrahydro-furan-3-yl)-1H-pyrazol-4-yl]-2H-indazol-4-yloxy}-ethyl)-pyrrolidin-2-one | 4-Bromo-1-(2,2,5,5-tetramethyl-tetrahydro-furan-3-yl)-1H-pyrazole 3.2 | 22 mg (24%) | HPLC-MS: $R_t$ = 0.54 min (X011_S03), M + H = 470 |

4.5 Analytical Methods

The Example compounds prepared according to the foregoing synthesis schemes were characterised by the following chromatographic methods and/or NMR spectroscopy.

4.5.1 Chromatographic Methods (HPLC-MS Methods)

Method A

| Column: | Xbridge BEH C18, 2.1 × 30 mm, 1.7 μm |
| Column supplier: | Waters |

| Gradient/ Solvent Time [min] | % Sol [H₂O, 0.1% NH₃] | % Sol [Acetonitril] | Flow [ml/min] | Temp [°C.] |
|---|---|---|---|---|
| 0.00 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

Method B:

| Column: | Sunfire C18, 3 × 30 mm, 2.5 μm |
| Column Supplier: | Waters |

| Gradient/Solvent Time [min] | % Sol [H₂O, 0.1% TFA] | % Sol [Methanol] | Flow [ml/min] | Temp [°C.] |
|---|---|---|---|---|
| 0.0 | 95 | 5 | 1.8 | 60 |
| 0.25 | 95 | 5 | 1.8 | 60 |
| 1.70 | 0 | 100 | 1.8 | 60 |
| 1.75 | 0 | 100 | 2.5 | 60 |
| 1.90 | 0 | 100 | 2.5 | 60 |

Method E:

| Column: | Sunfire C18, 2.1 × 20 mm, 2.5 μm |
| Column Supplier: | Waters |

| Gradient/Solvent Time [min] | % Sol [H₂O, 0.10%TFA] | % Sol [Methanol] | Flow [ml/min] | Temp [° C.] |
|---|---|---|---|---|
| 0.00 | 99 | 1 | 1.3 | 60 |
| 0.15 | 99 | 1 | 1.3 | 60 |
| 1.10 | 0 | 100 | 1.3 | 60 |
| 1.25 | 0 | 100 | 1.3 | 60 |

Method F:

| Column: | XBridge C18, 3 × 30 mm, 2.5 µm | | | |
|---|---|---|---|---|
| Column Supplier: | Waters | | | |
| Gradient/Solvent Time [min] | % Sol [H$_2$O, 0.1% NH] | % Sol [Acetonitril] | Flow [ml/min] | Temp [°C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method H:
Eluent A: Hexane
Eluent B: 2-Propanol

| Time [min] | % A | % B | Flow rate [mL/min] |
|---|---|---|---|
| 00.00 | 90 | 10 | 1.0 |
| 20.00 | 90 | 10 | 1.0 |

The stationary phase used was a Chiralpak AD-H (Daicel), 5 µm; dimension: 150×4.6 mm, (column temperature: constant at 10° C.). Detection DAD 225 nm.

Method I:
Eluent A: Hexane
Eluent B: 2-Propanol

| Time [min] | % A | % B | Flow rate [mL/min] |
|---|---|---|---|
| 00.00 | 90 | 10 | 1.0 |
| 25.00 | 90 | 10 | 1.0 |

The stationary phase used was a Chiralpak AD-H (Daicel), 5 µm; dimension: 150×4.6 mm, (column temperature: constant at 10° C.).

Detection DAD 225 nm.

Method J:

| Column: | Sunfire C18, 2.1 × 30 mm, 2.5 µm | | | |
|---|---|---|---|---|
| Column Supplier: | Waters | | | |
| Gradient/Solvent Time [min] | % Sol [H$_2$O, 0.1% TFA] | % Sol [Acetonitril] | Flow [ml/min] | Temp [° C.] |
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

Method X018_S03

| Column: | Sunfire C18, 3.0 × 30 mm, 2.5 µm | | | |
|---|---|---|---|---|
| Column Supplier: | Waters | | | |
| Gradient/Solvent Time [min] | % Sol [H$_2$O, 0.1% TFA] | % Sol [Acetonitril] | Flow [ml/min] | Temp [° C.] |
| 0.0 | 95 | 5 | 1.5 | 60 |
| 1.3 | 0 | 100 | 1.5 | 60 |
| 1.5 | 0 | 100 | 1.5 | 60 |

Method X018_S01

| Column: | Sunfire C18, 2.1 × 30 mm, 2.5 µm | | | |
|---|---|---|---|---|
| Column Supplier: | Waters | | | |
| Gradient/Solvent Time [min] | % Sol [H$_2$O, 0.1% TFA] | % Sol [Acetonitril] | Flow [ml/min] | Temp [° C.] |
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

Method X011_S03

| Säule: | Xbridge BEH C18, 2.1 × 30 mm, 1.7 µm | | | |
|---|---|---|---|---|
| Säulen-Hersteller: | Waters | | | |
| Verlauf/Löslichkeit Zeit [min] | % Sol [H2O, 0.1% NH3] | % Sol [Acetonitril] | Flow [ml/min] | Temp [° C.] |
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method X012_S01

| Method Name: | X012_S01 |
|---|---|
| Method Name: | X012_S01 |
| Column: | Xbridge BEH C18, 2.1 × 30 mm, 1.7 µm |
| Column Supplier: | Waters |

| Gradient/Solvent Time [min] | % Sol [H2O, 0.1% TFA] | % Sol [Acetonitril] | Flow [ml/min] | Temp [° C.] |
|---|---|---|---|---|
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

Method X012_S02

| Method Name: | X012_S02 |
|---|---|
| Column: | Xbridge BEH C18, 2.1 × 30 mm, 1.7 µm |
| Column Supplier: | Waters |

| Gradient/Solvent Time [min] | % Sol [H2O, 0.1% TFA] | % Sol [Acetonitril] | Flow [ml/min] | Temp [° C.] |
|---|---|---|---|---|
| 0.0 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

Method X016_S01

| Method Name: | X016_S01 |
|---|---|
| Column: | Xbridge BEH Phenyl, 2.1 × 30 mm, 1.7 µm |
| Method Name: | X016_S01 |
| Column Supplier: | Waters |

| Gradient/Solvent Time [min] | % Sol [H2O, 0.1% TFA] | % Sol [Acetonitril] | Flow [ml/min] | Temp [° C.] |
|---|---|---|---|---|
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

Method X017_S01

| Column: | Zorbax Stable Bond C18, 2.1 × 30 mm, 1.8 µm |
| --- | --- |
| Column Supplier: | Waters |

| Gradient/Solvent Time [min] | % Sol [H2O, 0.1% TFA] | % Sol [Acetonitril] | Flow [ml/min] | Temp [° C.] |
| --- | --- | --- | --- | --- |
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

Method P:

Column: Supelco Ascentis Express (2.1×30 mm, 2.7 µm column)

Flow rate: 1 ml/min

Solvent A: 0.1% Formic acid/water

Solvent B: 0.1% Formic acid/acetonitrile

Injection volume: 3 µL

Column temperature: 40° C.

UV Detection wavelength: 215 nm

Eluent: 0 to 1.5 minutes, constant gradient from 95% solvent A+5% solvent B to 100% solvent B; 1.5 to 1.6 minutes, 100% solvent B; 1.60 to 1.61 minutes, constant gradient from 100% solvent B to 95% solvent A+5% solvent B; 1.61 to 2.00 minutes, 95% solvent A+5% solvent B.

MS detection using Waters LCT Premier, QTof micro, ZQ or Shimadzu LCMS2010EV UV detection using Waters 2996 photodiode array, Waters 2998 photodiode array, Waters 2487 UV or Shimadzu SPD-M20A PDA Method 001_CA02

| Column: | SunFire C18_3.0 × 30 mm, 2.5 µm |
| --- | --- |
| Column Supplier: | Waters |
| Description: | Waters Acquity, QDa Detector |

| Gradient/Solvent Time [min] | % Sol [Acetonitrile 0.08% TFA] | Flow [ml/min] | Temp [° C.] |
| --- | --- | --- | --- |
| 0.0 | 5.0 | 1.5 | 40.0 |
| 1.3 | 100.0 | 1.5 | 40.0 |
| 1.5 | 100.0 | 1.5 | 40.0 |
| 1.6 | 5.0 | 1.5 | 40.0 |

Method 003_CA03

| Device description: | Agilent 1100 with DAD, CTC Autosampler and Waters MS-Detector |
| --- | --- |
| Column: | Sunfire C18_3.0 × 30 mm_3.5 µm |
| Column producer: | Waters |
| Description: | |

| Gradient/Solvent Time [min] | % Sol [H2O 0.1% TFA] | % Sol [Acetonitrile] | Flow [ml/min] | Temp [° C.] |
| --- | --- | --- | --- | --- |
| 0.0 | 98.0 | 2.0 | 2.0 | 60.0 |
| 0.3 | 98.0 | 2.0 | 2.0 | 60.0 |
| 1.5 | 0.0 | 100.0 | 2.0 | 60.0 |
| 1.6 | 0.0 | 100.0 | 2.0 | 60.0 |

Method 003_CA04

| Device description: | Agilent 1100 with DAD, CTC Autosampler and Waters MS-Detector |
| --- | --- |
| Column: | XBridge C18_3.0 × 30 mm, 2.5 µm |
| Column producer: | Waters |

| Gradient/Solvent Time [min] | % Sol [H2O 0.1% NH4OH] | % Sol [Acetonitrile] | Flow [ml/min] | Temp [° C.] |
| --- | --- | --- | --- | --- |
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

Method Z001_005

| Column: | XBridge C18, 3 × 30 mm, 2.5 µm |
| --- | --- |
| Column Supplier: | Waters |

| Gradient/Solvent Time [min] | % Sol [H2O, 0.1% TFA] | % Sol [Methanol] | Flow [ml/min] | Temp [° C.] |
| --- | --- | --- | --- | --- |
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

Method Z018_S03

| Column: | Sunfire, 3 × 30 mm, 2.5 µm |
| --- | --- |
| Column Supplier: | Waters |

| Gradient/Solvent Time [min] | % Sol [H2O, 0.1% TFA] | % Sol [Acetonitril] | Flow [ml/min] | Temp [° C.] |
| --- | --- | --- | --- | --- |
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

Method Z018_S04

| Column: | Sunfire, 3 × 30 mm, 2.5 µm |
| --- | --- |
| Column Supplier: | Waters |

| Gradient/Solvent Time [min] | % Sol [H2O, 0.1% TFA] | % Sol [Acetonitril] | Flow [ml/min] | Temp [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method V011_S01

| Column: | XBridge C18, 4.6 × 30 mm, 3.5 µm |
| --- | --- |
| Column Supplier: | Waters |

| Gradient/Solvent Time [min] | % Sol [H2O, 0.1% NH3] | % Sol [ACN] | Flow [ml/min] | Temp [° C.] |
| --- | --- | --- | --- | --- |
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

Method X018_S02

| Method Name: | | | | |
| --- | --- | --- | --- | --- |
| Column: | Sunfire C18, 2.1 × 30 mm, 2.5 μm | | | |
| Column Supplier: | Waters | | | |
| Gradient/Solvent Time [min] | % Sol [H2O, 0.1% TFA] | % Sol [Acetonitril] | Flow [ml/min] | Temp [° C.] |
| 0.0 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

Method G:
Eluent A: Water/0.2% $KH_2PO_4$ pH=3
Eluent B: Acetonitrile

| Time [min] | % A | % B | Flow rate [mL/min] |
| --- | --- | --- | --- |
| 0.00 | 80 | 20 | 1.50 |
| 5.00 | 20 | 80 | 1.50 |
| 8.00 | 20 | 80 | 1.50 |

The stationary phase used was a Inertsil C8-3 (GL Sciences), 5 μm; dimension: 100×4.0 mm,
(column temperature: constant at 30° C.). Detection UV 220 nm.

4.5.2 NMR Spectroscopy

Configuration of the Bruker DRX 500 MHz NMR

High performance digital NMR spectrometer, 2-channel microbay console and Windows XP host workstation running Topspin version 1.3.

Equipped with:
Oxford instruments magnet 11.74 Tesla (500 MHz proton resonance frequency)
B-VT 3000 temperature controller
GRASP II gradient spectroscopy accessory for fast acquisition of 2D pulse sequences
Deuterium lock switch for gradient shimming
5 mm Broad Band Inverse geometry double resonance probe with automated tuning and matching (BBI ATMA). Allows $^1H$ observation with pulsing/decoupling of nuclei in the frequency range $^{15}N$ and $^{31}P$ with $^2H$ lock and shielded z-gradient coils.

Configuration of the Bruker DPX 400 MHz NMR

High performance one bay Bruker 400 MHz digital two channel NMR spectrometer console and Windows XP host workstation running XwinNMR version 3.5.

Equipped with:
Oxford instruments magnet 9.39 Tesla (400 MHz proton resonance frequency)
B-VT 3300 variable temperature controller unit
Four nucleus (QNP) switchable probe for observation of $^1H$, $^{13}C$, $^{19}F$ and $^{31}P$ with $^2H$ lock Configuration of the Bruker 500 MHz NMR High performance digital NMR spectrometer, 2-channel one bay console and Linux host workstation running Topspin version 2.1 PL6.

Equipped with:
Bruker-Biospin AVANCE III 500A magnet 11.75 Tesla (500 MHz proton resonance frequency)
B-VT 3000 temperature controller
5 mm Multinuclear Broad Band fluorine observe (BBFO) probe with digital tuning covering the range from $^{15}N$ and $^{31}P$ as well as $^{19}F$ with $^1H$ decoupling.

Configuration of the Bruker DPX 400 MHz NMR

High performance digital NMR spectrometer, 2-channel microbay console and Linux host workstation running Topspin version 2.1 PL6

Equipped with:
Bruker-Biospin AVANCE III DPX400C magnet 9.40 Tesla (400 MHz proton resonance frequency)
B-VT 3200 variable temperature controller unit
5 mm Multinuclear Broad Band fluorine observe (BBFO) probe with digital tuning covering the range from $^{15}N$ and $^{31}P$ as well as $^{19}F$ with $^1H$ decoupling.

5. EXAMPLES

The following Examples were prepared analogously to the methods of synthesis described above. These compounds are suitable as SYK inhibitors and have $IC_{50}$-values with regard to SYK-inhibition of less than 10 nMol in the SYK inhibition assay and $EC_{50}$-values of less than 150 nMol in the CD63-assay. Additionally these compounds exhibit a very good SYK-selectivity which means that—whereas SYK is inhibited effectively—other kinases such as Aurora B (AURB), FLT3, GSK3β, etc. are not or almost not inhibited at all (further kinases which should not be effectively inhibited are RET, FLT4 RPS6KA3, STK22D and EPHA2). Consequently undesired side effects of these effective SYK-inhibitors of the invention are minimized.

AURB phosphorylates Ser10 and Ser28 on histone H3, a key event in mitosis and cellular proliferation. Inhibition of AURB therefore has the potential to block cellular proliferation, and could compromise tissues that exhibit a high cellular turnover, such as the intestine or the bone marrow. It is therefore desired to avoid parallel AURB inhibition of an effective SYK inhibitor to improve the overall clinical safety profile of the compound. Consequently all example compounds show $IC_{50}$-values with regard to Aurora B inhibition of more than 10000 nMol and the $IC_{50(AURB)}/IC_{50(SYK)}$-ratios of all example compounds are more than 10000, preferably even more than 15000.

FLT3 is a tyrosine kinase receptor. When an FLT3 ligand binds to the receptor, the intrinsic tyrosine kinase activity of the receptor is activated, which in turn phosphorylates and activates signal transduction molecules (such as SHC) which in turn propagates the signal in the cell. Signaling through FLT3 plays a role in cell survival, proliferation, and differentiation and is important for lymphocyte (B cell and T cell) development. It is therefore desired to avoid parallel FLT3 inhibition of an effective SYK inhibitor to improve the overall clinical safety profile of the compound. Consequently all example compounds of the instant invention show $IC_{50}$-values with regard to FLT3 inhibition of more than 1000 nMol.

Glycogen synthase kinase 3 beta (GSK3β) is a proline-directed serine-threonine kinase that is prominent in the TGF- and Wnt intracellular signalling pathways. GSK3β facilitates a number of intracellular signalling pathways including the activation of β-catenin complex. In adults, GSK3β is involved in cellular proliferation and energy metabolism, whilst in neonates is involved in neuronal cell development and body pattern formation. It is therefore desired to avoid parallel GSK3β inhibition of an effective SYK inhibitor to improve the overall clinical safety profile of the compound. Consequently all example compounds of the invention show $IC_{50}$-values with regard to GSK3β inhibition of more than 5000 nMol, preferably of more than 10000 nMol.

The $IC_{50}$-values with respect to SYK-inhibition, with respect to Aurora B and FLT3-inhibition for each of the individual example substances are shown in the following Table 1 and were experimentally determined as follows:

5.1 SYK Kinase Inhibition Test

Recombinant human SYK (amino acids 342-635) was expressed as a fusion protein with an N-terminal GST tag, affinity-purified and deep-frozen at a concentration of approx. 50-100 µM in storage buffer (25 mM HEPES pH7.5; 25 mM $MgCl_2$; 5 mM $MnCl_2$; 50 mM KCl; 0.2% BSA; 0.01% CHAPS; 100 µM $Na_3VO_4$; 0.5 mM DTT, 10% glycerol) at −80° C. until use.

The catalytic activity of the GST-SYK kinase fusion protein was determined using the Kinase Glo® Luminescence Kinase test (Promega; V6712). In this homogeneous test the amount of ATP remaining after the kinase reaction is quantified by a luciferin-luciferase reaction using luminescence. The luminescence signal obtained correlates with the amount of ATP still present and thus correlates inversely with the activity of the kinase.

Method

The test compounds were dissolved in 100% DMSO at a concentration of 10 mM and diluted in DMSO to a concentration of 1 mM. Serial Dilution is done in 100% DMSO. All further dilutions of the substances were carried out with test buffer (25 mM HEPES pH7.5; 25 mM $MgCl_2$; 5 mM $MnCl_2$; 50 mM KCl; 0.2% HSA; 0.01% CHAPS; 100 µM $Na_3VO_4$; 0.5 mM DTT). Dilution steps and concentration range were adapted according to need. 7 µl aliquots of these dilutions were transferred into a 384-well Optiplate (Perkin Elmer, #6007290). GST-SYK was diluted to 12 nM in the test buffer and 5 µl of this dilution were used in the kinase test (final concentration of SYK=4 nM in a total volume of 15 µl). After 15 minutes incubation at room temperature 3 µl of a mixture of 750 nM ATP and 100 µg/ml poly (L-Glutamic acid L-Tyrosine 4:1), Fluka #81357) in test buffer were added to each well and the incubation was continued for a further 60 minutes at room temperature.

Positive controls are the reaction mixtures that contain no test substance; negative controls (blanks) are reaction mixtures that contain no kinase.

After 60 minutes, 10 µl Kinase-Glo® solution (Promega, Cat. # V6712) (heated to room temperature) were added to each well and incubation was continued for a further 15 minutes. The plates were read in Envision Luminescence Reader (Perkin-Elmer).

Data Evaluation and Calculation:

The output file of the reader is a csv file that contains the well number and measured relative light units (RLU). For data evaluation and calculation, the measurement of the negative control was set as 100% ctrl and the measurement of the positive control was set as 0% ctrl. Based on this values the % value for the measurement of each substance concentration was calculated using an Assay Explorer software (Accelrys). Normally, the % ctrl values calculated are between 0% and 100% values but may also occur outside these limits in individual cases based on variability or compound characteristics. The $IC_{50}$-values were calculated from the % ctrl values using Assay Explorer software. Calculation: $[y=(a-d)/(1+(x/c)^b)+d]$ a=low value, d=high value; x=conc M; c=IC50 M; b=hill; y=% ctrl.

Satisfying SYK inhibitory capacities are represented by an $IC_{50(SYK)}$-Value measured by this assay of <10 nMol.

5.2 CD63-Assay (Cellular Assay for SYK-Inhibition)

SYK is essential for the FcεR1-mediated activation and degranulation of mast cells and basophils. In this assay, IgE raised against dinitrophenol (DNP) is incubated in whole blood where it binds to the FcεR1 on basophils. Subsequently the antigen DNP is added, which binds to the FcεR1-bound IgE, resulting in SYK dependent basophil degranulation. CD63 normally resides on the intracellular granule membrane within basophils, which upon degranulation, is then expressed on the surface where it can be detected by flow cytometry. Surface expression of CD63 correlates extremely well with the release of histamine from basophils. The CD63 assay has previously been validated as a clinical target engagement biomarker in the Fostamatinib SYK program (Braselmann et al, J. Pharm. Exp. Therap. 319:998-1008, 2006).

Method:

Heparinized whole blood is mixed gently (vortex mixer) and 1001 µL per test aliquoted into a 96 well plate. Anti-DNP (1 mg/ml) is diluted 1:100 with PBS/0.1% HSA to 10 µg/ml (final concentration: 1 µg/mL). Pre-dilute DNP/BSA (5 mg/ml) to a concentration of 60 ng/ml with washing solution.

Compounds: Solutions of 1 mM; 100 µM; 10 µM; 1 µM and 0.11 µM are prepared with 100% DMSO. 1:100 dilutions with PBS/0.1% HSA to generate concentrations of 10 µM; 1 µM; 0.1 µM; 0.01 µM; 0.001 µM (final concentration: 1000; 100; 10; 1; 0.1 nM).

Reagents are provided from the Basotest® kit.

Incubate 10 µl of 10 µg/ml anti DNP and 10 µl of compound with 100 µl whole blood in a 37° C. pre-warmed water bath. After 30 minutes, 20 µl of STIMULATION BUFFER is added to the whole blood samples and vortexed gently. Incubate the samples for 10 min at 37° C. in a water bath. 100 µl of DNP/BSA is added per test to the whole blood. Add 100 µl of the WASHING SOLUTION to a further test tube as a negative control. Add 100 µl of DNP/BSA (final 30 ng/ml) in the compound tubes. All tubes are mixed once more. The samples are incubated for 20 min at 37° C. in a water bath.

Stop degranulation by incubating the samples on ice for 5 min. Add 20 µl of STAINING REAGENT to each tube. Vortex and incubate the tubes for 20 min in an ice bath, covered to prevent exposure to light. The whole blood samples are lysed and fixed with 2 ml of pre-warmed (room temperature) 1×LYSING SOLUTION. Vortex and incubate for 10 min at room temperature. Spin down cells (5 min, 250×g, 4° C.). Discard the supernatant.

Add 3 ml of WASHING SOLUTION to the tubes. Centrifuge the tubes (5 min, 250×g, 4° C.). Aspirate the supernatant. Add 200 µl WASHING SOLUTION to the cell pellet, vortex.

Incubate the tubes in a covered ice bath until analysis.

Cells are analysed by flow cytometry using the blue-green excitation light (488 nm argon-ion laser). Acquire data by using fluorescence triggering in the FL2 channel (PE) to gate on basophilic granulocytes expressing high amounts of IgE. This live gating reduces the amount of data and saves memory capacity. Acquire at least 500 basophils per sample.

Data Evaluation and Calculation:

For data evaluation and calculation, the measurement of the negative control (unstimulated blood) was set as 100% control and the measurement of the positive control (DNP/anti-DNP stimulated blood) was set as 0% control. Based on these values the % value for the measurement of each substance concentration was calculated, a concentration-effect curve fitted and an $EC_{50}$ value calculated using GraphPad Prism version 6.01 for Windows. The $EC_{50}$ value was calculated using a nonlinear fitting (log(inhibitor) vs. response—variable slope). Normally, the % control values calculated are between 0% and 100% values but may also occur outside these limits in individual cases based on variability or compound characteristics.

Satisfying CD63 inhibitory capacities are represented by an $EC_{50}$-value measured by this assay of <150 nMol.

5.3 Aurora B Kinase Test

Recombinant human Aurora B (amino acids 1-344, clone number DU1773, Molecular weight 40.2 kDa, University of Dundee) was expressed as a fusion protein with an N-terminal His tag, affinity-purified and deep-frozen at a concentration of approx. 0.25-0.5 mg/ml in storage buffer (50 mM Tris-HCl pH 8; 25 mM Na—ß-glycerophosphat; 0.1 mM EGTA; 150 mM NaCl; 0.03% Brij-35; 1 mM DTT and 10% glycerol) at −80° C. until use.

The activity of the Aurora B kinase protein was determined using the ADP Glo® Luminescence Kinase test (Promega; V9103X). In this homogeneous test the amount of ADP remaining after the kinase reaction is quantified by a luciferin-luciferase reaction using luminescence. The luminescence signal obtained correlates with the amount of ADP still present and thus correlates with the activity of the protein kinase.

Method

The test compounds were dissolved in 100% DMSO at a concentration of 10 mM and diluted in DMSO to a concentration of 5 mM. Serial Dilution is done in 1:10 steps in 100% DMSO. All further dilutions of the substances were carried out with test buffer (50 mM Hepes, pH 7.5, 10 mM MgCl2, 1 mM EGTA, 60 µM Ultra Pure ATP, 0.01% Brij35, 0.1% BSA, 5 mM ß-Glycerophosphate) until a concentration was reached which was 2.5 times above the final test concentration (final concentration of the compounds: 50 µM to 0.005 nM). 4 µl aliquots of these dilutions were transferred into a 384-well Optiplate (Perkin Elmer, #6007290). His-Aurora B was diluted to 125 nM in the test buffer and 4 µl of this dilution were used in the kinase test (final concentration of Aurora B=50 nM in a total volume of 10 µl). After 15 minutes incubation at room temperature 2 µl of 250 µM substrate ([LRRLSLGLRRLSLGLRRLSLGLRRLSLG]; University of Dundee) in test buffer were added to each well and the incubation was continued for a further 60 minutes at room temperature.

Positive controls are the reaction mixtures that contain no test substance; negative controls (blanks) are reaction mixtures that contain no kinase.

After 60 minutes, 10 µl ADP-Glo® solution (ADP-Glo Reagent #V912B Promega) (heated to room temperature) were added to each well and incubation was continued for a further 40. minutes. Then 20 µl Kinase detection mix (Detection Buffer #V913B Promega; Kinase Detection Substrate #V914B Promega) were added and incubated for 40 minutes at room temperature. The plates were read in Envision Luminescence Reader (Perkin-Elmer).

Data Evaluation and Calculation:

The output file of the reader is a csv file that contains the well number and measured RLU. For data evaluation and calculation, the measurement of the negative control was set as 0% ctrl and the measurement of the positive control was set as 100% ctrl. Based on this values the % value for the measurement of each substance concentration can be calculated using an Assay Explorer software (e.g. Accelrys). Normally, the % ctrl values calculated are between 0% and 100% values but may also occur outside these limits in individual cases based on variability or compound characteristics. The $IC_{50}$-values were calculated from the % ctrl values using Assay Explorer software. Calculation: $[y=(a-d)/(1+(x/c)^b)+d]$, a=low value, d=high value; x=conc M; c=IC50 M; b=hill; y=% ctrl.

The compounds of the instant invention are SYK-inhibitors and should not affect other kinases such as AURB which is generally reflected by a large $IC_{50(AURB)}$-Value, preferably of >10000 nMol and more preferably of >15000 nMol, particularly preferably of >20000 nMol and by a ratio $IC_{50(AURB)}/IC_{50(SYK)}$>10000, more preferably >15000, particularly preferable >20000.

5.4 FLT3 Kinase Test

Recombinant human FLT3 (amino acids 564-958, Molecular weight 48.6 kDa, Invitrogen #PR4666C) was expressed with an Histidine tag, affinity-purified and deep-frozen at a concentration of approx. 0.35 mg/ml in storage buffer (50 mM Tris (pH 7.5), 100 mM NaCl, 0.05 mM EDTA, 0.05% NP-40, 2 mM DTT and 50% Glycerol) at −80° C. until use. The activity of the FLT3 kinase protein was determined using the ADP Glo® Luminescence Kinase test (Promega; V9103X). In this homogeneous test the amount of ADP remaining after the kinase reaction is quantified by a luciferin-luciferase reaction using luminescence. The luminescence signal obtained correlates with the amount of ADP still present and thus correlates with the activity of the protein kinase.

Method

The test compounds were dissolved in 100% DMSO at a concentration of 10 mM and diluted in DMSO to a concentration of 5 mM. Serial Dilution is done in 1:10 steps in 100% DMSO. All further dilutions of the substances were carried out with test buffer (50 mM Hepes, pH 7.5, 10 mM MgCl2, 1 mM EGTA, 0.01% Brij35, 0.1% BSA) until a concentration was reached which was 2.5 times above the final test concentration (final concentration of the compounds: 50 µM to 0.005 nM). 4 µl aliquots of these dilutions were transferred into a 384-well Optiplate (Perkin Elmer, #6007290). FLT3 enzyme was diluted to 5 nM in the test buffer and 4 µl of this dilution were used in the kinase test (final concentration of FLT3=2 nM in a total volume of 10 µl). After 60 minutes incubation at room temperature 2 µl mixture of 2.5 mg/ml substrate (Poly-Glu/Tyr; Sigma #P0275) and 2.5 mM ultra-pure ATP (Promega #V915B) in test buffer were added to each well and the incubation was continued for a further 90 minutes at room temperature.

Positive controls are the reaction mixtures that contain no test substance; negative controls (blanks) are reaction mixtures that contain no kinase.

After 90 minutes, 10 µl ADP-Glo® solution (ADP-Glo Reagent #V912B Promega) (heated to room temperature) were added to each well and incubation was continued for a further 60. minutes. Then 20 µl Kinase detection mix (Detection Buffer #V913B Promega; Kinase Detection Substrate #V914B Promega) were added and incubated for 40 minutes at room temperature. The plates were read in Envision Luminescence Reader (Perkin-Elmer).

Data Evaluation and Calculation:

The output file of the reader is a csv file that contains the well number and measured RLU. For data evaluation and calculation, the measurement of the negative control was set as 0% ctrl and the measurement of the positive control was set as 100% ctrl. Based on this values the % value for the measurement of each substance concentration can be calculated using an Assay Explorer software (e.g. Accelrys). Normally, the % ctrl values calculated are between 0% and 100% values but may also occur outside these limits in individual cases based on variability or compound characteristics. The $IC_{50}$ values were calculated from the % ctrl values using Assay Explorer software. Calculation: $[y=(a-d)/(1+(x/c)^b)+d]$, a=low value, d=high value; x=conc. M; c=IC50 M; b=hill; y=% ctrl.

The compounds of the instant invention are SYK-inhibitors and should not affect other kinases such as FLT3 which is generally reflected by a large $IC_{50(FLT3)}$-value, preferably of >1000 nMol.

5.5 GSK3p Kinase-Test

The inhibition of GSK3beta is measured in ADP-Glo Kinase Assay, Custom, #V9103X, Promega.

Human GSK31 (expressed and purified from SF21 cells) is obtained from the University Dundee/Scotland (Dr. James Hastie—Dept. of Biochemistry, 51.05 KDa, #899) in 50 mM Tris (pH7.5); 150 mM NaCl; 0.1 mM EGTA, 270 mM Succrose, 0.1%-mercaptoethanol, 1 mM benzamidine, 0.2 mM PMSF).

The enzyme is diluted to 0.63 mg/ml (12.34 µM), stored in aliquots at −80° C.

Method:

Assay buffer (50 mM Hepes, pH7.5, 10 mM MgCl2, 1 mM EGTA, 0.01% Brij35, 0.1% BSA) is prepared from stock solutions, which are stored at 4° C. All buffers and reagents are equilibrated to room temperature. Enzyme and ATP are diluted just before use.

Test compounds are dissolved in DMSO to a concentration of 10 mM and stored at −20° C.

Serial dilutions of 10 mM compound stocks are prepared in DMSO with a dilution factor of 6.

Compound stocks are used for serial dilution with predilution 1:2 that results in a final assay start concentration of 50 µM or other useful predilution factors. The final DMSO concentration is 1%.

The serial dilutions (8 concentrations) are transferred to assay buffer with a dilution of 1:40.

4 µl of these buffer dilutions of compounds are added to 384 well optiplates (384well plates, optiplate white, flat bottom, #6007290, Perkin Elmer).

Positive and negative controls contain DMSO also diluted 1:40 in assay buffer, 4 µl/well.

His-GSK3beta is diluted in assay buffer to a concentration 2.5-fold above final concentration (final=2 nM), 41 µl/well are added to compound predilutions and high values. Assay buffer without enzyme is added to negative controls.

No substrate is needed because of autophosphorylation on enzyme.

Optiplates are centrifuged (short spin), gently shaken, covered with a lid and incubated at room temperature for 60 min.

ATP (Ultra Pure ATP, 10 mM #V915B, Promega) is diluted in assay buffer to a concentration 5-fold above final concentration (final=7 M), 2 µl/well are added to mixture of compound and enzyme, also to high and low values.

Optiplates are centrifuged (short spin), gently shaken, covered with a lid and incubated at room temperature for 90 min.

10l ADP-Glo Reagent (ADP-Glo Reagent #V912B Promega) is added to all wells to deplate unused ATP. Plates are mixed by gentle shaking, incubation time 60 min, covered with a lid.

20 µl Kinase Detection Reagent (Kinase Detection Substrate #V914B Promega dissolved in Kinase Detection Buffer #V913B Promega) is added to all wells to transform ADP to ATP, which was produced during kinase reaction. Plates are mixed by gentle shaking, incubation time 40 min sealed with top seal, protected from light.

The plates were read in Envision Luminescence Reader (Perkin-Elmer).

Data Evaluation and Calculation:

The output file of the reader is a csv file that contains the well number and measured RLU.

For data evaluation and calculation, the measurement of the negative control was set as 0% ctrl and the measurement of the positive control was set as 100% ctrl. Based on this values the % value for the measurement of each substance concentration can be calculated using an Assay Explorer software (e.g. Accelrys). Normally, the % ctrl values calculated are between 0% and 100% values but may also occur outside these limits in individual cases based on variability or compound characteristics. The $IC_{50}$-values were calculated from the % ctrl values using Assay Explorer software. Calculation: [y=(a−d)/(1+(x/c)^b)+d], a=low value, d=high value; x=conc M; c=IC50 M; b=hill; y=% ctrl.

The compounds of the instant invention are SYK-inhibitors and should not affect other kinases such as GSK31 which is generally reflected by a large $IC_{50(GSK3\beta)}$-value, preferably of >5000 nMol and more preferably of >10000 nMol.

5.6 Human Liver Microsomal Stability Test

Further it is desirable for an SYK-inhibitor that is sufficiently SYK-specific as described above to have certain metabolic stability as measured for instance in the presence of human liver microsomes corresponding to $Q_h$<23%, wherein $Q_h$ is the percentage of liver blood flow (the stability is better, the lower the $Q_h$-value is). If the $Q_h$-value for the SYK-inhibitor in question is too high (larger than 23%), it will be difficult to reach an adequate plasma level of the corresponding SYK— inhibitor in the patient to be treated.

Method:

The metabolic degradation for a specific SYK-inhibitor is performed at 37° C. with pooled human liver microsomes (human liver microsomes are commercially available as "BD UltraPool™" by Corning Life Sciences, Fogostraat 12, 1060 LJ Amsterdam, The Netherlands). The final incubation volume of 100 µl per time point contains TRIS buffer pH 7.6 at RT (0.1 M), magnesium chloride (5 mM), microsomal protein (1 mg/ml) and the test compound at a final concentration of 1 µM.

Following a short preincubation period at 37° C., the reaction is initiated by addition of beta-nicotinamide adenine dinucleotide phosphate in its reduced form (NADPH, 1 mM) and terminated by transferring an aliquot into solvent after different time points. Additionally, the NADPH-independent degradation is monitored in incubations without NADPH, terminated at the last time point.

The quenched (terminated) incubations are then pelleted by centrifugation (10000 g, 5 min).

An aliquot of the supernatant is assayed by LC-MS/MS for the remaining amount of parent compound. The half-life (t½ INVITRO) is determined by the slope of the semilogarithmic plot of the concentration-time profile.

Data Evaluation and Calculation:

The intrinsic clearance (CL_INTRINSIC) is calculated by considering the amount of protein in the incubation:

CL_INTRINSIC [µl/min/mg protein]=(Ln 2/(t½INVITRO [min]*protein content [mg/ml]))*1000

The protein content [mg/ml] was determined with the "Bicinchoninic Acid Kit" of Sigma Aldrich (commercially available).

The upscaled intrinsic Clearance (CL_UP_INT) is calculated by considering the liver weight [g liver/kg body weight] and the microsomal recovery [mg protein/g liver]:

CL_UP_INT[ml/min/kg]= 0.001*CL_INTRINSIC*liver weight*microsomal recovery with microsomal recovery=45 mg protein/g liver
with liver weight=25.7 g liver/kg body weight The percent hepatic blood flow (% $Q_h$) is finally calculated by considering the human liver blood flow Q [ml/min/kg]:

% $Q_h[\%]=((Q*CL\_UP\_INT)/(Q+CL\_UP\_INT)/Q)*100$ with liver blood flow (Q)=20.7 ml/min/kg.

5.7 Human Hepatocyte Stability Test

A more comprehensive way to measure the metabolic stability of a compound of the instant invention than microsomal stability (section 5.6) is the human hepatocyte stability test as described below. Herein the metabolic degradation for the compound in question is performed in a human hepatocyte suspension.

Human hepatocytes (typically cryopreserved) are incubated in an appropriate buffer system (e.g. Dulbecco's modified eagle medium plus 3.5 µg glucagon/500 mL, 2.5 mg insulin/500 mL and 3.75 mg/500 mL hydrocortison) containing 5% species serum.

Following a (typically) 30 min preincubation in an incubator (37° C., 10% $CO_2$) 5 µl of the solution of the compound to be tested (80 M; from 2 mM in DMSO stock solution diluted 1:25 with medium) are added into 395 µl hepatocyte suspension (cell density is in the range of 0.25-5 Mio cells/mL, typically 1 Mio cells/mL; the final concentration of the compound in question is 11 M, the final DMSO concentration is 0.05%).

The cells are incubated for six hours (incubator, orbital shaker) and samples (25 µl) are taken at 0, 0.5, 1, 2, 4 and 6 hours. Samples are transferred into acetonitrile and pelleted by centrifugation (5 min). The supernatant is transferred to a new 96-deepwell plate, evaporated under nitrogen and resuspended.

The decline of the compound to be tested is analyzed by HPLC-MS/MS.

Data Evaluation and Calculation:

CLint is calculated as follows CL_INTRINSIC=Dose/AUC=(C0/CD)/(AUD+clast/k)×1000/60.

C0: initial concentration in the incubation [µM],
CD: cell density of vital cells [$10^6$ cells/mL],
AUD: area under the data [µM×h],
clast: concentration of last data point [µM],
k: slope of the regression line for the compound in question decline [h−1].

The calculated in vitro hepatic intrinsic clearance can be scaled up to the intrinsic in vivo hepatic Clearance and used to predict hepatic in vivo blood clearance (CL) by the use of a liver model (well stirred model).

CL_INTRINSIC_INVIVO [ml/min/kg]=(CL_INTRINSIC [µL/min/$10^6$cells]×hepatocellularity [$10^6$ cells/g liver]×liver factor [g/kg bodyweight])/1000

CL [ml/min/kg]=CL_INTRINSIC_INVIVO [ml/min/kg]×hepatic blood flow [ml/min/kg]/(CL_INTRINSIC_INVIVO [ml/min/kg]+hepatic blood flow [ml/min/kg])

$Q_h[\%]$=CL [ml/min/kg]/hepatic blood flow [ml/min/kg])

Hepatocellularity, human: 120×$10^6$ cells/g liver
Liver factor, human: 25.7 g/kg bodyweight
Blood flow, human: 21 ml/(min×kg)

A satisfying human hepatocyte stability for a compound in question measured by this assay is represented by a $Q_h$<20% (whereby the stability is better, the lower the $Q_h$-value is).

TABLE 1

Example compounds and their properties with respect to SYK-inhibiton, SYK-selectivity and metabolic stability (as experimentally determined)

| Ex. No. | Structure | | CD63 assay $EC_{50}$-value (chapter 5.2) [nM] | SYK inhibition $IC_{50}$-value, (chapter 5.1) [nM] | AURB inhibition $IC_{50}$-value (chapter 5.3) [nM] | FLT3 inhibition $IC_{50}$-value (chapter 5.4) [nM] | stability in human hepatocytes (chapter 5.7) HEPhu [% $Q_h$] | selectivity ratio $IC_{50(AURB)}/IC_{50(SYK)}$ |
|---|---|---|---|---|---|---|---|---|
| 1 | (structure) | Chiral | 41 | 1 | 34800 | 2230 | 10 | 34800 |

TABLE 1-continued

Example compounds and their properties with respect to SYK-inhibiton, SYK-selectivity and metabolic stability (as experimentally determined)

| Ex. No. | Structure | | SYK inhibition IC$_{50}$-value, (chapter 5.1) [nM] | CD63 assay EC$_{50}$-value (chapter 5.2) [nM] | AURB inhibition IC$_{50}$-value (chapter 5.3) [nM] | FLT3 inhibition IC$_{50}$-value (chapter 5.4) [nM] | stability in human hepatocytes (chapter 5.7) HEPhu [% Q$_h$] | selectivity ratio IC$_{50(AURB)}$/IC$_{50(SYK)}$ |
|---|---|---|---|---|---|---|---|---|
| 2 | 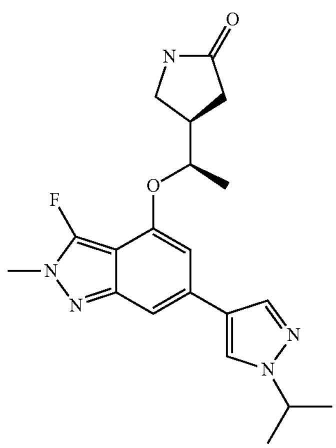 | Chiral | 1.3 | 45 | 31141 | 2834 | <4 | 23955 |
| 3 | 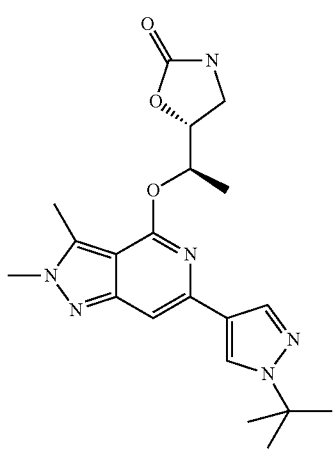 | Chiral | 2 | 51 | 31461 | 1340 | 7 | 15731 |
| 4 | 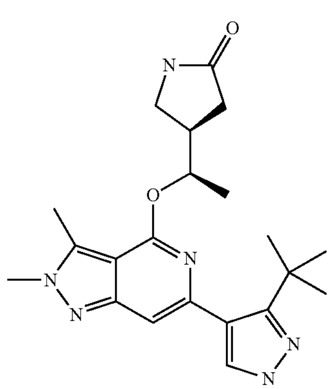 | Chiral | 2.2 | 64 | 65200 | 7410 | 10 | 29636 |

TABLE 1-continued

Example compounds and their properties with respect to SYK-inhibiton, SYK-selectivity and metabolic stability (as experimentally determined)

| Ex. No. | Structure | | SYK inhibition IC$_{50}$-value, (chapter 5.1) [nM] | CD63 assay EC$_{50}$-value (chapter 5.2) [nM] | AURB inhibition IC$_{50}$-value (chapter 5.3) [nM] | FLT3 inhibition IC$_{50}$-value (chapter 5.4) [nM] | stability in human hepatocytes (chapter 5.7) HEPhu [% Q$_h$] | selectivity ratio IC$_{50(AURB)}$/ IC$_{50(SYK)}$ |
|---|---|---|---|---|---|---|---|---|
| 5 | 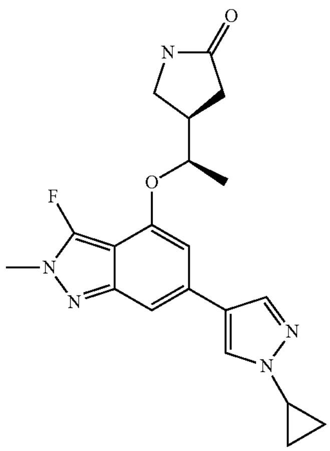 | Chiral | 3.3 | 52 | 50000 | 3990 | <4 | 15152 |
| 6 | 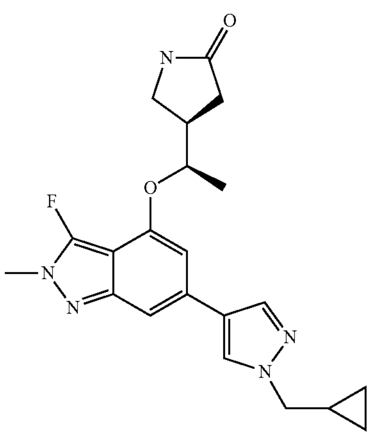 | Chiral | 2.6 | 42 | 34100 | 3730 | 6 | 13115 |
| 7 | 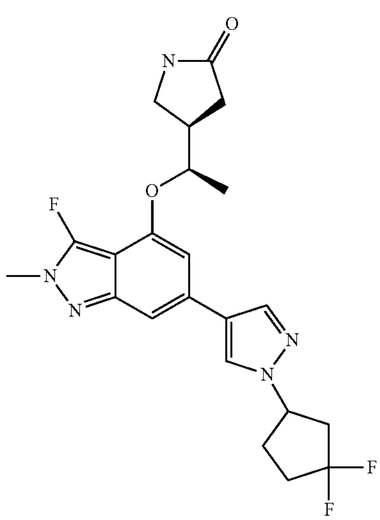 | Chiral | 1.3 | 53 | 26200 | 2440 | <4 | 20154 |

TABLE 1-continued

Example compounds and their properties with respect to SYK-inhibiton, SYK-selectivity and metabolic stability (as experimentally determined)

| Ex. No. | Structure | | SYK inhibition IC$_{50}$-value, (chapter 5.1) [nM] | CD63 assay EC$_{50}$-value (chapter 5.2) [nM] | AURB inhibition IC$_{50}$-value (chapter 5.3) [nM] | FLT3 inhibition IC$_{50}$-value (chapter 5.4) [nM] | stability in human hepatocytes (chapter 5.7) HEPhu [% Q$_h$] | selectivity ratio IC$_{50(AURB)}$/ IC$_{50(SYK)}$ |
|---|---|---|---|---|---|---|---|---|
| 8 | 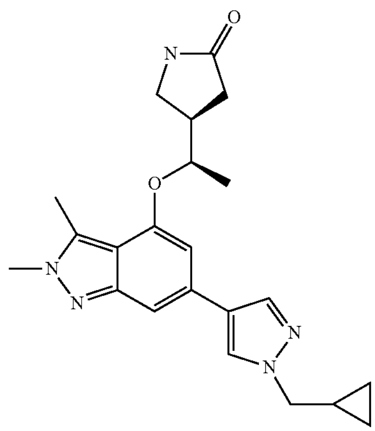 | Chiral | 1.4 | 47 | 21112 | 2071 | 5 | 15080 |
| 9 | 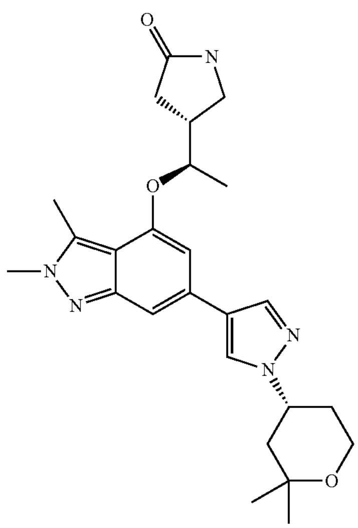 | Chiral | 1.1 | 52 | 23341 | 1840 | 6 | 21219 |
| 10 | 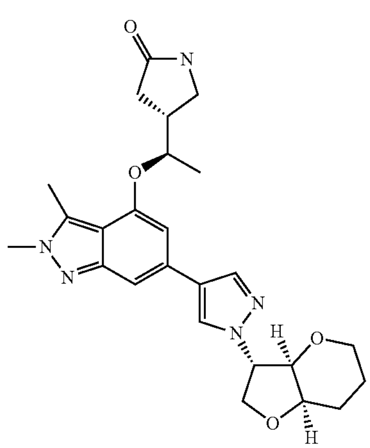 | Chiral | 3.3 | 65 | 34030 | 2015 | 9 | 10312 |

TABLE 1-continued

Example compounds and their properties with respect to SYK-inhibiton, SYK-selectivity and metabolic stability (as experimentally determined)

| Ex. No. | Structure | | SYK inhibition IC$_{50}$-value, (chapter 5.1) [nM] | CD63 assay EC$_{50}$-value (chapter 5.2) [nM] | AURB inhibition IC$_{50}$-value (chapter 5.3) [nM] | FLT3 inhibition IC$_{50}$-value (chapter 5.4) [nM] | stability in human hepatocytes (chapter 5.7) HEPhu [% Q$_h$] | selectivity ratio IC$_{50(AURB)}$/ IC$_{50(SYK)}$ |
|---|---|---|---|---|---|---|---|---|
| 11 | 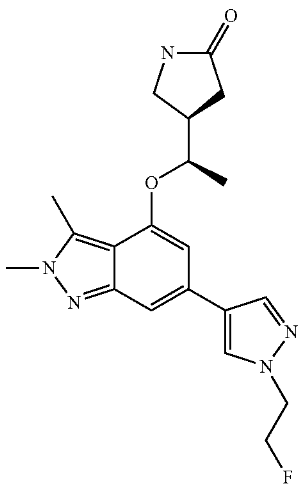 | Chiral | 1.5 | 65 | 31200 | 3480 | 4 | 20800 |
| 12 | 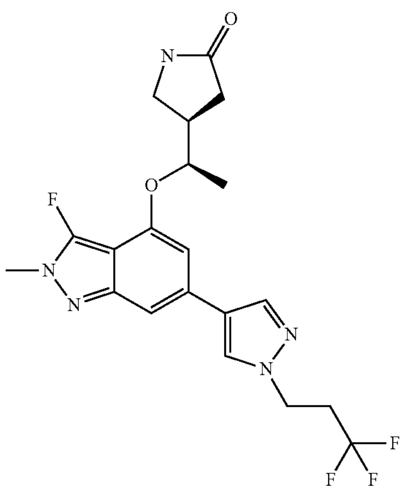 | Chiral | 2.9 | 67 | 29600 | 5030 | <4 | 10207 |
| 13 | 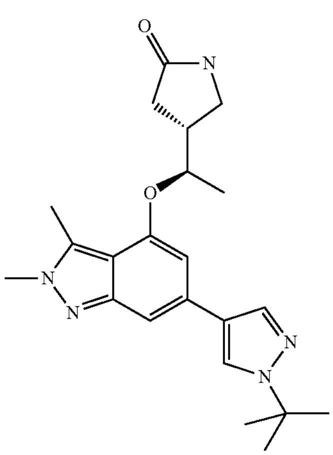 | Chiral | 0.9 | 58 | 35984 | 5219 | 3 | 39982 |

TABLE 1-continued

Example compounds and their properties with respect to SYK-inhibiton, SYK-selectivity and metabolic stability (as experimentally determined)

| Ex. No. | Structure | | SYK inhibition IC$_{50}$-value, (chapter 5.1) [nM] | CD63 assay EC$_{50}$-value (chapter 5.2) [nM] | AURB inhibition IC$_{50}$-value (chapter 5.3) [nM] | FLT3 inhibition IC$_{50}$-value (chapter 5.4) [nM] | stability in human hepatocytes (chapter 5.7) HEPhu [% Q$_h$] | selectivity ratio IC$_{50(AURB)}$/IC$_{50(SYK)}$ |
|---|---|---|---|---|---|---|---|---|
| 14 | 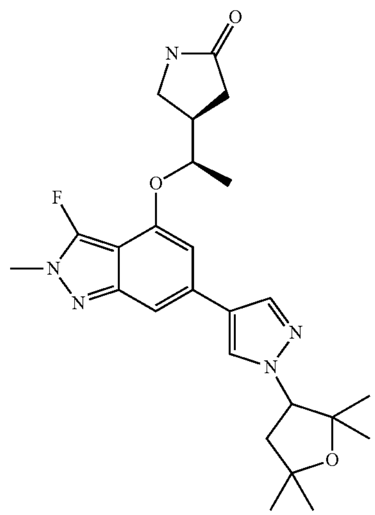 | Chiral | 3.2 | 76 | 50000 | 4050 | 12 | 15625 |
| 15 | 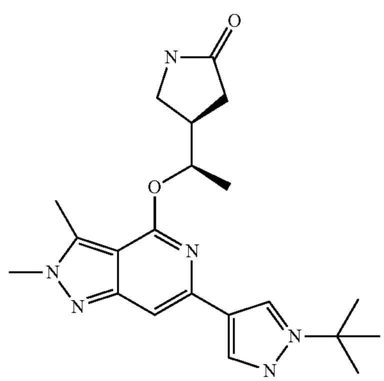 | Chiral | 2.2 | 77 | 50566 | 4788 | 10 | 22985 |
| 16 | 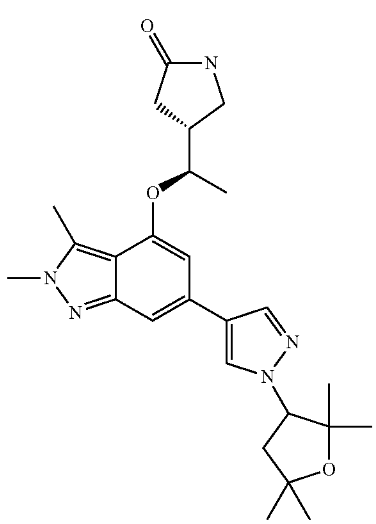 | Chiral | 3.1 | 82 | 44400 | 3490 | 6 | 14323 |

TABLE 1-continued

Example compounds and their properties with respect to SYK-inhibiton, SYK-selectivity and metabolic stability (as experimentally determined)

| Ex. No. | Structure | | SYK inhibition IC$_{50}$-value, (chapter 5.1) [nM] | CD63 assay EC$_{50}$-value (chapter 5.2) [nM] | AURB inhibition IC$_{50}$-value (chapter 5.3) [nM] | FLT3 inhibition IC$_{50}$-value (chapter 5.4) [nM] | stability in human hepatocytes (chapter 5.7) HEPhu [% Q$_h$] | selectivity ratio IC$_{50(AURB)}$/IC$_{50(SYK)}$ |
|---|---|---|---|---|---|---|---|---|
| 17 | 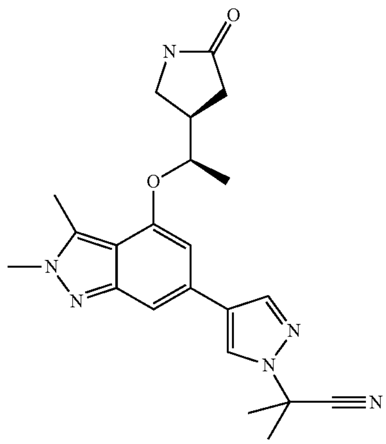 | Chiral | 2.9 | 92 | 50000 | 11295 | 4 | 17241 |
| 18 | 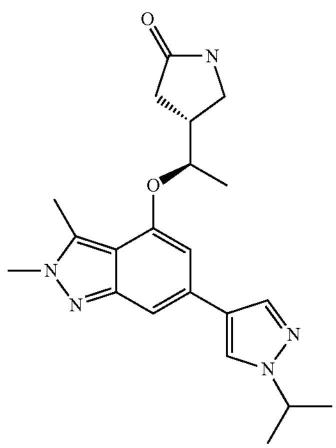 | Chiral | 1.1 | 95 | 20155 | 4673 | <4 | 18323 |
| 19 | 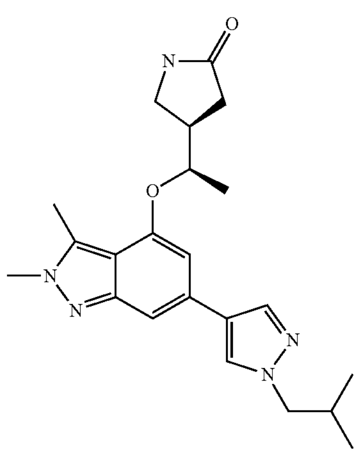 | Chiral | 1.8 | 107 | 23782 | 4954 | 7 | 13212 |

TABLE 1-continued

Example compounds and their properties with respect to SYK-inhibiton, SYK-selectivity and metabolic stability (as experimentally determined)

| Ex. No. | Structure | | SYK inhibition IC$_{50}$-value, (chapter 5.1) [nM] | CD63 assay EC$_{50}$-value (chapter 5.2) [nM] | AURB inhibition IC$_{50}$-value (chapter 5.3) [nM] | FLT3 inhibition IC$_{50}$-value (chapter 5.4) [nM] | stability in human hepatocytes (chapter 5.7) HEPhu [% Q$_h$] | selectivity ratio IC$_{50(AURB)}$/IC$_{50(SYK)}$ |
|---|---|---|---|---|---|---|---|---|
| 20 | 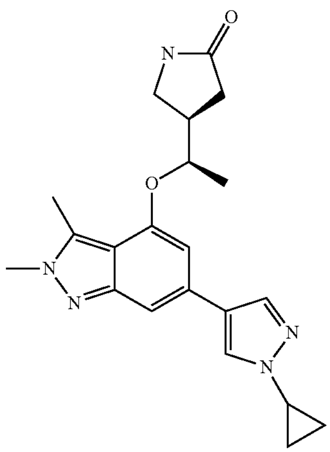 | Chiral | 2.5 | 134 | 34831 | 3316 | <4 | 13932 |
| 21 | 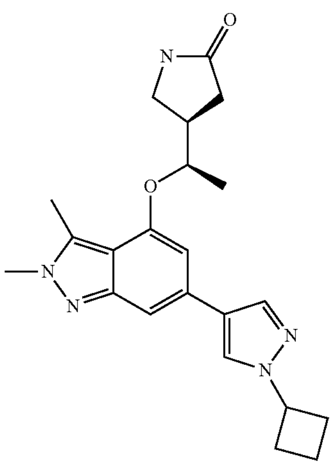 | Chiral | 1.2 | 76 | 17330 | 2210 | 7 | 14442 |
| 22 | 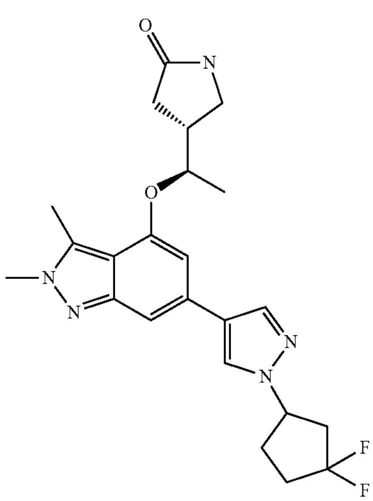 | Chiral | 1.2 | 67 | 13448 | 1948 | 3 | 11207 |

TABLE 2

Structurally closest prior art compounds (as disclosed in WO 15017610) and their properties regarding SYK-inhibition, SYK-selectivity and metabolic stability (as experimentally determined)

| Prior Art Compound | Structure | | SYK inhibition IC$_{50}$-value (chapter 5.1) [nM] | CD63 assay EC$_{50}$-value (chapter 5.2) [nM] | AURB inhibition IC$_{50}$-value (chapter 5.3) [nM] | FLT3 inhibition IC$_{50}$-value (chapter 5.4) [nM] | stability in human hepatocytes (chapter 5.7) HEPhu [% Q$_h$] | selectivity ratio IC$_{50(AURB)}$/ IC$_{50(SYK)}$ |
|---|---|---|---|---|---|---|---|---|
| example 5.20 on page 506 of WO15017610 | 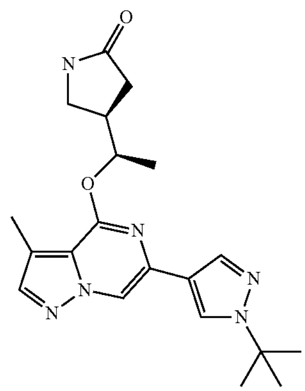 | Chiral | 0.2 | 77 | 162 | 43 | 31 | 810 |
| example 3A.02, on page 196 of WO15017610 | 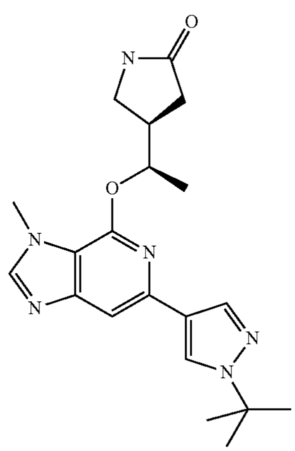 | Chiral | 1.9 | 42 | 1692 | 384 | 7 | 891 |
| example 6.09 on page 559 of WO15017610 | 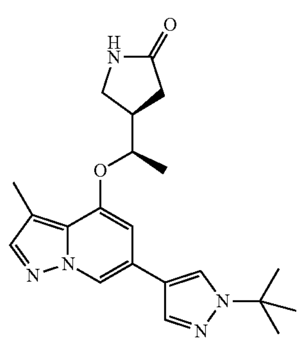 | Chiral | 0.1 | 20 | 37 | 25 | 17 | 370 |

TABLE 2-continued

Structurally closest prior art compounds (as disclosed in WO 15017610) and their properties regarding SYK-inhibition, SYK-selectivity and metabolic stability (as experimentally determined)

| Prior Art Compound | Structure | SYK inhibition $IC_{50}$-value (chapter 5.1) [nM] | CD63 assay $EC_{50}$-value (chapter 5.2) [nM] | AURB inhibition $IC_{50}$-value (chapter 5.3) [nM] | FLT3 inhibition $IC_{50}$-value (chapter 5.4) [nM] | stability in human hepatocytes (chapter 5.7) HEPhu [% $Q_h$] | selectivity ratio $IC_{50(AURB)}/IC_{50(SYK)}$ |
|---|---|---|---|---|---|---|---|
| example 3B.22 on page 219 of WO15017610 | 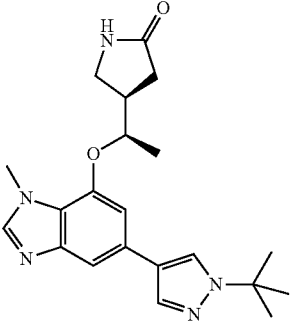 Chiral | 0.8 | 29 | 771 | 307 | 5 | 964 |
| example 6.60 on page 587 of WO15017610 | 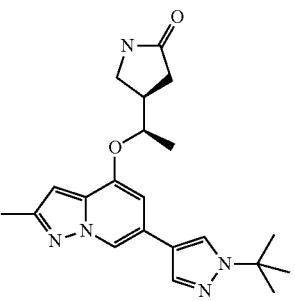 Chiral | 10.3 | 483 | >50000 | 6677 | <4 | >4850 |

The example compounds of the instant invention No. 1 to 22 (see Table 1) have been synthesized according to Chapter 4 and then the example compounds were subjected to the different assays as described in Chapter 5 in order to determine the capacity of SYK inhibition (low $IC_{50}$-value stands for a good SYK-inhibition, in particular $IC_{50}$-values of <10 nMol in the "SYK inhibition assay" and ECso-values of <150 nMol in the "CD63 assay" stand for satisfying SYK inhibitory properties)

the SYK-selectivity that means a very low inhibition of other kinases such as for instance a) Aurora B (good SYK-selectivity is reflected by "high" $IC_{50}$-values with respect to inhibition of AURB;

$IC_{50(AURB)}$>10000 or a ratio of $IC_{50(AURB)}/IC_{50(SYK)}$>10000 nMol is desired and stands for a good SYK-selectivity), b) FLT3 (good SYK-selectivity is reflected by "high" $IC_{50}$-values with respect to inhibition of FLT3, $IC_{50}$ $_{(FLT3)}$>1000 nMol is desired and stands for a good SYK-selectivity), the metabolic stability which can for instance be measured by the $Q_h$-percentage in human hepatocytes (% $Q_h$<20 stands for a sufficient metabolic stability for an SYK-inhibitor to be developed as a medicament).

The structurally closest prior art compounds as disclosed in WO15017610 have also been synthesized and were subjected to the same assays as described in Chapter 5 in order to determine the properties of these structurally closest prior art compounds with respect to the capacity of SYK-inhibition, CD63 potency, the SYK-selectivity and the metabolic stability and to compare them to the example compounds of the present invention.

Whereas example 5.20 on page 506 of WO15017610, example 3A.02 on page 196 of WO15017610, example 6.09 on page 559 of WO15017610 and example 3B.22 on page 219 of WO15017610 all have acceptable $IC_{50(SYK)}$-Values with an $IC_{50(SYK)}$<10 nMol in the "SYK-inhibition assay" and with an $EC_{50}$<150 nMol in the "CD63-assay", these prior art compounds all do not show a satisfying SYK-selectivity with regard to AURB. The $IC_{50(AURB)}$ of these prior art compounds are with 162 nMol, 1692 nMol, 37 nMol and 771 nMol significantly smaller than the $IC_{50(AURB)}$ of the example compounds of the invention which all have an $IC_{50(AURB)}$>10000 nMol (most of them have even an $IC_{50(AURB)}$>15000 nMol). The same is true for the ratios $IC_{50(AURB)}/IC_{50(SYK)}$ which are for the prior art examples 5.20, 3A.02, 6.09 and 3B.22 with 810, 891, 370 and 964 all significantly lower than 10000. The example compounds of the instant invention however, have $IC_{50(AURB)}/IC_{50(SYK)}$ ratios of >10000, very often even >15000.

Furthermore, example 5.20 on page 506 of WO15017610, example 3A.02 on page 196 of WO15017610, example 6.09 on page 559 of WO15017610 and example 3B.22 on page 219 of WO15017610 all do not show a satisfying SYK-selectivity with regard to FLT3.

The $IC_{50(FLT3)}$ of the prior art compounds example 5.20 on page 506 of WO15017610, example 3A.02 on page 196 of WO15017610, example 6.09 on page 559 of WO15017610 and example 3B.22 on page 219 of WO15017610 are with 43 nMol, 384 nMol, 25 nMol and 307 nMol significantly smaller than the $IC_{50}(F_{LT3})$ of the example compounds of the invention which all have an $IC_{50(FLT3)}$>1000 nMol (most of them have even an $IC_{50(FLT3)}$>2000 nMol).

In contrast to that the prior art compound 6.60 on page 587 of WO15017610 seems to have with $IC_{50(AURB)}$>50000 nMol and with $IC_{50(FLT-3)}$=6677 nMol at least with respect to the absolute measurements a sufficient SYK-selectivity, however for this prior art compound 6.60 (on page 587 of WO15017610) the SYK inhibitory capacity is not sufficient with an $IC_{50(SYK)}$ of 10.3 nMol ($IC_{50(SYK)}$ of larger than 10 nMol) and with an $EC_{50(SYK)}$ in the CD63-assay of 483 nMol ($EC_{50}$ in the CD63-assay is larger than 150 nMol).

Consequently only the compounds of the instant invention have at the same time a) an excellent SYK-inhibitory capacity ($IC_{50(SYK)}$<10 nMol, $EC_{50}$<150 nMol)

b) a good SYK-selectivity ($IC_{50(AURB)}$>10000 nMol, and $IC_{50(AURB)}/IC_{50(SYK)}$>10000 and $IC_{50(FLT3)}$>1000 nMol)) and c) a sufficient metabolic stability (% $Q_h$<20 in human hepatocytes)

which are all properties that are very significant for the use of an SYK-inhibitor as a medicament in order to treat SYK-related diseases.

6. INDICATIONS

As has been found, the compounds of formula 1 or 1' are characterised by their range of applications in the therapeutic field. Particular mention should be made of those applications for which the compounds of formula 1 or 1' according to the invention are preferably used on the basis of their pharmaceutical activity as SYK-inhibitors. Examples include respiratory complaints, allergic diseases, osteoporosis, gastrointestinal diseases or complaints, immune or autoimmune diseases, allergic diseases, inflammatory diseases, e.g. inflammatory diseases of the joints, skin and eyes and diseases of the peripheral or central nervous system.

Particular mention should be made of the prevention and treatment of respiratory tract and pulmonary diseases which are accompanied by increased mucus production, inflammation and/or obstructive diseases of the airways. Examples of these include asthma, pediatric asthma, ARDS (Adult Respiratory Distress Syndrome), acute, allergic or chronic bronchitis, autoimmune haemolytic anemia, chronic obstructive bronchitis (COPD) (including the treatment of Rhinovirus-induced exacerbations), coughs, allergic rhinitis or sinusitis, allergic rhinoconjunctivitis, chronic rhinitis or sinusitis, alveolitis, farmers' lung, hyperreactive airways, infectious bronchitis or pneumonitis, bronchiectasis, pulmonary arterial hypertension, pulmonary fibrosis, bronchial oedema, pulmonary oedema, pneumonia or interstitial pneumonia triggered by various causes such as aspiration, inhalation of toxic gases or bronchitis, pneumonia or interstitial pneumonia triggered by cardiac insufficiency, radiation, chemotherapy, cystic fibrosis or mucoviscidosis, alpha 1-antitrypsin deficiency.

The compounds according to the invention are preferably also suitable for the treatment of allergic diseases such as for example allergic rhinitis, allergic rhinoconjunctivitis, allergic conjunctivitis, and contact dermatitis, urticaria/angiooedema and allergic dermatitis.

Mention should also preferably be made of the treatment of inflammatory diseases of the gastrointestinal tract. Examples of these are Crohn's disease and ulcerative colitis.

The compounds according to the invention are preferably also suitable for the treatment of inflammatory diseases of the joints, of the blood vessels and of the kidney or inflammatory diseases of the skin and eyes. Examples of these are rheumatoid arthritis, antibody-based glomerulonephritis, psoriasis, Kawasaki syndrome, coeliac disease (sprue), arteriosclerosis and Wegener's granulomatosis, osteoarthritis, systemic scleroderma, ankylosing spondylitis.

The compounds according to the invention are preferably also suitable for the treatment of autoimmune diseases. Examples of these are hepatitis (autoimmune-based), lupus erythematodes, lupus nephritis, systemic lupus, Systemic lupus erythematosus, discoid lupus, cutaneous lupus erythematosus (acute, subacute, chronic), anti-phospholipid syndrome, Berger's disease, Evans's syndrome, immunohaemolytic anaemia, ITP (idiopathic thrombocytopenic purpura; adult, neonatal and paediatric), myasthenia gravis, Sjögren's syndrome, sclerodermy, Bullous pemphigoid and Pemphigus vulgaris.

The compounds according to the invention are preferably also suitable for the treatment of B-cell lymphomas, like chronic lymphocytic leukaemia and non-Hodgkin's lymphomas, Waldenstroem macroglubulinemia (Clinical Cancer Research (2015), 21(11), 2538-2545) or T cell lymphomas.

The compounds according to the invention are preferably also suitable for the treatment of Graft-versus-host disease.

Mention may preferably also be made of the prevention and treatment of diseases of the peripheral or central nervous system. Examples of these are acute and chronic multiple sclerosis or non-familial lateral sclerosis.

Mention should also preferably be made of the treatment of systemic sclerosis (SSc). Pamuk Omer Nuri; Can Guray; Ayvaz Suleyman; Karaca Turan; Demirtas Selim; Pamuk Gulsum E; Tsokos George, Clinical and experimental rheumatology (2015); ISSN: 0392-856X.

Mention should also preferably be made of the treatment of infectious diseases. Example of these are malaria (Abstracts, Joint 41st Great Lakes and 46th Central Regional Meeting of the American Chemical Society, GrandRapids, Mich., United States, May 27-30 (2015), JGLCRM-283; WO 2014100113) and dengue (Journal of Biological Chemistry, Volume: 290, Issue: 28, Pages: 17306-17320)

Mention may preferably also be made of the prevention and treatment of osteoporotic diseases such as for example disease-associated osteopenia, osteoporosis and osteolytic diseases.

The present invention relates particularly preferably to the use of compounds of formula 1 for preparing a pharmaceutical composition for the treatment of diseases selected from among asthma, COPD, allergic rhinitis, Adult Respiratory Distress Syndrome, bronchitis, allergic dermatitis, contact dermatitis, ITP, rheumatoid arthritis, systemic lupus erythematosus, lupus nephritis, and allergic rhinoconjunctivitis.

Most preferably, the compounds of formula 1 may be used for the treatment of a disease selected from among asthma, allergic rhinitis, rheumatoid arthritis, systemic lupus erythematosus, lupus nephritis, allergic dermatitis and COPD.

7. COMBINATIONS

The compounds of formula 1 or 1' may be used on their own or in conjunction with other active substances of formula 1 or 1' according to the invention. The compounds of formula 1 or 1' may optionally also be used in conjunction with other pharmacologically active substances. Preferably the active substances used here may be selected for example from among the betamimetics, anticholinergics, corticosteroids, PDE4-inhibitors, LTD4-antagonists, EGFR-inhibitors, MRP4-inhibitors, dopamine agonists, H1-antihistamines, PAF-antagonists, iNos-inhibitos, HMG-CoA reductase inhibitors (statins), PI3-kinase-inhibitors, CCR3-antagonists, CCR2-antagonists, CCR1-antagonists, IKK2-inhibitors, A2a agonists, alpha-4-integrin-inhibitors, CRTH2-antagonists, histamine 1, combined H1/H3-antagonists, p38 kinase inhibitors, methylxanthines, ENaC-inhibitors, CXCR1-antagonists, CXCR2-antagonists, ICE-inhibitors, LTB4-antagonists, 5-LO antagonists, FLAP-antagonists. LTB4-antagonists; cromoglycine, dissociated glucocorticoid mimetics, immunesuppressive agents, cytostatica, non-steroidal anti-inflammatory drugs (NSAIDs), chloroquine, hydroxychloroquine, anti-TNF-antibodies, anti-GM-CSF antibodies, anti-CD46-antibodies, anti-IL-1-antibodies, anti-IL-2-antibodies, anti-IL-4-antibodies, anti-IL-5-antibodies, anti-IL6 antibodies, anti-IL6 receptor antibodies, anti-IL-13-antibodies, anti-IL_18 antibodies, anti-CD30 L antibodies, anti-Ox40L-antibodies, anti-IL-4/IL-13-antibodies, anti-IL-23 (p19) antibodies, anti-IL-12/IL-23 (p40) antibodies, anti-CD3 antibodies, anti-CD4 antibodies, anti-CD154 antibodies, CD89 antibodies, anti-IL-2 receptor/CD25 antibodies, anti-CD22 antibodies, anti-interferon antibodies, anti-ICOS antibodies, anti-ICOS antibodies, anti-CD20 antibodies, anti-CD40 antibodies, anti-BAFF/BLyS antibodies, anti-CD18 antibodies, anti-CD62L antibodies, anti-CD147 antibodies, anti-integrin antibodies, agents interfering with LFA-1, IL-36 pathway modulators, M-CSF/c-fms antagonists, CTLA-4 fusions, mTor modulators, Toll like receptors 7 inhibitors (TLR7 inhibitor), Toll like receptor 9 inhibitors (TLR9 inhibitors), T cell-costimulatory modulators such as CTLA-4 fusions, JAK inhibitors, IRF modulators, CX3 chemokine receptor antagonists (CX3CR1 antagonists), IRAK inhibitors (in particular IRAK1- and IRAK4-inhibitors), Sphingosine-1-phosphate modulators (S1P pathway modulators), triple kinase inhibitors against PDGFR, FGFR and VEGFR e.g. Nintedanib or double or triple combinations thereof, such as for example combinations of one, two or three compounds selected from among the SYK-inhibitors of formula 1 or 1', betamimetics, corticosteroids, EGFR-inhibitors and PDE4-antagonists, SYK-inhibitors of formula 1 or 1', anticholinergics, betamimetics, corticosteroids, EGFR-inhibitors and PDE4-antagonists, SYK-inhibitors of formula 1 or 1', PDE4-inhibitors, corticosteroids and EGFR-inhibitors, SYK-inhibitors of formula 1 or 1', EGFR-inhibitors and PDE4-inhibitors, SYK-inhibitors of formula 1 or 1' and EGFR-inhibitors, SYK-inhibitors of formula 1, betamimetics and anticholinergics SYK-inhibitors of formula 1 or 1', anticholinergics, betamimetics, corticosteroids and PDE4-inhibitors, SYK-inhibitors of formula 1 or 1', anticholinergics, betamimetics, corticosteroids, iNOS inhibitors, HMG-CoA reductase inhibitors.

Combinations of three active substances each taken from one of the above-mentioned categories of compounds are also an object of the invention.

Suitable betamimetics used are preferably compounds selected from among arformoterol, carmoterol, formoterol, indacaterol, salmeterol, albuterole, bambuterol, bitolterol, broxaterol, carbuterol, clenbuterol, fenoterol, hexoprenalin, ibuterol, isoetharin, isoprenalin, levosalbutamol, mabuterol, meluadrin, metaproterenol, milveterol, orciprenalin, pirbuterol, procaterol, reproterol, rimiterol, ritodrin, salmefamol, soterenol, sulphonterol, terbutalin, tiaramide, tolubuterol, zinterol, 6-Hydroxy-8-{1-hydroxy-2-[2-(4-methoxy-phenyl)-1,1-dimethyl-ethylamino]-ethyl}-4H-benzo[1,4]oxazine-3-one; 8-{2-[2-(2,4-Difluor-phenyl)-1,1-dimethyl-ethylamino]-1-hydroxy-ethyl}-6-hydroxy-4H-benzo[1,4]oxazine-3-one; 8-{2-[2-(3,5-Difluor-phenyl)-1,1-dimethyl-ethylamino]-1-hydroxy-ethyl}-6-hydroxy-4H-benzo[1,4]oxazine-3-one 8-{2-[2-(4-Ethoxy-phenyl)-1,1-dimethyl-ethylamino]-1-hydroxy-ethyl}-6-hydroxy-4H-benzo[1,4]oxazine-3-one; 8-{2-[2-(4-Fluor-phenyl)-1,1-dimethyl-ethylamino]-1-hydroxy-ethyl}-6-hydroxy-4H-benzo[1,4]oxazine-3-one; N-(5-{2-[3-(4,4-Diethyl-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[3-(4,4-Diethyl-6-fluoro-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[3-(4,4-Diethyl-6-methoxy-2-oxo-4H-benzo[d][1,3]oxazine-1-yl)-, 1-dimethyl-propylamino]-1-hydroxy-ethyl}-2-hydroxy-phenyl)-methansulfonamide; N-(5-{2-[1,1-Dimethyl-3-(2-oxo-4,4-dipropyl-4H-benzo[d][1,3]oxazine-1-yl)-propylamino]-1-hydroxy-ethyl}-2-hydroxy-phenyl)-methansulfonamide; 8-{2-[1,1-Dimethyl-3-(2-oxo-2,3-dihydro-benzoimidazol-1-yl)-propylamino]-1-hydroxy-ethyl}-6-hydroxy-4H-benzo[1,4]oxazine-3-one; 8-{2-[1,1-Dimethyl-3-(6-methyl-2-oxo-2,3-dihydro-benzoimidazole-1-yl)-propylamino]-1-hydroxy-ethyl}-6-hydroxy-4H-benzo[1,4]oxazine-3-one; 8-{2-[1,1-Dimethyl-3-(2-oxo-5-trifluormethyl-2,3-dihydro-benzoimidazol-1-yl)-propylamino]-1-hydroxy-ethyl}-6-hydroxy-4H-benzo[1,4]oxazine-3-one; 8-{2-[1,1-Dimethyl-3-(3-methyl-2-oxo-2,3-dihydro-benzoimidazol-1-yl)-propylamino]-1-hydroxy-ethyl}-6-hydroxy-4H-benzo[1,4]oxazine-3-one; N-[2-Hydroxy-5-((1R)-1-hydroxy-2-{2-[4-(2-hydroxy-2-phenyl-ethylamino)-phenyl]-ethylamino}-ethyl)-phenyl]-formamide; 8-Hydroxy-5-((1R)-1-hydroxy-2-{2-[4-(6-methoxy-biphenyl-3-ylamino)-phenyl]-ethylamino}-ethyl)-1H-quinoline-2-one; 8-Hydroxy-5-[(1R)-1-hydroxy-2-(6-phenethylamino-hexylamino)-ethyl]-1H-quinoline-2-one; 5-[(1R)-2-(2-{4-[4-(2-Amino-2-methyl-propoxy)-phenylamino]-phenyl}-ethylamino)-1-hydroxy-ethyl]-8-hydroxy-1H-quinoline-2-one; [3-(4-{6-[(2R)-2-Hydroxy-2-(4-hydroxy-3-hydroxymethyl-phenyl)-ethylamino]-hexyloxy}-butyl)-5-methyl-phenyl]-urea; 4-((1R)-2-{6-[2-(2,6-Dichlor-benzyloxy)-ethoxy]-hexylamino}-1-hydroxy-ethyl)-2-hydroxymethyl-phenol; 3-(4-{6-[(2R)-2-Hydroxy-2-(4-hydroxy-3-hydroxymethyl-phenyl)-ethylamino]-hexyloxy}-butyl)-benzenesulfonamide; 3-(3-{7-[(2R)-2-Hydroxy-2-(4-hydroxy-3-hydroxymethyl-phenyl)-ethylamino]-heptyloxy}-propyl)-benzenesulfonamide; 4-((1R)-2-{6-[4-(3-Cyclopentanesulfonyl-phenyl)-butoxy]-hexylamino}-1-hydroxy-ethyl)-2-hydroxymethyl-phenol, 4-(2-{6-[2-(2,6-dichloro-benzyloxy)-ethoxy]-hexylamino}-1-hydroxy-ethyl)-2-hydroxymethyl-phenol; Vilanterol; N-1-Adamantanyl-2-{3-[(2R)-2-({(2R)-2-hydroxy-2-[4-hydroxy-3-(hydroxymethyl)phenyl]ethyl}amino)propyl]phenyl}acetamide; 2-(3-{2-[2-hydroxy-3-methanesulfonylamino-phenyl)-ethylamino]-propyl}-phenyl)-N-[4-(4-hydroxy-phenyl)-2-vinyl-penta-2,4-dienyl]-acetamide; (1R)-5-{2-[6-(2,2-Difluor-2-phenyl-ethoxy)-hexylamino]-1-hydroxy-ethyl}-8-hydroxy-1H-quinoline-2-one; (R,S)-4-(2-{[6-(2,2-Difluor-4-phenylbutoxy)hexyl]amino}-1-hydroxy-ethyl)-2-(hydroxymethyl)phenol; (R,S)-4-(2-{[6-(2,2-Difluor-2-phenylethoxy)hexyl]amino}-1-hydroxy-ethyl)-2-(hydroxymethyl)phenol; (R,S)-4-(2-{[4,4-Difluor-6-(4-phenylbutoxy)hexyl]amino}-1-hydroxy-ethyl)-2-

(hydroxymethyl)phenol; (R,S)-4-(2-{[6-(4,4-Difluor-4-phenylbutoxy)hexyl]amino}-1-hydroxy-ethyl)-2-(hydroxymethyl)phenol; (R,S)-5-(2-{[6-(2,2-Difluor-2-phenylethoxy)hexyl]amino}-1-hydroxy-ethyl)-8-hydroxyquinoline-2(1H)-one; (R,S)-[2-({6-[2,2-Difluor-2-(3-methylphenyl)ethoxy]hexyl}amino)-1-hydroxyethyl]-2-(hydroxymethyl)phenol; 4-(1R)-2-{[6-(2,2-Difluor-2-phenylethoxy)hexyl]amino}-1-hydroxyethyl)-2-(hydroxymethyl)phenol; (R,S)-2-(Hydroxymethyl)-4-(1-hydroxy-2-{[4,4,515-tetrafluor-6-(3-phenylpropoxy)-hexyl]amino}ethyl)phenol; (R,S)-[5-(2-{[6-(2,2-Difluor-2-phenylethoxy)hexyl]amino}-1-hydroxy-ethyl)-2-hydroxyphenyl]formamide; (R,S)-4-[2-({6-[2-(3-Bromophenyl)-2,2-difluoroethoxy]hexyl}amino)-1-hydroxyethyl]-2-(hydroxymethyl)phenol; (R,S)—N-[3-(1,1-Difluor-2-{[6-({2-hydroxy-2-[4-hydroxy-3-(hydroxymethyl)phenyl]-ethyl}amino)hexyl]oxy}ethyl)phenyl]-urea; 3-[3-(1,1-Difluor-2-{[6-({2-hydroxy-2-[4-hydroxy-3-(hydroxymethyl) phenyl]ethyl}amino)hexyl]oxy}ethyl)phenyl]imidazolidine-2,4-dione; (R,S)-4-[2-({6-[2,2-Difluor-2-(3-methoxyphenyl)ethoxy]hexyl}amino)-hydroxyethyl]-2-(hydroxymethyl)phenol; 5-((1R)-2-{[6-(2,2-Difluor-2-phenylethoxy)hexyl]amino}-1-hydroxyethyl)-8-hydroxyquinoline-2(1H)-one; 4-((1R)-2-{[4,4-Difluor-6-(4-phenylbutoxy)hexyl]amino}-1-hydroxy-ethyl)-2-(hydroxymethyl)phenol; (R,S)-4-(2-{[6-(3,3-Difluor-3-phenylpropoxy)hexyl]amino}-1-hydroxy-ethyl)-2-(hydroxymethyl)phenol; (R,S)-(2-{[6-(2,2-Difluor-2-phenylethoxy)-4,4-difluorohexyl]amino}-1-hydroxyethyl)-2-(hydroxymethyl)phenol; (R,S)-4-(2-{[6-(2,2-Difluor-3-phenylpropoxy)hexyl]amino}-1-hydroxy ethyl)-2-(hydroxymethyl)phenol; 3-[2-(3-Chlor-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide; N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide; 7-[2-(2-{3-[2-(2-Chlor-phenyl)-ethylamino]-propylsulfanyl}-ethylamino)-1-hydroxy-ethyl]-4-hydroxy-3H-benzothiazol-2-one, optionally in the form of the racemates, enantiomers, diastereomers and optionally in the form of the pharmacologically acceptable acid addition salts, solvates or hydrates thereof.

According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among tiotropium salts, particularly the bromide salt, oxitropium salts, particularly the bromide salt, flutropium salts, particularly the bromide salt, ipratropium salts, particularly the bromide salt, Aclidinium salts, particularly the bromide salt, glycopyrronium salts, particularly the bromide salt, trospium salts, particularly the chloride salt, tolterodin, (3R)-1-Phenethyl-3-(9H-xanthene-9-carbonyloxy)-1-azoniabicyclo[2.2.2]octan-salts; 2,2-Diphenyl propionic acid tropenole ester-methobromide; 2,2-Diphenyl propionic acid scopine ester-methobromide; 2-Fluor-2,2-Diphenyl acetic acid scopine ester-methobromide; 2-Fluor-2,2-Diphenyl acetic acid tropenole ester-methobromide; 3,3',4,4'-Tetrafluor benzilic acid tropenole ester-methobromide; 3,3',4,4'-Tetrafluor benzilic acid scopine ester-methobromide; 4,4'-Difluor benzilic acid tropenole ester-methobromide; 4,4'-Difluor benzilic acid scopine ester-methobromide; 3,3'-Difluor benzilic acid tropenole ester-methobromide; 3,3'-Difluor benzilic acid scopine ester-methobromide; 9-Hydroxy-fluorene-9-carboxylic acid tropenole ester-methobromide; 9-Fluor-fluorene-9-carboxylic acid tropenole ester-methobromide; 9-Hydroxy-fluorene-9-carboxylic acid scopine ester-methobromide; 9-Fluor-fluorene-9-carboxylic acid scopine ester-methobromide; 9-Methyl-fluorene-9-carboxylic acid tropenole ester-methobromide; 9-Methyl-fluorene-9-carboxylic acid scopine ester-methobromide; Benzilic acid cyclopropyl tropine ester-methobromide; 2,2-Diphenyl propionic acid cyclopropyltropine ester-methobromide; 9-Hydroxy-xanthene-9-carboxylic acid cyclopropyltropine ester-methobromide; 9-Methyl-fluorene-9-carboxylic acid cyclopropyltropine ester-methobromide; 9-Methyl-xanthene-9-carboxylic acid cyclopropyltropine ester-methobromide; 9-Hydroxy-fluorene-9-carboxilic acid cyclopropyltropine ester-methobromide; 4,4'-Difluor benzilic acid methyl ester cyclopropyltropine ester-methobromide; 9-Hydroxy-xanthene-9-carboxylic acid tropenole ester-methobromide; 9-Hydroxy-xanthene-9-carboxylic acid scopine ester-methobromide; 9-Methyl-xanthene-9-carboxylic acid tropenole ester-methobromide; 9-Methyl-xanthene-9-carboxylic acid scopine ester-methobromide; 9-Ethyl-xanthene-9-carboxylic acid tropenole ester-methobromide; 9-Difluormethyl-xanthene-9-carboxylic acid tropenole ester-methobromide; 9-Hydroxymethyl-xanthene-9-carboxylic acid scopine ester-methobromide; 3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide; N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide; 7-[2-(2-{3-[2-(2-Chloro-phenyl)-ethylamino]-propylsulfanyl}-ethylamino)-1-hydroxy-ethyl]-4-hydroxy-3H-benzothiazol-2-one and Darotropium; optionally in the form of the solvates or hydrates thereof.

In the above-mentioned salts the cations tiotropium, oxitropium, flutropium, ipratropium, glycopyrronium, aclidinium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among beclomethasone, betamethasone, budesonide, butixocort, ciclesonide, deflazacort, dexamethasone, etiprednole, flunisolide, fluticasone, loteprednole, mometasone, prednisolone, prednisone, rofleponide, triamcinolone, tipredane; Pregna-1,4-diene-3,20-dione, 6-fluoro-11-hydroxy-16,17-[(1-methylethylidene) bis(oxy)]-21-[[4-[(nitrooxy)methyl]benzoyl]oxy]-, (6-alpha,11-beta,16-alpha)-(9Cl); 16,17-butylidenedioxy-6,9-difluoro-11-hydroxy-17-(methylthio)androst-4-en-3-one; 6,9-Difluor-17-[(2-furanylcarbonyl)oxy]-11-hydroxy-16-methyl-3-oxo-androsta-1,4-dien-17-carbothione acid (S)-fluoromethylester; (S)-fluoromethyl 6,9-difluoro-17-[(2-furanylcarbonyl)oxy]-11-hydroxy-16-methyl-3-oxo-androsta-1,4-diene-17-carbothionate; 6-alpha,9-alpha-difluoro-11-beta-hydroxy-16alpha-methyl-3-oxo-17alpha-(2,2,3,3-tetramethylcyclopropylcarbonyl)oxy-androsta-1,4-diene-17beta-carboxylic acid cyanomethyl ester, each optionally in the form of the racemates, enantiomers or diastereomers thereof and optionally in the form of the salts and derivatives, solvates and/or hydrates thereof.

Particularly preferably the steroid is selected from among budesonide, fluticasone, mometasone, ciclesonide and (S)-fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulfobenzoates, phosphates, isonicotinates, acetates, propionates, dihydrogen phosphates, palmitates, pivalates or furoates thereof.

PDE4 inhibitors which may be used are preferably compounds selected from among enprofyllin, theophyllin, roflumilast, ariflo (cilomilast), tofimilast, pumafentrin, lirimilast, apremilast, arofyllin, atizoram, oglemilast, tetomilast; 5-[(N-(2,5-dichloro-3-pyridinyl)-carboxamide]-8-methoxy-Quinoline (D-4418); 5-[N-(3,5-dichloro-1-oxido-4-pyridinyl)-carboxamide]-8-methoxy-2-(trifluoromethyl)-Quinoline (D-4396 (Sch-351591)); N-(3,5-dichloropyrid-4-yl)-[1-(4-fluorobenzyl)-5-hydroxy-indol-3-yl]glyoxylic acid amide (AWD-12-281 (GW-842470)); 9-[(2-fluorophenyl)methyl]-N-methyl-2-(trifluoromethyl)-9H-Purin-6-amine (NCS-613); 4-[(2R)-2-[3-(cyclopentyloxy)-4-methoxyphenyl]-2-phenylethyl]-Pyridine (CDP-840); N-[(3R)-3,4,6,7-tetrahydro-9-methyl-4-oxo-1-phenylpyrrolo[3,2,1-jk][1,4]benzodiazepin-3-yl]-4-Pyridinecarboxamide (PD-168787); 4-[6,7-diethoxy-2,3-bis(hydroxymethyl)-1-naphthalenyl]-1-(2-methoxyethyl)-2(1H)-Pyridinone (T-440); 2-[4-[6,7-diethoxy-2,3-bis(hydroxymethyl)-1-naphthalenyl]-2-pyridinyl]-4-(3-pyridinyl)-1 (2H)-Phthalazinone (T-2585); (3-(3-cyclopenyloxy-4-methoxybenzyl)-6-ethylamino-8-isopropyl-3H-purine (V-11294A); beta-[3-(cyclopentyloxy)-4-methoxyphenyl]-1,3-dihydro-1,3-dioxo-2H-Isoindole-2-propanamide (CDC-801); Imidazo[1,5-a]pyrido[3,2-e]pyrazine-6(5H)-one, 9-ethyl-2-methoxy-7-methyl-5-propyl-(D-22888); 5-[3-(cyclopentyloxy)-4-methoxyphenyl]-3-[(3-methylphenyl)methyl]-, (3S,5S)-2-Piperidinon (HT-0712); 4-[1-[3,4-bis(difluoromethoxy)phenyl]-2-(3-methyl-1-oxido-4-pyridinyl)ethyl]-alpha,alpha-bis(trifluoromethyl)-Benzenemethanol (L-826141); N-(3,5-Dichloro-1-oxo-pyridin-4-yl)-4-difluormethoxy-3-cyclopropylmethoxybenzamide; (−)p-[(4aR*,10bS*)-9-Ethoxy-1,2,3,4,4a,10b-hexahydro-8-methoxy-2-methyl-benzo[s][1,6]naphthyridin-6-yl]-N,N-diisopropylbenzamide; (R)-(+)-1-(4-Brombenzyl)-4-[(3-cyclopentyloxy)-4-methoxyphenyl]-2-pyrrolidon; 3-(Cyclopentyloxy-4-methoxyphenyl)-1-(4-N'—[N-2-cyano-S-methyl-isothioureido]benzyl)-2-pyrrolidon; cis[4-Cyano-4-(3-cyclopentyloxy-4-methoxyphenyl)cyclohexan-1-carboxylic acid]; 2-carbomethoxy-4-cyano-4-(3-cyclopropylmethoxy-4-difluoromethoxyphenyl) cyclohexan-1-one; cis[4-Cyano-4-(3-cyclopropylmethoxy-4-difluormethoxyphenyl)cyclohexan-1-ol]; (R)-(+)-Ethyl[4-(3-cyclopentyloxy-4-methoxyphenyl)pyrrolidin-2-yliden] acetat; (S)-(−)-Ethyl[4-(3-cyclopentyloxy-4-methoxyphenyl)pyrrolidin-2-yliden]acetat; 9-Cyclopentyl-5,6-dihydro-7-ethyl-3-(2-thienyl)-9H-pyrazolo[3,4-c]-1,2,4-triazolo[4,3-a]pyridin; 9-Cyclopentyl-5,6-dihydro-7-ethyl-3-(tert-butyl)-9H-pyrazolo[3,4-c]-1,2,4-triazolo[4,3-a]pyridin, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

LTD4-antagonists which may be used are preferably compounds selected from among montelukast, pranlukast, zafirlukast; (E)-8-[2-[4-[4-(4-Fluorophenyl)butoxy]phenyl]ethenyl]-2-(1H-tetrazol-5-yl)-4H-1-benzopyran-4-one (MEN-91507); 4-[6-Acetyl-3-[3-(4-acetyl-3-hydroxy-2-propylphenylthio)propoxy]-2-propylphenoxy]-butyric acid (MN-001); 1-(((R)-(3-(2-(6,7-Difluor-2-quinolinyl)ethenyl)phenyl)-3-(2-(2-hydroxy-2-propyl)phenyl)thio)methylcyclopropane-acetic acid; 1-(((1R)-3(3-(2-(2,3-Dichlorthieno[3,2-b]pyridin-5-yl)-(E)-ethenyl)phenyl)-3-(2-(1-hydroxy-1-methylethyl)phenyl) propyl)thio)methyl)cyclopropane acetic acid; [2-[[2-(4-tert-Butyl-2-thiazolyl)-5-benzofuranyl]oxymethyl]phenyl] acetic acid, optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

The EGFR-inhibitors used are preferably compounds selected from among 4-[(3-chloro-4-fluorophenyl)amino]-6-{[4-(morpholine-4-yl)-1-oxo-2-butene-1-yl]amino}-7-cyclopropylmethoxy-quinazoline, 4-[(3-chloro-4-fluorophenyl)amino]-6-{[4-(N,N-diethylamino)-1-oxo-2-butene-1-yl] amino}-7-cyclopropylmethoxy-quinazoline, 4-[(3-chloro-4-fluorophenyl)amino]-6-{[4-(N,N-dimethylamino)-1-oxo-2-butene-1-yl]amino}-7-cyclopropylmethoxy-quinazoline, 4-[(R)-(1-phenyl-ethyl)amino]-6-{[4-(morpholine-4-yl)-1-oxo-2-butene-1-yl]amino}-7-cyclopentyloxy-quinazoline, 4-[(3-chloro-4-fluoro-phenyl)amino]-6-{[4-((R)-6-methyl-2-oxo-morpholine-4-yl)-1-oxo-2-butene-1-yl]amino}-7-cyclopropylmethoxy-quinazoline, 4-[(3-chloro-4-fluoro-phenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholine-4-yl)-1-oxo-2-butene-1-yl]amino}-7-cyclopropylmethoxy-quinazoline, 4-[(3-chloro-4-fluoro-phenyl)amino]-6-[2-((S)-6-methyl-2-oxo-morpholine-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-butene-1-yl}amino)-7-cyclopropylmethoxy-quinazoline, 4-[(3-chloro-4-fluorophenyl)amino]-6-{[4-(N,N-dimethylamino)-1-oxo-2-butene-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-butene-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-butene-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-butene-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-butene-1-yl}amino)-7-cyclopropylmethoxy-quinazoline, 4-[(R)-(1-Phenyl-ethyl)amino]-6-({4-[N-(2-methoxy-ethyl)-N-methyl-amino]-1-oxo-2-butene-1-yl}amino)-7-cyclopropylmethoxy-quinazoline, 4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline, 4-[(3-chloro-4-fluorophenyl)amino]-6-{[4-(N,N-dimethylamino)-1-oxo-2-butene-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-butene-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-butene-1-yl}amino)-7-cyclopentyloxy-quinazoline, 4-[(3-chloro-4-fluorophenyl)amino]-6-{[4-(N-cyclopropyl-N-methyl-amino)-1-oxo-2-butene-1-yl]amino}-7-cyclopentyloxy-quinazoline, 4-[(3-chloro-4-fluorophenyl)amino]-6-{[4-(N,N-dimethylamino)-1-oxo-2-butene-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-butene-1-yl]amino}-7-[(S)-(tetrahydrofuran-2-yl)methoxy]-quinazoline, 4-[(3-ethynyl-phenyl)amino]-6.7-bis-(2-methoxy-ethoxy)-quinazoline, 4-[(3-chloro-4-fluorophenyl)amino]-7-[3-(morpholine-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-butene-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholine-4-yl)-1-oxo-2-butene-1-yl]amino}-7-methoxy-quinazoline, 4-[(3-chloro-4-fluorophenyl)amino]-6-{[4-(morpholine-4-yl)-1-oxo-2-butene-1-yl]-amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-butene-1-yl}amino)-7-[(tetrahydrofuran-2-yl)methoxy]-quinazoline, 4-[(3-ethynyl-phenyl)amino]-6-{[4-(5.5-dimethyl-2-oxo-morpholine-4-yl)-1-oxo-2-butene-1-yl]amino}-quinazoline, 4-[(3-chloro-4-fluoro-phenyl)amino]-6-[2-(2.2-dimethyl-6-oxo-morpholine-4-yl)-ethoxy]-7-methoxy-quinazoline, 4-[(3-chloro-4-fluoro-phenyl)amino]-6-[2-(2.2-dimethyl-6-oxo-morpholine-4-yl)-ethoxy]-7-[(R)-(tetrahydrofuran-2-yl)methoxy]-quinazoline, 4-[(3-chloro-4-fluoro-phenyl)amino]-7-[2-(2.2-dimethyl-6-oxo-morpholine-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholine-4-yl)-piperidine-1-yl]-ethoxy}-7-methoxy-quinazoline, 4-[(3-chloro-4-fluoro-phenyl)amino]-6-[1-(tert.-butyloxycarbonyl)-piperidine-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidine-4-yloxy)-7-methoxy-quinazoline, 4-[(3-chloro-4-fluoro-phenyl)amino]-6-{1-[(morpholine-4-yl)carbonyl]-piperidine-4-yloxy}-7-methoxy-quinazoline, 4-[(3-chloro-4-fluoro-phenyl)amino]-6-{1-[(methoxymethyl)carbonyl]-piperidine-4-yloxy}-7-methoxy-quinazoline, 4-[(3-chloro-4-fluoro-phenyl)amino]-6-(piperidine-3-yloxy)-7-methoxy-quinazoline, 4-[(3-chloro-4-fluoro-phenyl)amino]-6-[1-(2-acetylamino-ethyl)-piperidine-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino-cyclohexan-1-yloxy}-7-methoxy-quinazoline, 4-[(3-chloro-4-fluoro-phenyl)amino]-6-{trans-4-[(morpholine-4-yl)carbonylamino]-cyclohexan-1-yloxy}-7-methoxy-quinazoline, 4-[(3-chloro-4-fluoro-phenyl)amino]-6-{trans-4-[(morpholine-4-yl)sulphonylamino-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidine-1-yl)carbonyl]-piperidine-4-yloxy}-7-methoxy-quinazoline, 4-[(3-chloro-4-fluoro-phenyl)amino]-6-(1-aminocarbonylmethyl-piperidine-4-yloxy)-7-methoxy-q uinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholine-4-yl)carbonyl]-N-methyl-amino}-cyclohexan-1-yloxy)-7-methoxy-quinazolin; 4-{2-[4-(3-chloro-4-fluoro-phenylamino)-7-methoxy-quinazolin-6-yloxy]-ethyl}-6-methyl-morpholine-2-one, 4-{4-[4-(3-chloro-2-fluoro-phenylamino)-7-methoxy-quinazolin-6-yloxy]-cyclohexyl}-1-methyl-piperazine-2-one, 4-[(3-chloro-4-fluoro-phenyl)amino]-6-(cis-4-{N-[(morpholine-4-yl)sulphonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidine-4-yloxy)-7-ethoxy-quinazoline, 4-[(3-chloro-4-fluoro-phenyl)amino]-6-(1-methanesuphonyl-piperidine-4-yloxy)-7-(2-methoxy-ethoxy)-quinazoline, 4-[(3-chloro-4-fluoro-phenyl)amino]-6-[1-(2-methoxy-acetyl)-piperidine-4-yloxy]-7-(2-methoxy-ethoxy)-quinazoline, 4-[(3-chloro-4-fluorophenyl)amino]-6-(cis-4-acetylamino-cyclohexan-1-yloxy)-7-methoxy-quinazoline, 4[(3-ethynyl-phenyl)amino]-6-[1-(tert.-butyloxycarbonyl)-piperidine-4-yloxy]-7-methoxy-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-{N-[(piperidine-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazine-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholine-4-yl)carbonylamino-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidine-4-yloxy}-7-methoxy-quinazoline, 4-[(3-chloro-4-fluoro-phenyl)amino]-6-{1-[(morpholine-4-yl)carbonyl]-piperidine-4-yloxy}-7-(2-methoxy-ethoxy)-quinazoline, 4[(3-ethynyl-phenyl)amino]-6-(1-acetyl-piperidine-4-yloxy)-7-methoxy-quinazoline, 4-[(3-ethynyl-phenyl)amino]-6-(1-methyl-piperidine-4-yloxy)-7-methoxy-quinazoline, 4-[(3-ethynyl-phenyl)amino]-6-(1-methanesulphonyl-piperidine-4-yloxy)-7-methoxy-quinazoline, 4[(3-chloro-4-fluoro-phenyl)amino]-6-(1-methyl-piperidine-4-yloxy)-7(2-methoxy-ethoxy)-quinazoline, 4-[(3-chloro-4-fluoro-phenyl)amino]-6-(1-isopropyloxycarbonyl-piperidine-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4[(3-ethynyl-phenyl)amino]-6-(piperidine-4-yloxy)-7-methoxy-quinazoline, 4-[(3-ethynyl-phenyl)amino]-6-[1-(2-methoxy-acetyl)-piperidine-4-yloxy]-7-methoxy-quinazoline, 4[(3-ethynyl-phenyl)amino]-6-{1-[(morpholine-4-yl)carbonyl]-piperidine-4-yloxy}-7-methoxy-quinazoline, 4-[(3-chloro-4-fluoro-phenyl)amino]-6-{1-[(cis-2,6-dimethyl-morpholine-4-yl)carbonyl]-piperidine-4-yloxy}-7-methoxy-quinazoline, 4-[(3-chloro-4-fluoro-phenyl)amino]-6-{1-[(2-methyl-morpholine-4-yl)carbonyl]-piperidine-4-yloxy}-7-m ethoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidine-4-yloxy}-7-methoxy-quinazoline, 4-[(3-chloro-4-fluoro-phenyl)amino]-6-{1-[(N-methyl-N-2-methoxyethyl-amino)carbonyl]-piperidine-4-yloxy}-7-methoxy-quinazoline, 4-[(3-chloro-4-fluoro-phenyl)amino]-6-(1-ethyl-piperidine-4-yloxy)-7-methoxy-quinazoline, 4-[(3-chloro-4-fluoro-phenyl)amino]-6-{1-[(2-methoxyethyl)carbonyl]-piperidine-4-yloxy}-7-methoxy-quinazoline, 4-[(3-chloro-4-fluoro-phenyl)amino]-6-{1-[(3-methoxypropyl-amino)-carbonyl]-piperidine-4-yloxy}-7-methoxy-quinazoline, 4-[(3-chlIoro-4-flluoro-phenyl)amino]-6-[cis-4-(N-methanesulphonyl-N-methyl-amino)-cyclohexan-1-yloxy]-7-methoxy-quinazoline, 4[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholine-4-yl)carbonyl]-N-methyl-amino}-cyclohexan-1-yloxy)-7-methoxy-quinazoline, 4-[(3-chloro-4-fluoro-phenyl)amino]-6-[2-(2.2-dimethyl-6-oxo-morpholine-4-yl)-ethoxy]-7-[(S)-(tetrahydrofuran-2-yl)methoxy]-quinazoline, 4-[(3-chloro-4-fluoro-phenyl)amino]-6-(1-methanesuphonyl-piperidine-4-yloxy)-7-methoxy-quinazoline, 4-[(3-chloro-4-fluoro-phenyl)amino]-6-(1-cyano-piperidine-4-yloxy)-7-methoxy-quinazoline, 3-Cyano-4-[(3-chlor-4-fluorphenyl)amino]-6-{[4-(N,N-dimethylamino)-1-oxo-2-butene-1-yl]amino}-7-ethoxy-quinoline, [4-[(3-chloro-4-fluoro-phenyl)amino]-6-{[4-(homomorpholine-4-yl)-1-oxo-2-butene-1-yl]amino}-7-[(S)-(tetrahydrofuran-3-yl)oxy]-quinazoline, 4-[(3-chloro-4-fluoro-phenyl)amino]-7-(2-{4-[(S)-(2-oxo-tetrahydrofuran-5-yl)carbonyl]-piperazine-1-yl}-ethoxy)-6-[(vinylcarbonyl)amino]-quinazoline, 4-[(3-chloro-4-fluoro-phenyl)amino]-7-[2-((S)-6-methyl-2-oxo-morpholine-4-yl)-ethoxy]-6-[(vinylcarbonyl)amino]-quinazoline, 4-[(3-chloro-4-fluoro-phenyl)amino]-7-[4-((R)-6-methyl-2-oxo-morpholine-4-yl)-butyloxy]-6-[(vinylcarbonyl)amino]-quinazoline, 4-[(3-chloro-4-fluoro-phenyl)amino]-7-[4-((S)-6-methyl-2-oxo-morpholine-4-yl)-butyloxy]-6-[(vinylcarbonyl)amino]-quinazoline, 4-[(3-chloro-4-fluoro-phenyl)amino]-7-(2-{4-[(S)-(2-oxo-tetrahydrofuran-5-yl)carbonyl]-piperazine-1-yl}-ethoxy)-6-[(vinylcarbonyl)amino]-quinazoline, 4-[(3-chloro-4-fluoro-phenyl)amino]-7-[2-((S)-6-methyl-2-oxo-morpholine-4-yl)-ethoxy]-6-[(vinylcarbonyl)amino]-quinazoline, 4-[(3-chloro-4-fluoro-phenyl)amino]-7-[4-((R)-6-methyl-2-oxo-morpholine-4-yl)-butyloxy]-6-[(vinylcarbonyl)amino]-quinazoline, 4-[(3-chloro-4-fluoro-phenyl)amino]-7-[4-((S)-6-methyl-2-oxo-morpholine-4-yl)-butyloxy]-6-[(vinylcarbonyl)amino]-quinazoline, cetuximab, trastuzumab, panitumumab (=ABX–EGF), Mab ICR-62, gefitinib, pelitinib, canertinib and erlotinib, optionally in the form of the racemates, enantiomers or diastereomers thereof, optionally in the form of the pharmacologically acceptable acid addition salts thereof, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, olopatadine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among lexipafant, 4-(2-chlorophenyl)-9-methyl-2-[3(4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpho-linyl) carbonyl]-4H,7H-cyclo-penta-[4,5]thieno-[3,2-f][1,2,4] triazolo[4,3-a][1,4]diazepines. Any reference to the above-mentioned above-mentioned PAF-antagonists includes within the scope of the present invention a reference to any pharmacologically acceptable acid addition salts thereof which may exist.

Examples of non-steroidal anti-inflammatory drugs (NSAIDs) preferably include compounds selected from among Aceclofenac, Acemetacin, Acetylsalicylsaure, Alclofenac, Alminoprofen, Amfenac, Ampiroxicam, Antolmetinguacil, Anirolac, Antrafenin, Azapropazon, Benorilat, Bermoprofen, Bindarit, Bromfenac, Bucloxinsaure, Bucolom, Bufexamac, Bumadizon, Butibufen, Butixirat, Carbasalatcalcium, Carprofen, Cholin Magnesium Trisalicylat, Celecoxib, Cinmetacin, Cinnoxicam, Clidanac, Clobuzarit, Deboxamet, Dexibuprofen, Dexketoprofen, Diclofenac, Diflunisal, Droxicam, Eltenac, Enfenaminsaure, Etersalat, Etodolac, Etofenamat, Etoricoxib, Feclobuzon, Felbinac, Fenbufen, Fenclofenac, Fenoprofen, Fentiazac, Fepradinol, Feprazon, Flobufen, Floctafenin, Flufenaminsaure, Flufenisal, Flunoxaprofen, Flurbiprofen, Flurbiprofenaxetil, Furofenac, Furprofen, Glucametacin, Ibufenac, Ibuprofen, Indobufen, Indometacin, Indometacinfarnesil, Indoprofen, Isoxepac, Isoxicam, Ketoprofen, Ketorolac, Lobenzarit, Lonazolac, Lornoxicam, Loxoprofen, Lumiracoxib, Meclofenaminsaure, Meclofen, Mefenaminsaure, Meloxicam, Mesalazin, Miroprofen, Mofezolac, Nabumeton, Naproxen, Nifluminsäure, Olsalazin, Oxaprozin, Oxipinac, Oxyphenbutazon, Parecoxib, Phenylbutazon, Pelubiprofen, Pimeprofen, Pirazolac, Priroxicam, Pirprofen, Pranoprofen, Prifelon, Prinomod, Proglumetacin, Proquazon, Protizininsaure, Rofecoxib, Romazarit, Salicylamid, Salicylsaure, Salmistein, Salnacedin, Salsalat, Sulindac, Sudoxicam, Suprofen, Talniflumat, Tenidap, Tenosal, Tenoxicam, Tepoxalin, Tiaprofensaure, Taramid, Tilnoprofenarbamel, Timegadin, Tinoridin, Tiopinac, Tolfenaminsaure, Tolmetin, Ufenamat, Valdecoxib, Ximoprofen, Zaltoprofen und Zoliprofen.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-beta-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, glycolithocholic acid sulphate, ibuprofen, indomethacin, indoprofen, ketoprofen, lithocholic acid sulphate, methotrexate, ((E)-3-[[[3-[2-(7-chloro-2-quinolinyl)ethenyl]phenyl]-[[3-dimethylamino)-3-oxopropyl] thio]methyl]thio]-propanoic acid), alpha-naphthyl-beta-D-glucuronide, nitrobenzyl mercaptopurine riboside, probenecid, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

Examples of JAK inhibitors preferably include compounds selected from among Tofacitinib and Ruxolitinib.

Examples of immunesuppressive agents preferably include compounds selected from among mycophenolate mofetil, mycophenolic acid, azathioprine, cyclosporine, tacrolimus, pimecrolimus, abetimus, gusperimus and leflunomide.

An example of a cytostaticum is cyclophosphamide.

The invention relates more preferably to the use of MRP4-inhibitors for preparing a pharmaceutical composition for treating respiratory complaints, containing the SYK-inhibitors of formula 1 or 1' and MRP4-inhibitors according to the invention, the MRP4-inhibitors preferably being selected from among dehydroepiandrosterone 3-sulphate, estradiol 3,17-disulphate, flurbiprofen, indomethacin, indoprofen, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydro-p-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the SYK-inhibitors of formula 1 or 1', MRP4-inhibitors and another active substance according to the invention, such as, for example, an anticholinergic, a PDE4 inhibitor, a steroid, an LTD4-antagonist or a betamimetic, and the preparation thereof and the use thereof for treating respiratory complaints.

Compounds which may be used as iNOS inhibitors are compounds selected from among: S-(2-aminoethyl)isothiourea, aminoguanidine, 2-aminomethylpyridine, 5,6-dihydro-6-methyl-4H-1,3-Thiazine-2-amine (=AMT), L-canavanine, 2-iminopiperidine, S-isopropylisothiourea, S-methylisothiourea, S-ethylisothiourea, S-methyltiocitrullin, S-ethylthiocitrulline, L-NA ($N^\omega$-nitro-L-arginine), L-NAME (N$\omega$-nitro-L-argininemethylester), L-NMMA ($N^G$-monomethyl-L-arginine), L-NIO (N$\omega$-iminoethyl-L-ornithine), L-NIL (N$\omega$-iminoethyl-lysine), (S)-6-acetimidoylamino-2-aminohexanoic acid (1H-tetrazol-5-yl)-amide (SC-51) (*J. Med. Chem.* 2002, 45, 1686-1689), N-[[3-(aminomethyl)phenyl] methyl]-Ethanimidamide (=1400W), (S)-4-(2-acetimidoylamino-ethylsulphanyl)-2-amino-butyric acid (GW274150) (*Bioorg. Med. Chem. Lett.* 2000, 10, 597-600), 2-[2-(4-methoxy-pyridin-2-yl)-ethyl]-3H-imidazo[4,5-b]pyridine (BYK191023) (*Mol. Pharmacol.* 2006, 69, 328-337), 2-((R)-3-amino-1-phenyl-propoxy)-4-chloro-5-fluorobenzonitrile (WO 01/62704), 2-((1R,3S)-3-amino-4-hydroxy-1-thiazol-5-yl-butylsulphanyl)-6-trifluoromethyl-nicotinonitrile (WO 2004/041794), 2-((1R.3S)-3-amino-4-hydroxy-1-thiazol-5-yl-butylsulphanyl)-4-chloro-benzonitrile (WO 2004/041794), 2-((1R.3S)-3-amino-4-hydroxy-1-thiazol-5-yl-butylsulphanyl)-5-chloro-benzonitrile (WO 2004/041794), (2S.4R)-2-amino-4-(2-chloro-5-trifluoromethyl-phenylsulphanyl)-4-thiazol-5-yl-butan-1-ol (WO 2004/041794), 2-((1R.3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamine such as e.g. (1 S.5S.6R)-7-chloro-5-methyl-2-azabicyclo[4.1.0]hept-2-en-3-ylamine (ONO-1714) (*Biochem. Biophys. Res. Commun.* 2000, 270, 663-667), (4R,5R)-5-ethyl-4-methyl-thiazolidin-2-ylideneamine (*Bioorg. Med. Chem.* 2004, 12, 4101), (4R,5R)-5-ethyl-4-methyl-selenazolidin-2-ylideneamine (*Bioorg. Med. Chem. Lett.* 2005, 15, 1361), 4-aminotetrahydrobiopterine (*Curr. Drug Metabol.* 2002, 3, 119-121), (E)-3-(4-chloro-phenyl)-N-(1-{2-oxo-2-[4-(6-trifluoromethyl-pyrimidin-4-yloxy)-piperidine-1-yl]-ethylcarbamoyl}-2-pyridin-2-yl-ethyl)-acrylamide (FR260330) (*Eur. J. Pharmacol.* 2005, 509, 71-76), 3-(2,4-difluoro-phenyl)-6-[2-(4-imidazol-1-ylmethyl-phenoxy)-ethoxy]-2-phenyl-pyridine (PPA250) (*J. Pharmaco Exp. Ther.* 2002, 303, 52-57), 3-{[(benzo[1,3]dioxol-5-ylmethyl)-carbamoyl]-methyl}-4-(2-imidazol-1-yl-pyrimidin-4-yl)-piperazine-1-carboxylate (BBS-1) (*Drugs Future* 2004, 29, 45-52), (R)-1-(2-imidazol-1-yl-6-methyl-pyrimidin-4-yl)-pyrrolidine-2-carboxylic acid (2-benzo[1,3]dioxol-5-yl-ethyl)-amide (BBS-2) (*Drugs Future* 2004, 29, 45-52) and the pharmaceutical salts, prodrugs or solvates thereof.

Examples of iNOS-inhibitors within the scope of the present invention may also include antisense oligonucleotides, particularly those antisense oligonucleotides which bind iNOS-coding nucleic acids. For example, WO 01/52902 describes antisense oligonucleotides, particularly antisense oligonucleotides, which bind iNOS coding nucleic acids, for modulating the expression of iNOS. iNOS-antisense oligonucleotides as described particularly in WO 01/52902 may therefore also be combined with the PDE4-inhibitors of the present invention on account of their similar effect to the iNOS-inhibitors.

Suitable HMG-CoA reductase inhibitors (also called statins) which may be preferably used in double or triple combinations with the compounds of formula 1 are selected from among Atorvastatin, Cerivastatin, Flurvastatin, Lovastatin, Pitavastatin, Pravastatin, Rosuvastatin, Simvastatin, optionally in form of their pharmaceutically available acid addition salts, prodrugs, solvates or hydrates thereof.

8. FORMULATIONS

The compounds of formula 1 or 1' according to the invention also have properties required for the manufacture of suitable pharmaceutical dosage forms. These properties include for instance properties relevant for sufficient bioavailability of the active ingredient, in particular sufficiently high solubilites thereof such as for instance a solubility that is >2 μg/ml measured in aqueous solution at pH 6.8.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula 1 or 1' according to the preferred embodiments above.

It is particularly preferable if the compounds of formula 1 or 1' are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like.

Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 or 1' are administered by inhalation, particularly preferably if they are administered once or twice a day. For this purpose, the compounds of formula 1 or 1' have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 or 1' are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain the compounds of formula 1 or 1' dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 or 1' according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, together with a imidazolyl-pyrimidine according to formula 1 or 1' and one or more combination partners selected from those described above.

The invention claimed is:

1. A method for the treatment of a disease which can be treated by inhibition of the SYK enzyme comprising administering to a subject in need thereof a therapeutically effective amount of a compound of formula 1 or 1',

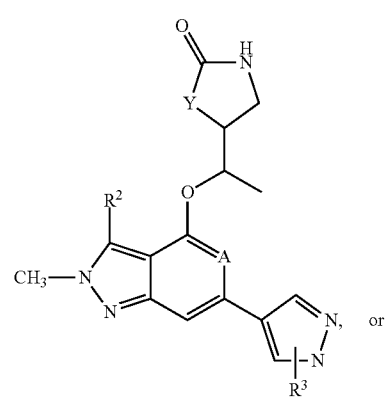

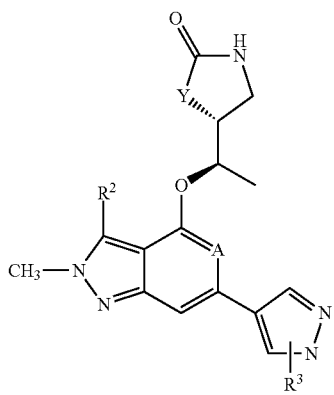

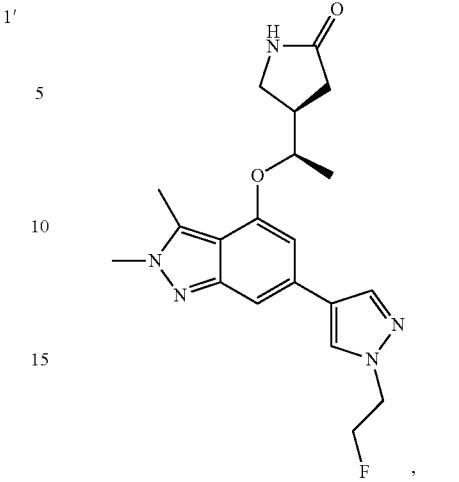

wherein A is either N or CH, wherein Y is either —O— or CH$_2$, wherein R$^3$ is a substituent in ortho- or in meta-position of the pyrazolyl-ring of formula 1 and is selected from the group consisting of linear or branched —C$_{1-6}$-alkyl, —C$_{1-6}$-haloalkyl, —C$_{3-6}$-cycloalkyl, —C$_{1-4}$-alkylene-C$_{3-6}$-cycloalkyl, a five- or six-membered monocyclic heterocycle with 1, 2 or three heteroatoms each independently selected from O, S or N, a nine- to 10-membered bicyclic heterocycle with 1, 2 or 3 heteroatoms each independently selected from O, S or N, wherein R$^3$ is optionally substituted by one, two, three or four substituents each independently from each other selected from the group consisting of halogen, —C$_{1-3}$-alkyl, oxo, —CN wherein R$^2$ is selected from the group consisting of —C$_{1-3}$-alkyl, —C$_{1-3}$-haloalkyl, F, Br, Cl, and the pharmaceutically acceptable salts of the aforementioned compounds and wherein the disease is selected from the group consisting of allergic rhinitis, asthma, COPD, B-cell lymphoma, dermatitis, rheumatoid arthritis, ulcerative colitis, lupus erythematodes, lupus nephritis, Crohn's disease, multiple sclerosis, psoriasis, sclerodermy, T-cell lymphoma, systemic sclerosis (SSc), and malaria.

2. The method of claim 1, wherein R$^2$ is methyl or a pharmaceutically acceptable salt of one of the aforementioned compounds.

3. The method of claim 1, wherein R$^2$ is F or a pharmaceutically acceptable salt of one of the aforementioned compounds.

4. The method of claim 1, wherein A is N or a pharmaceutically acceptable salt of one of the aforementioned compounds.

5. The method of claim 1, wherein A is CH or a pharmaceutically acceptable salt of one of the aforementioned compounds.

6. The method of claim 1, wherein the compound of formula 1 is selected from the group consisting of

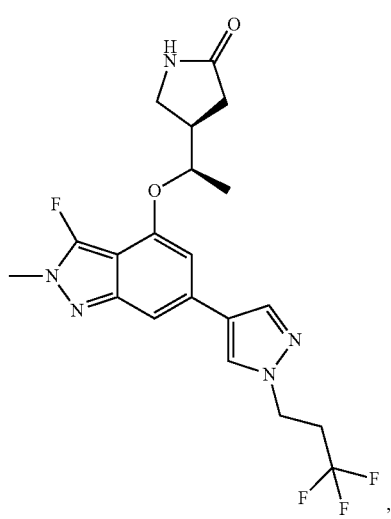

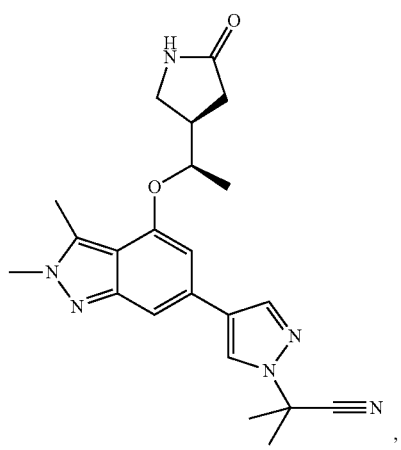

and a pharmaceutically acceptable salt of one of the aforementioned compounds.

7. The method of claim 1, wherein the compound of formula 1 is selected from the group consisting of 137
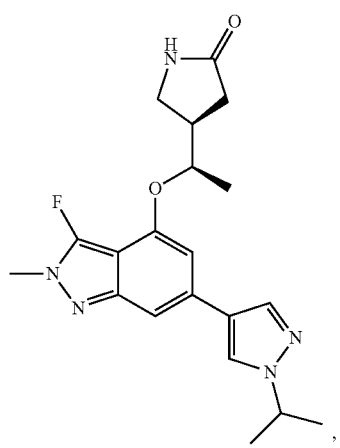
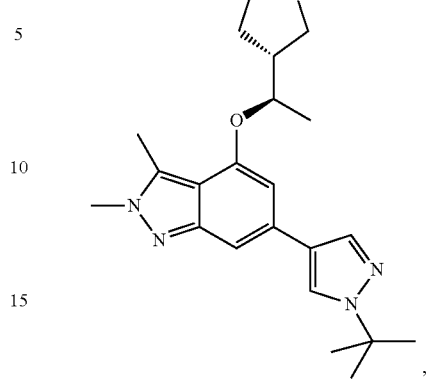
138
-continued
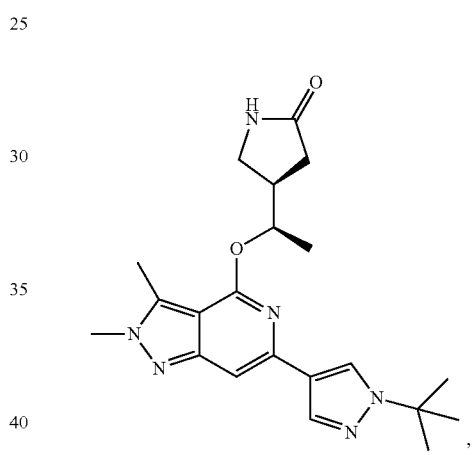
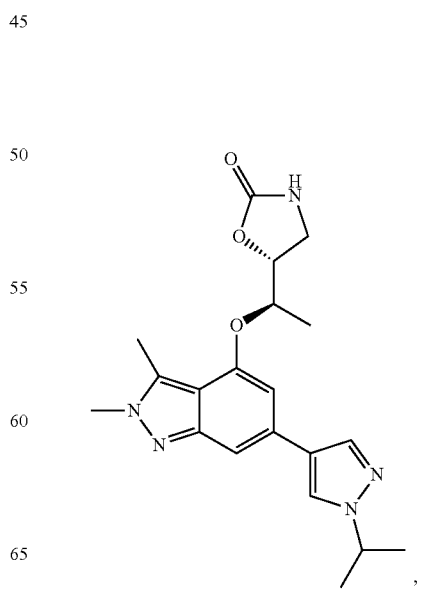

139
-continued
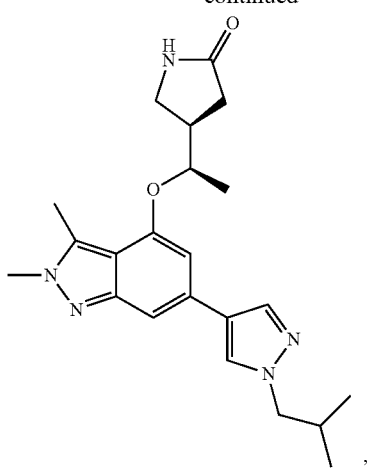
and a pharmaceutically acceptable salt of one of the aforementioned compounds.
8. The method of claim 1, wherein the compound of formula 1 is selected from the group consisting of
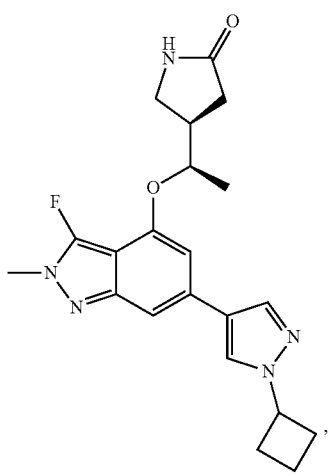
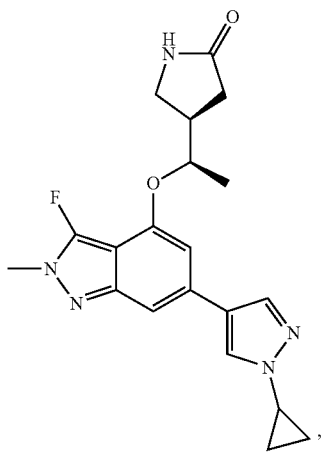
140
-continued
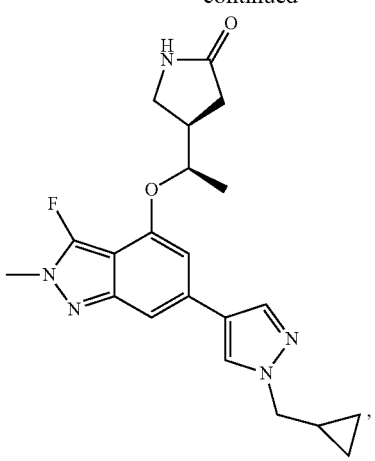
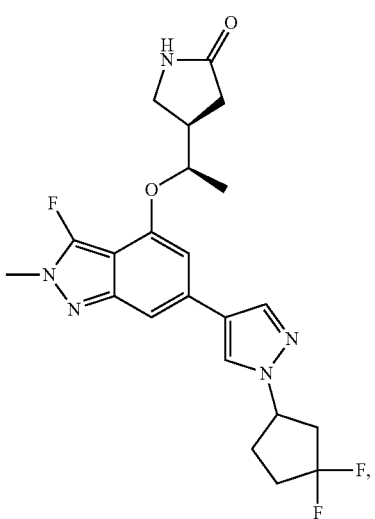
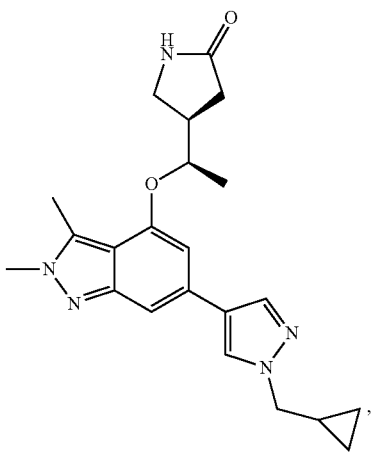

141
-continued
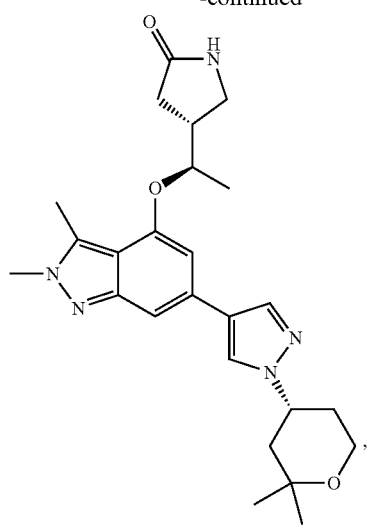
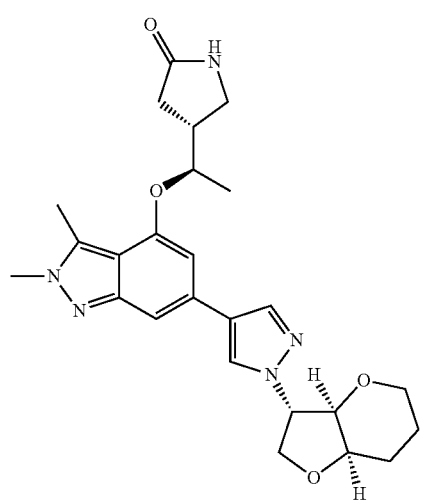
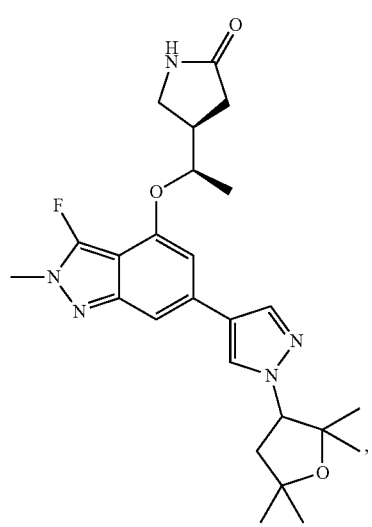
142
-continued
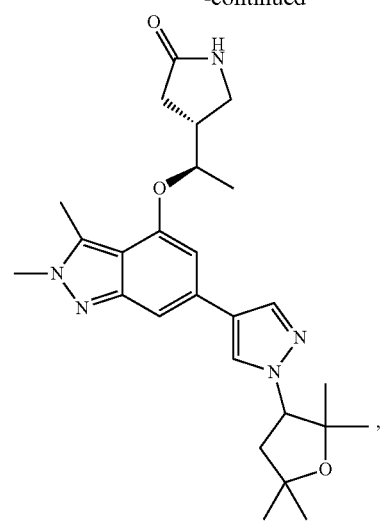

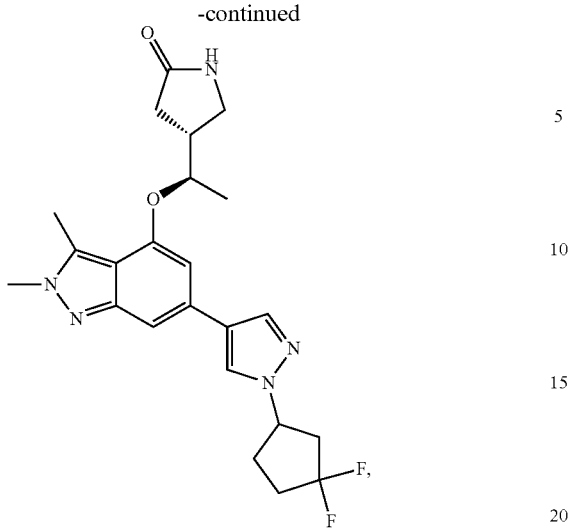

and a pharmaceutically acceptable salt of one of the aforementioned compounds.

9. The method of claim 1, wherein the disease is selected from the group consisting of asthma, COPD, rheumatoid arthritis, systemic sclerosis, ulcerative colitis, Crohn's disease, lupus erythematodes, lupus nephritis, multiple sclerosis and psoriasis.

10. The method of claim 1, wherein the disease is COPD.

11. The method of claim 1, wherein the disease is asthma.

* * * * *